US008863436B2

(12) United States Patent
Becker et al.

(10) Patent No.: US 8,863,436 B2
(45) Date of Patent: Oct. 21, 2014

(54) AUTOMATED SEED SAMPLING APPARATUS, METHOD AND SYSTEM

(75) Inventors: Steven M. Becker, Johnston, IA (US);
Jason M. Cope, Ankeny, IA (US);
David Kurth, Grimes, IA (US); Joshua L. Mongan, Saint Charles, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 853 days.

(21) Appl. No.: 12/981,954

(22) Filed: Dec. 30, 2010

(65) Prior Publication Data

US 2011/0160068 A1     Jun. 30, 2011

Related U.S. Application Data

(60) Provisional application No. 61/291,516, filed on Dec. 31, 2009.

(51) Int. Cl.
*A01C 1/00* (2006.01)
*G01N 33/00* (2006.01)
*G01N 1/04* (2006.01)
*G01N 35/02* (2006.01)
*G01N 35/10* (2006.01)

(52) U.S. Cl.
CPC .......... *G01N 1/04* (2013.01); *G01N 2033/0077* (2013.01); *G01N 2001/045* (2013.01); *G01N 35/028* (2013.01); *G01N 35/1065* (2013.01)
USPC .......................................................... 47/14

(58) Field of Classification Search
USPC .............................................. 47/14, 58.1 SE
See application file for complete search history.

(56) References Cited

U.S. PATENT DOCUMENTS

| 3,195,485 A | 7/1965 | Reynolds |
| 3,530,372 A | 9/1970 | Laukien |
| 3,572,548 A | 3/1971 | Fuchs |
| 4,230,983 A | 10/1980 | Steere et al. |

(Continued)

FOREIGN PATENT DOCUMENTS

| DE | 196 16 216 A1 | 10/1997 |
| EP | 0407724 B1 | 9/1993 |

(Continued)

OTHER PUBLICATIONS

Skinner, D. Z. et al., *Segregation and Conditioning Probabilty Association of Molecular Markers With Traits in Autotetraploid Alfalfa* Molecular Breeding, vol. 6 (2000) 295-306.

(Continued)

*Primary Examiner* — David Parsley
*Assistant Examiner* — Danielle Clerkley
(74) *Attorney, Agent, or Firm* — Pioneer Hi-Bred Int'l Inc

(57) ABSTRACT

An automated high throughput apparatus, method and system for seed sampling is provided. The seed sampling system includes an ablation subsystem having a controlled cutting path and a seed handling subsystem comprising a staging system having a plurality of seed staging positions for staging a batch of seed in a sequential manner, and a carrier system for simultaneously presenting seed staging positions at the cutting path for removing a sample portion from each seed in the batch. A method of this invention includes providing ablation means having a controlled cutting path, automatically staging a batch of seed at a plurality of staging positions in a sequential manner, simultaneously presenting the batch of seed at the cutting path, and removing a sample portion from each seed in the batch.

2 Claims, 36 Drawing Sheets

(56) References Cited

U.S. PATENT DOCUMENTS

| | | | |
|---|---|---|---|
| 4,602,716 | A | 7/1986 | Barla-Szabo et al. |
| 5,677,474 | A | 10/1997 | Rogers |
| 6,307,123 | B1 | 10/2001 | Kriz et al. |
| 6,537,826 | B1 | 3/2003 | Horigane |
| 6,705,827 | B2 | 3/2004 | Keller et al. |
| 6,706,989 | B2 | 3/2004 | Hunter et al. |
| 6,809,819 | B1 | 10/2004 | Vinjamoori et al. |
| 6,865,556 | B2 | 3/2005 | Penner et al. |
| 6,959,617 | B2 | 11/2005 | Deppermann |
| 7,044,306 | B2 | 5/2006 | Deppermann et al. |
| 7,067,834 | B2 | 6/2006 | Horigane et al. |
| 7,290,665 | B2 | 11/2007 | Hunter et al. |
| 7,367,155 | B2 | 5/2008 | Kotyk et al. |
| 7,502,113 | B2 | 3/2009 | Deppermann et al. |
| 7,588,151 | B2 | 9/2009 | Hunter et al. |
| 7,591,101 | B2 | 9/2009 | Deppermann |
| 7,591,374 | B2 | 9/2009 | Hunter et al. |
| 7,600,642 | B2 | 10/2009 | Deppermann |
| 7,611,842 | B2 | 11/2009 | Deppermann et al. |
| 7,685,768 | B2 | 3/2010 | Deppermann |
| 7,703,238 | B2 | 4/2010 | Deppermann et al. |
| 7,767,883 | B2 | 8/2010 | Deppermann et al. |
| 7,830,516 | B2 | 11/2010 | Deppermann et al. |
| 7,832,143 | B2 | 11/2010 | Deppermann et al. |
| 7,849,632 | B2 | 12/2010 | Deppermann et al. |
| 7,877,926 | B2 | 2/2011 | Deppermann |
| 7,905,050 | B2 | 3/2011 | Hunter et al. |
| 7,934,600 | B2 | 5/2011 | Deppermann et al. |
| 7,941,969 | B2 | 5/2011 | Deppermann et al. |
| 7,998,669 | B2 | 8/2011 | Deppermann et al. |
| 8,028,469 | B2 | 10/2011 | Deppermann et al. |
| 8,031,910 | B2 | 10/2011 | Jones et al. |
| 8,071,845 | B2 | 12/2011 | Deppermann et al. |
| 8,076,076 | B2 | 12/2011 | Osborn et al. |
| 8,245,439 | B2 | 8/2012 | Deppermann et al. |
| 8,281,935 | B2 | 10/2012 | Deppermann et al. |
| 2002/0108547 | A1 | 8/2002 | Moszoro et al. |
| 2003/0106258 | A1 | 6/2003 | Keller et al. |
| 2004/0267457 | A1 | 12/2004 | Timmis et al. |
| 2006/0042527 | A1 | 3/2006 | Deppermann |
| 2006/0046244 | A1 | 3/2006 | Deppermann |
| 2007/0048872 | A1 | 3/2007 | Deppermann et al. |
| 2007/0207485 | A1 | 9/2007 | Deppermann et al. |
| 2008/0131924 | A1 | 6/2008 | Cope et al. |
| 2008/0317279 | A1 | 12/2008 | Deppermann et al. |
| 2009/0061449 | A1 | 3/2009 | Chung et al. |
| 2009/0119986 | A1 | 5/2009 | Hunter et al. |
| 2009/0155878 | A1 | 6/2009 | Becker et al. |
| 2009/0215060 | A1 | 8/2009 | Deppermann et al. |
| 2010/0044356 | A1 | 2/2010 | Cope |
| 2010/0086963 | A1 | 4/2010 | Deppermann et al. |
| 2010/0299790 | A1 | 11/2010 | Deppermann et al. |
| 2011/0081716 | A1 | 4/2011 | Deppermann |
| 2011/0117570 | A1 | 5/2011 | Cope et al. |
| 2011/0129836 | A1 | 6/2011 | Deppermann et al. |
| 2011/0160068 | A1 | 6/2011 | Becker et al. |
| 2011/0217700 | A1 | 9/2011 | Deppermann et al. |
| 2011/0225680 | A1 | 9/2011 | Cope |
| 2011/0296930 | A1 | 12/2011 | Deppermann et al. |
| 2012/0079629 | A1 | 3/2012 | Deppermann et al. |
| 2012/0180386 | A1 | 7/2012 | Deppermann et al. |

FOREIGN PATENT DOCUMENTS

| | | |
|---|---|---|
| EP | 1 346 206 B1 | 9/2003 |
| EP | 1 391 713 A2 | 2/2004 |
| GB | 2 293 744 A | 4/1996 |
| KR | 10-2000-0022775 | 11/2001 |
| KR | 339689 B | 6/2002 |
| RU | 2187919 C2 | 8/2002 |
| SU | 1805835 A3 | 3/1993 |
| WO | WO 03/084847 A2 | 10/2003 |
| WO | WO 2006/026466 A2 | 3/2006 |
| WO | WO 2006/026467 A2 | 3/2006 |
| WO | WO 2007/025250 A2 | 3/2007 |
| WO | WO 2007/103769 A2 | 9/2007 |
| WO | WO 2007/103786 A2 | 9/2007 |
| WO | WO-2007/103786 A2 | 9/2007 |
| WO | WO 2008/150798 A1 | 12/2008 |
| WO | WO-2008/150798 A1 | 12/2008 |
| WO | WO 2009/032741 A2 | 3/2009 |

OTHER PUBLICATIONS

International Preliminary Report on Patentability and Written Opinion from International Patent Application No. PCT/US2010/062526, dated Jul. 4, 2012.

International Search Report and Written Opinion from International Application No. PCT/US2010/062526, mailed Sep. 27, 2011.

Aitken-Christie, J. et al., *Automation Tissue Culture*, Automation and Environmental Control in Plant tissue Culture (1995) 1-18.

Casady, W. W. et al., *An Automated Kernel Positioning Device for ComputerVision Analysis of Grain*, American Society of Agricultural Engineers, vol. 32(5) (1989) 1821-1826.

Chunwongse, J. et al., *Pre-Germation Genotypic Screening Using PCR Amplification of Half-Seeds*, Theor Appl Genet, 86 (1993) 694-698.

Churchill, D. B. et al., *Rotating Table for Measuring Seed Physical Properties*, Transactions of the ASAE, vol. 34(4) (1991) 1842-1845.

Dekkers, J. C. M. et al., *The Use of Molecular Genetics in the Improvement of Agricultural Populations*, Nature Reviews 1 Genetics, vol. 3, (2002) 22-32.

Gasvoda, D. et al., *Whiteback Pine Seed Scarifier*, United States Department of Agriculture Food Service, Technology & Development Program, Timber Tech Tips, 0224-2332-MTDC (2002) pp. 1-6.

Hahnen, S. et al., *Automated DNA Preparation frm Maize Tissues and Food Samples Suitable for Real-time PCR Detection of Native Genes*, European Food Research Technology vol. 215 (2002) 443-446.

Higley, P.M., et al., *Effects of Non-Destructive Tissue Extraction on the Viability of Corn, Soybean and Bean Seeds*, Seed Sci. & Technol., 22 (1994) 245-252.

Horigane, A. et al., *Evaluation of Color Characteristics of Cross-Sectioned Wheat Kernels*, Food Sci. Technol. Res., 9:4 (2003), 327-331.

Horigane, A. et al., *Measurement of Brightness of Cross-Sectioned Wheat Kernels*, Japanese Journal of Crop Science, vol. 72, (attachment No. 1) (2003) 176-177.

Horigane, A. et al., *Two-Dimensional Analysis of Kernels Using a New Sample Preparation Method*, Chemistry and Biology, vol. 41, No. 6 (2003) 398-402.

Kamiya, M. et al., *Rapid DNA Extraction Method from Soybean Seeds*, Breeding Science 53 (2003) 277-279.

Kang, H.W. et al., *A Rapid DNA Extraction Method for RFLP and PCR Analysis from a Single Dry Seed*, Plant Molecular Biology Reporter, 16:90 (1998) 1pg.

Kerk, N.M. et al., *Laser Capture Microdissection of Cells from Plant Tissues*, Plant Physiology, vol. 132 (2003) 27-35.

Krysan, P., *Ice-Cap. A High-Throughput Method for Capturing Plant Tissue Samples for Genotype Analysis*, Plant Physiology, vol. 135 (2004) 1162-1169.

Liu, W. et al., *Highly Efficient Doubled-Haploid Production in Wheat via Induced Microsphere Embryogenesis*, Crop Science, vol. 42 (2002) 686-692.

McCarthy, P. L. et al., *Rapid Identfication of Transformed Wheat Using a Half-Seed PCR Assay*, BioTechniques 32 (2002) 560-564.

Pearson, T.C. et al., *Reduction of Aflatoxin and Fumonisin Contamination in Yellow Corn by High-Speed Dual-Wavelength Sorting*, Cereal Chem. 81(4), (2004) 490-498.

Peterhansel, C. et al., *Quantitive Detection of Transgenic and Endogenous DNA Sequences in Seeds After Automated DNA Preparation*, Biomed. Eng. Appl. Basis Commun. 16 (2004) 1-6.

Rafalkski, J. A., *Genetic Diagnostics in Plant Breeding: RAPDs. Microsatellites & Machines*, TIG, vol. 9, No. 8 (Aug. 1993) 275-280.

Sangtong, V. et al., *Serial Extraction of Endosperm Drillings (SEED)—A Method for Detecting Transgenes and Proteins in Single Viable Maize Kernels*, Plant Molecular Biology Reporter 19 (2001) 151-158.

(56) References Cited

OTHER PUBLICATIONS

Skinner, D. Z. et al., *Segragation and Conditioning Probability Association of Molecular Markers With Traits in Autotetraploid Alfalfa*Molecular Breading, vol. 5 (2000) 295-306.

Smith, J. S. C. et al., *Genetic Purity and Testing Technologies for Seed Quality: A Company Perspective*, Seed Science Research 8 (1998) 285-293.

Sweeney, P. et al., *Random Amplified Polymorphic DNA Analysis of Dry Turfgrass Seed*, HortScience 31(3), (1996) 400-401.

Turner, N.A., et al., *Sampling and Analysis for Determining Relationship of Calcium Concentration to Bitter Pit in Apple Fruit*, New Zealand Journal of Agricultural Research 20:4 (1977) 525-532.

Von Post, R. et al., *A High-throughput DNA Extraction Method for Barley Seed*, Euphytica, 130 (2003) 255-260.

Wang, G.L., et al., *PCR Amplification from Single Seeds, Facilitating DNA Marker-Assisted Breeding*, Nucleic Acids Research 21(10), (1993) 2527.

Wenxue, Z., et al., *PCR Analysis of Half-Seeds of Cereal Crops and Its Application in Marker-assississted Selection and Breeding*, Chinese Journal of Biotechnology, 12:4 (1997) 249-255.

Xu, Y., *Developing Marker-Assisted Selection Strategies for Breeding Hybrid Rice*, Plant Breeding Review, 23 (2003) 73-174.

Yang, W, et al., *A Preliminary Study of Non-Lethal Specific Sampling of Corn Embryo and Endosperm and Feasibility of Automating the Seed Selection Process Utilizing the Specific Sampling Technique*, Pioneer Hi-Bred (2002) 1-41.

Wang, J. et al., *Identification of Parents of F1 Hybrids Through SSR Profiling of Material and Hybrid Tissue*, Euphytica, vol. 124 (2002) 29-34.

Yao, Y. et al., *Single Kernel Sampling Method for Maize Starch Analysis While Maintaining Kernel Vitality*, Cereal Chem. 79:6 (2002) 757-762.

DuPont CoatingSolutions [online] [retrieved Apr. 4, 2013]. Retrieved from the Internet: <URL: www.ccaiweb.com/PDF/MembersOnly/annualpres08/DuPont CoatingSolutions—Corporate Member Presentation.pdf. (undated) 12 pages.

200 watt CO2 laser from Synrad provides the best cost per delivered watt available in today . . . [online] [retrieved Dec. 18, 2012]. Retrieved from the Internet: <URL: http://www.synrad.com/fseries/f201.htm>. (2011) 2 pages.

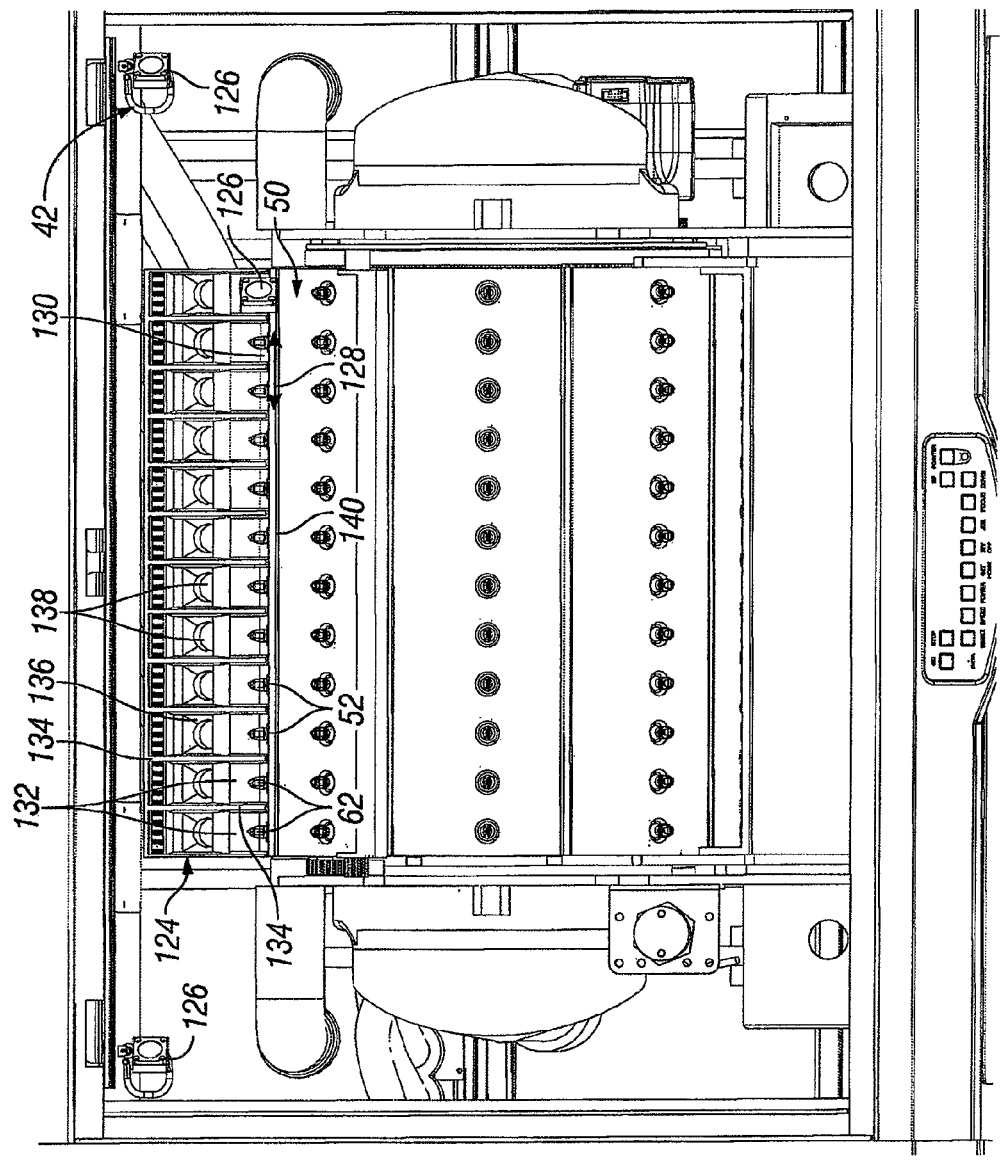

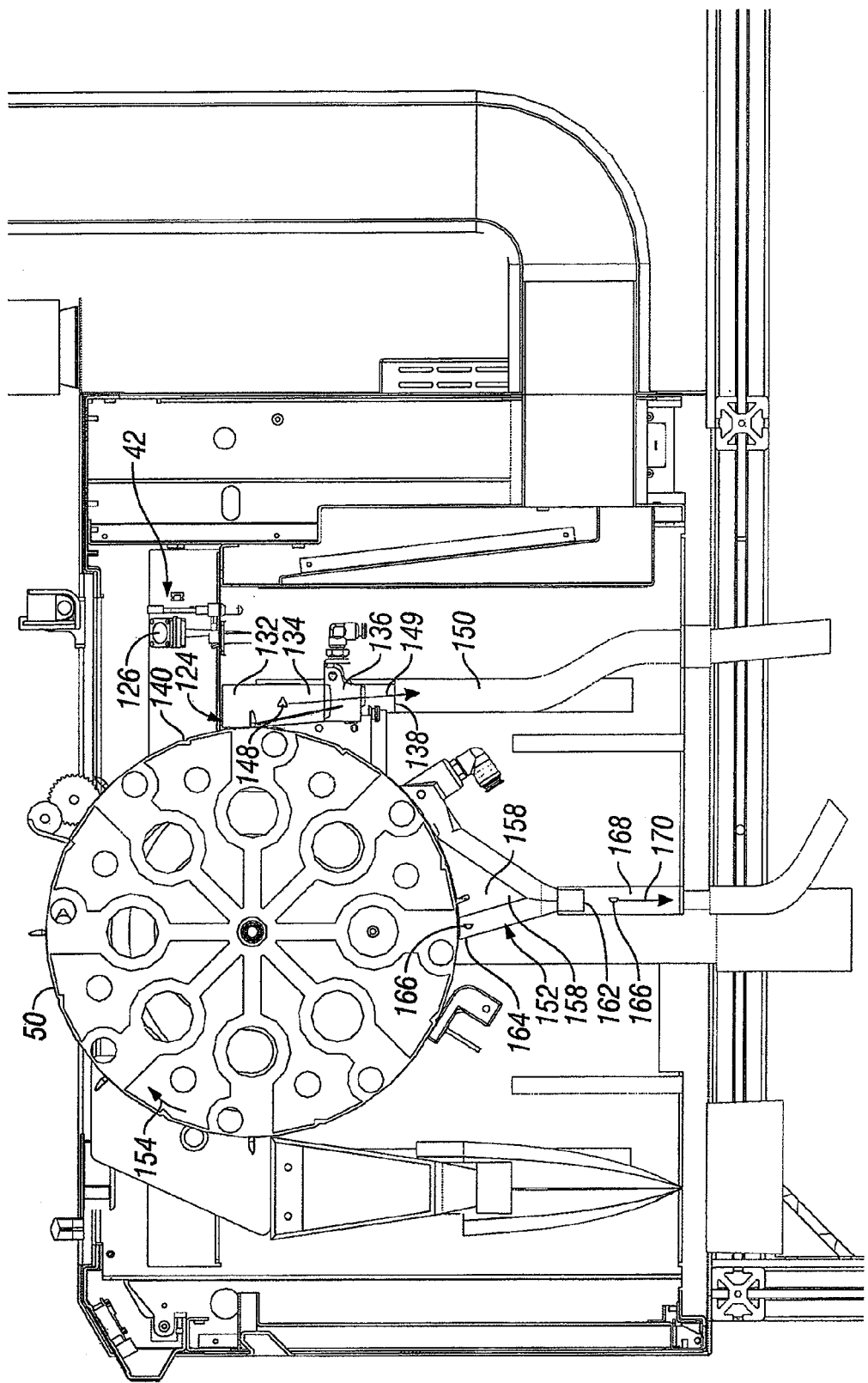

AUTOMATED SEED SAMPLING APPARATUS, METHOD AND SYSTEM

CROSS-REFERENCE TO RELATED APPLICATIONS

The present application claims priority from U.S. Provisional Application No. 61/291,516 filed Dec. 31, 2009, which is hereby incorporated herein by reference in its entirety.

BACKGROUND OF THE INVENTION

1. Field of the Invention

The present invention relates to obtaining tissue samples from individual seed in a high throughput efficient manner.

2. Problems in the Art

It is conventional practice in plant breeding or plant advancement experiments to grow plants from seed of known parentage. The seed are planted in experimental plots, growth chambers, greenhouses, or other growing conditions in which they are either cross-pollinated with other plants of known parentage or self-pollinated. The resulting seed are the offspring of the two parent plants or the self-pollinated plant, and are harvested, processed and planted to continue the plant breeding cycle. Specific laboratory or field-based tests may be performed on the plants, plant tissues, seed or seed tissues, in order to aid in the breeding or advancement selection process.

Generations of plants based on known crosses or self-pollinations are planted and then tested to see if these lines or varieties are moving towards characteristics that are desirable in the marketplace. Examples of desirable traits include, but are not limited to, increased yield, increased homozygoscity, improved or newly conferred resistance and/or tolerance to specific herbicides and/or pests or pathogens, increased oil content, altered starch content, neutraceutical composition, drought tolerance, and specific morphological based trait enhancements.

As can be appreciated and as is well-known in the art, these experiments can be massive in scale. They involve a huge labor force ranging from scientists to field staff to design, plant, maintain, and conduct the experiments, which can involve thousands or tens of thousands of individual plants. They also require substantial land resources. Plots or greenhouses can take up thousands of acres of land. Not only does this tie up large amounts of land for months while the plants germinate, grow, and produce seed, during which time they may be sampled for laboratory or field testing, but then the massive amounts of seed must be individual tagged, harvested, and processed.

A further complication is that much of the experimentation goes for naught. It has been reported in literature that some seed companies discard 80-90% of the plants in any generation early on in the experiment. Thus, much of the land, labor and material resources expended for growing, harvesting, and post-harvesting processing ultimately are wasted for a large percentage of the seed.

Timing pressures are also a factor. Significant advances in plant breeding have put more pressure on seed companies to more quickly advance lines or varieties of plants for more and better traits and characteristics. The plant breeders and associated workers are thus under increasing pressure to more efficiently and effectively process these generations to make more and earlier selections of plants which should be continued into the next generation of breeding.

Therefore, a movement towards early identification of traits of interest through laboratory-based seed testing has emerged. Seed is non-destructively or destructively tested to derive genetic, biochemical or phenotypic information. If traits of interest are identified, the selected seed from specific plants are used either for further experiments and advancement or to produce commercial quantities of seed. Testing seed prevents the need to grow the seed into immature plants, which are then tested. This saves time, space, and effort. If effective, early identification of desirable traits in seed can lead to greatly reducing the amount of land needed for experimental testing, the amount of seed that must be tested, and the amount of time needed to derive the information needed to advance the experiments. For example, instead of thousands of acres of planting and the subsequent handling and processing of all those plants, a fraction of acres and plants might be enough. However, because timing is still important, this is still a substantial task because even such a reduction involves processing, for example, thousands of seed per day.

A conventional method of attempting non-lethal or lethal seed sampling is as follows. Seed of interest is held for example at a sampling station. Blades, teeth or other mechanical means are used to remove a small portion from the seed. The seed portion or debris removed from the seed is collected. The seed portion or debris is transferred to another container for testing. The seed portion or debris is thus collected and ready for laboratory analysis. The existing conventional methods for performing lethal and non-lethal separation of seed tissue are a slow process. Care must be taken in the removing and handling of the seed portion or debris. Containers must then be handled and marked or otherwise tracked and identified. More importantly, the knife, teeth or mechanical means of the device used to remove a small portion of the seed must be cleaned between the sampling of each seed. There can be substantial risks of contamination by carry-over from sample to sample and in handling. Also, many times it is desirable to obtain seed material from a certain physiological tissue of the seed. For example, with corn seed, it may be desirable to take the sample from the endosperm. Or, with soybean seed, it may be desirable to take a sample from the seed opposite or away from the germ. In such cases, it is not trivial, but rather time-consuming and somewhat difficult, to orient the seed in an automated manner so as to be best positioned for removing a portion of the seed from the desired location.

As evidenced by the aforementioned example, present conventional seed analysis methods, such as is used in genetic, biochemical, or phenotypic analysis, require at least a part of the seed to be removed and processed. In removing some seed tissue, various objectives may need to be met. These may include one or more of the following objectives:

Maintain seed viability post-sampling if required.

Obtain at least a minimum required sample amount, without effecting viability.

Obtain a sample from a specific location on the seed, often requiring the ability to orient the seed in a specific position to obtain the sample.

Maintain a particular through-put level for efficiency purposes.

Reduce or virtually eliminate contamination between samples by not using the same tissue removal instrument, blade, teeth or other device to remove samples from multiple seeds.

Allow for tracking of separate samples and their correlation to other samples in a group.

Conventional seed sampling technologies do not address these requirements sufficiently, resulting in pressures on capital and labor resources, and thus illustrate the need for improvement in the state of the art. The current methods are relatively low throughput, have substantial risk of cross-contamination and tend to be inconsistent in the handling, orienting, and removal of a sample from the seed.

Therefore, a need exists in the art for apparatuses, methods and systems providing semi- and fully-automated, high throughput seed sampling.

BRIEF SUMMARY OF THE INVENTION

The present invention relates to an automated, high throughput seed sampler apparatus, method and system. The apparatus, methods and systems of the present invention provide an automated, high throughput seed sampler providing automated non-lethal or lethal sampling and indexing of a batch of seed.

Embodiments of this invention provide for the testing of a batch of seed in an automated and high throughput manner which may be performed prior to planting, reducing the tremendous amount of resources that would ordinarily be used and often wasted in an effort to identify desirable traits in a population of seed.

Generally the apparatus of this invention comprises ablation means having a controlled cutting path and seed handling means. The seed handling means includes seed staging means for staging a batch of seed in a sequential linear manner and seed presentation means for simultaneously presenting seed staging means with a batch of seed at the cutting path for removing a sample portion from each seed in the batch. In a preferred form, the apparatus also comprises a plurality of seed staging positions adapted to orient a batch of seed relative to the ablation means and automated seed retention and release means at the plurality of seed staging positions.

According to a method of this invention, ablation means having a controlled cutting path is provided and steps of automatically staging a batch of seed at a plurality of staging positions in a sequential manner, simultaneously presenting the batch of seed at the cutting path and removing a sample portion from each seed in the batch are performed. In a preferred form, the method also includes the step of automatically retaining and releasing a batch of seed at the plurality of seed staging positions by switching the seed staging positions between a seed retention and release mode.

A system is provided in another aspect of this invention. The high throughput system for automated bulk sampling and indexing of a batch of seed comprises an ablation subsystem having a controlled cutting path and a seed handling subsystem comprising a staging system having a plurality of seed staging positions for staging a batch of seed in a sequential manner and a carrier system for simultaneously presenting the seed staging positions at the cutting path for removing a sample portion from each seed in the batch. In a preferred form, the carrier system is adapted to provide simultaneous movement of a plurality of seed staging positions into the cutting path of the ablation subsystem.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

FIG. 10 is a top plan view of an ablation system and seed collection system according to one aspect of the present invention;

FIG. 11B is sectional view of another exemplary embodiment of an ablation system and seed collection system of this invention;

DETAILED DESCRIPTION

Figure 1A:
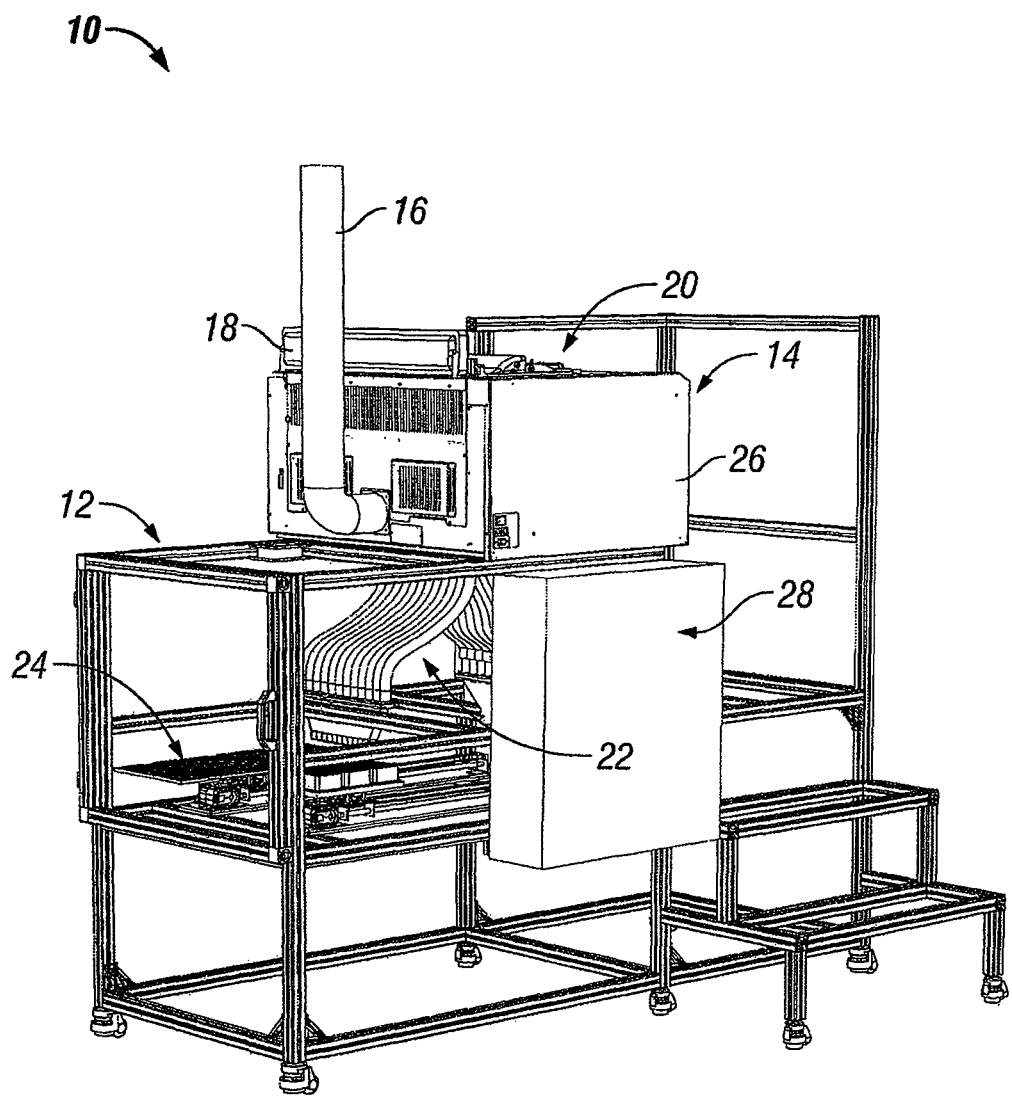
FIG. 1A is a perspective view of one embodiment of a seed sampler system according to principles of the present invention.
Figure 1B:
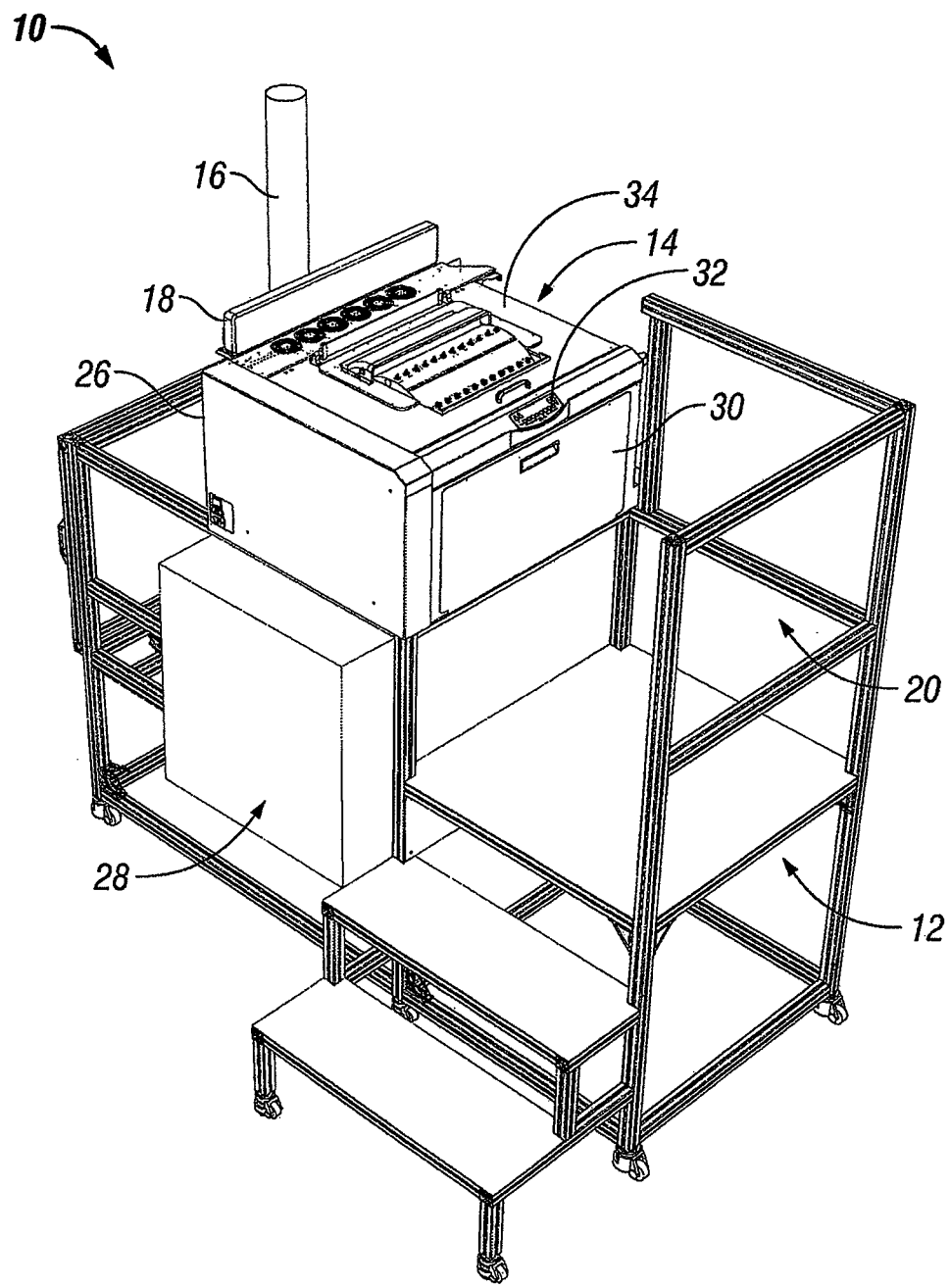
FIG. 1B is another perspective view of the seed sampler system.
Figure 1C:
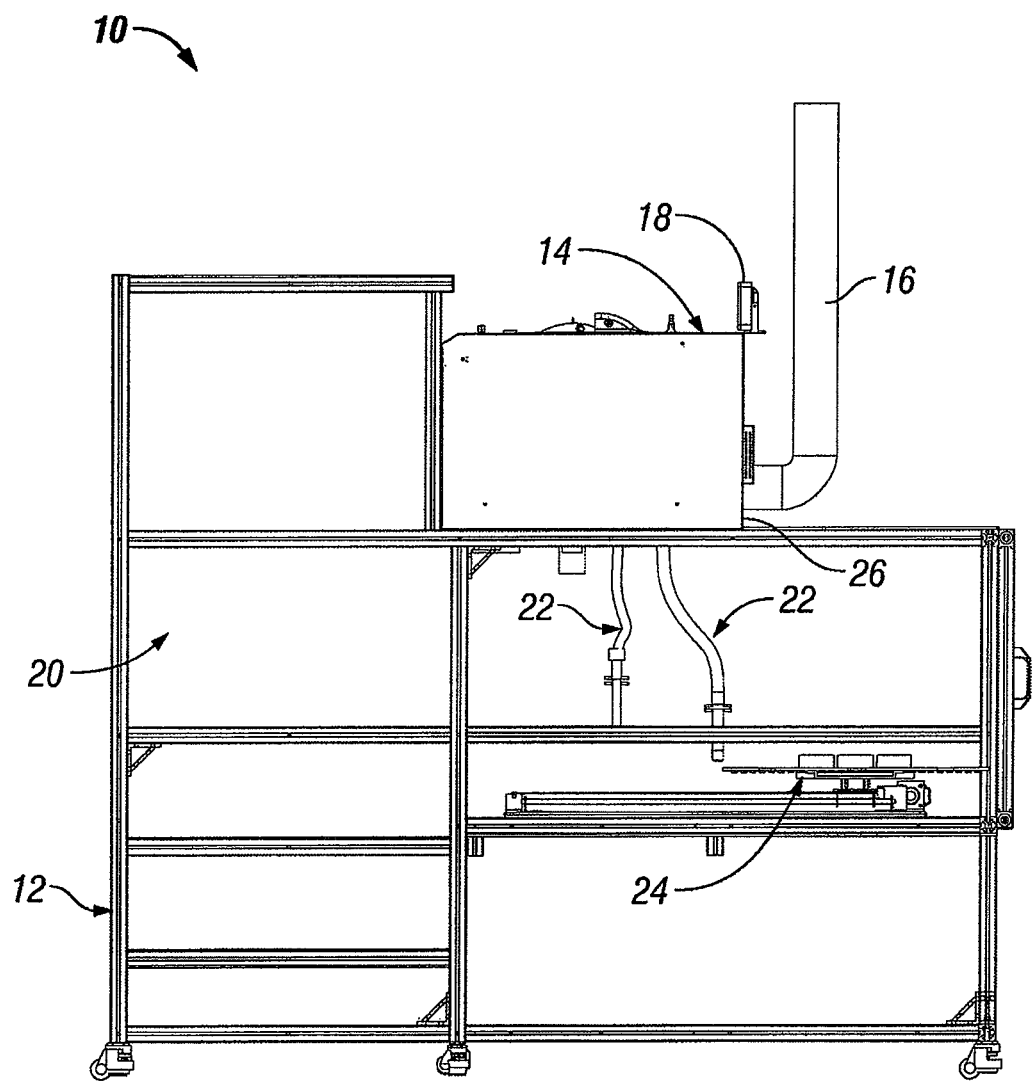
FIG. 1C is a side elevation view of the seed sampler system.
Figure 1D:
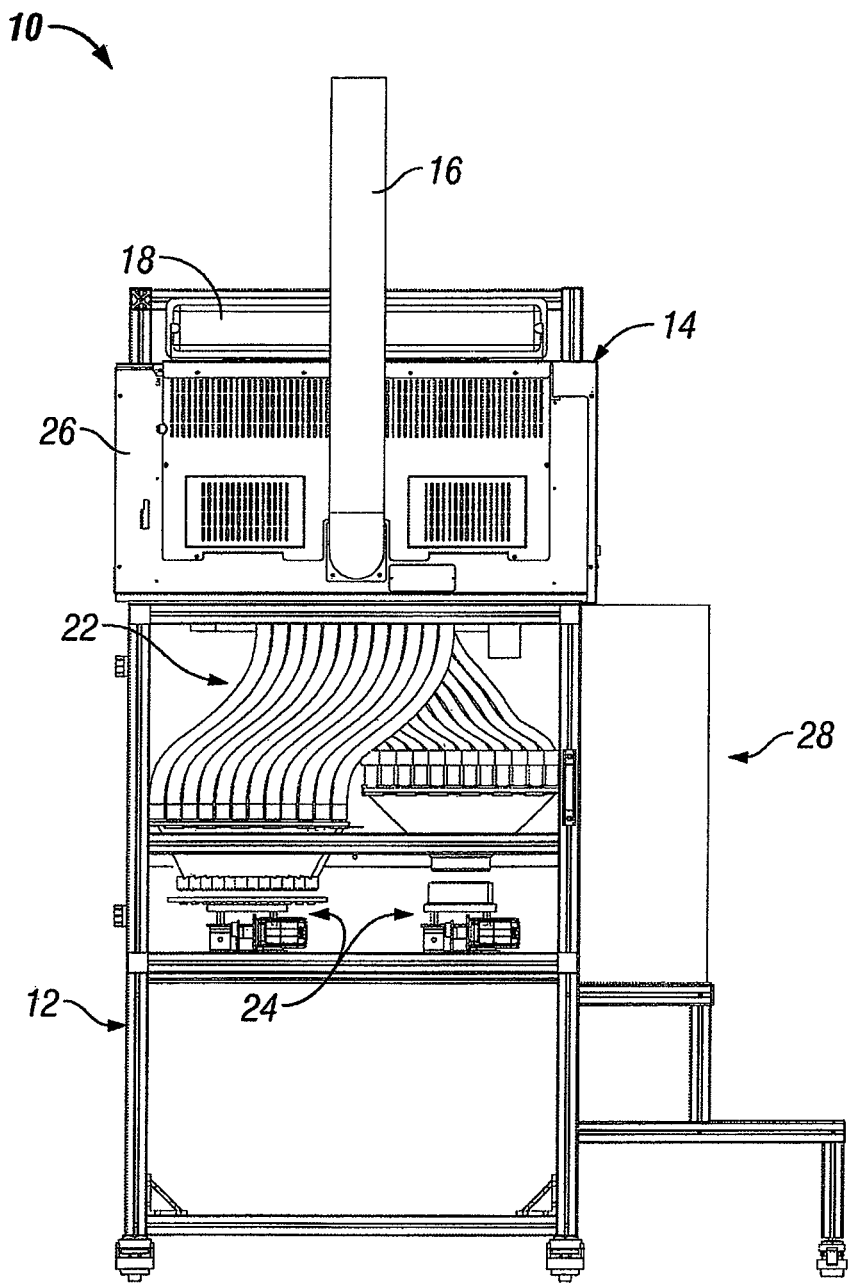
FIG. 1D is a back elevation view of the seed sampler system.
Figure 1E:
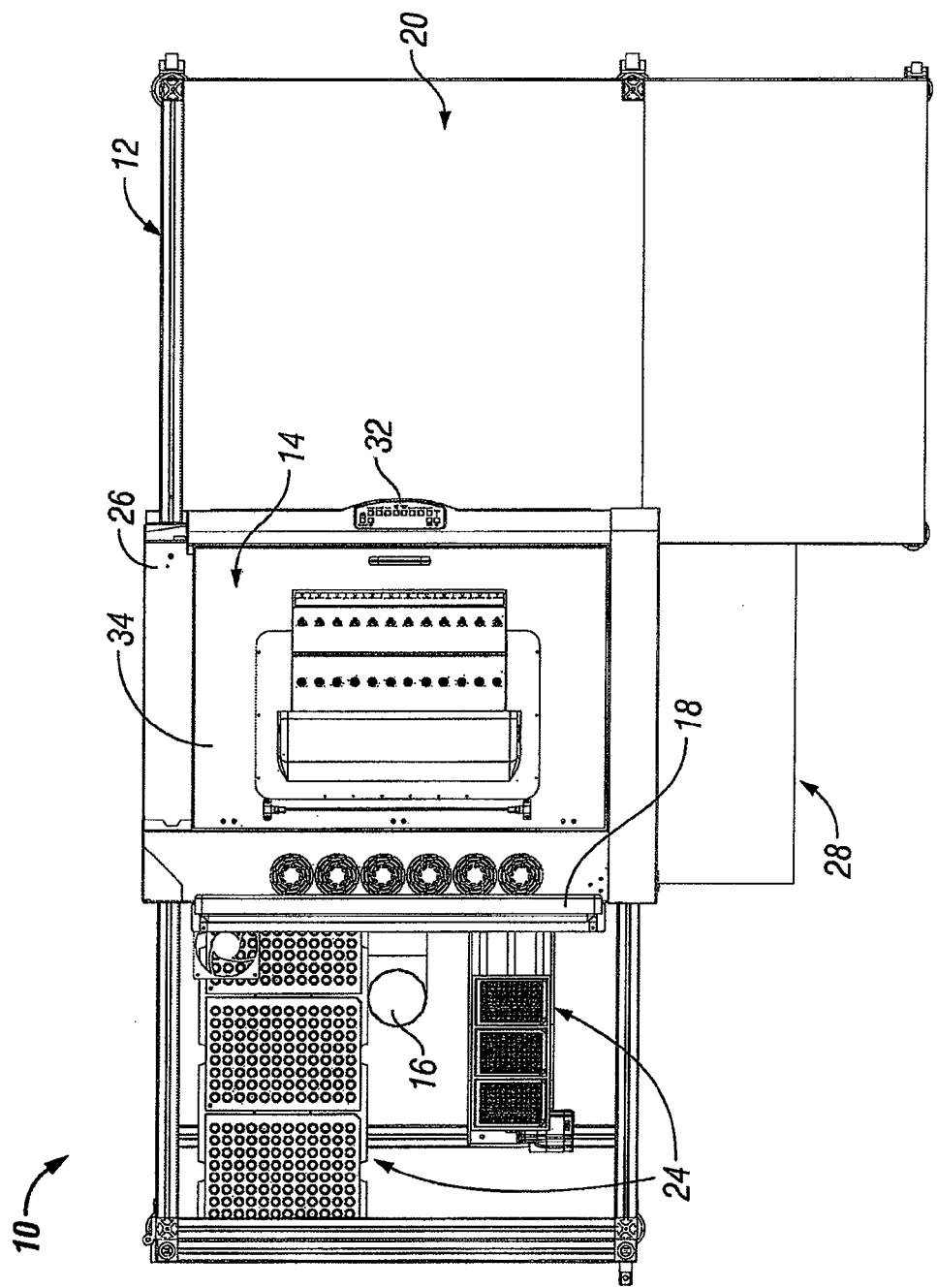
FIG. 1E is a top plan view of the seed sampler system.

The following description is merely exemplary in nature and is not intended to limit the present disclosure, application or uses. For a better understanding of the invention, several exemplary embodiments and/or aspects will now be described in detail. Reference will be taken from time-to-time to the appended drawings. Reference numerals will be used to indicate certain parts and locations throughout the figures unless otherwise indicated.

Apparatus

One embodiment of a high throughput automated seed sampler system according to the principles of the present invention and indicated generally as 10 is illustrated in FIGS. 1A-E. The seed sampler system 10 is configured to self-orient and automatically retain a batch of seed taken from a hopper at staging positions on a seed carrier, simultaneously present the staged seed at a controlled cutting path provided by an ablation means, such as for example a laser, and automatically convey the sampled seed and the sample portion of the seed to separate containers for storing and indexing the sampled seed and the seed portion in their respective containers.

As illustrated in FIGS. 1A-E, the seed sampler system 10 comprises a supporting framework 12. The supporting framework 12 may be constructed of various structural load bearing members, such as for example square tubing assembled to form a supporting frame. The supporting framework 12 may includes casters or wheels on the lower most terminal ends of the vertical or horizontal posts, thereby allowing the supporting framework 12 to be moved. The supporting framework 12 is configured to provide an operator station 20 whereby an operator may position him or herself relative to the seed sampler 14 for controlling, operating and/or observing the system. The supporting framework 12 may also include various platforms and levels allowing an operator to access and/or observe various systems of the invention. The supporting framework 12 is not critical to the invention, nor does the design and layout of the supporting framework 12 play a critical role in the invention. Those skilled in the art can appreciate the supporting framework 12 could take on many various configurations and designs using various parts and subcomponents without departing from the spirit and scope of the present invention.

The seed sampler system 10 includes a seed sampler station 14 supported atop supporting framework 12. The seed sampler station 14 includes a ventilation system 16 for evacuating debris, fumes or other unwanted materials resulting from ablation from within the seed sampler station 14 to a location remote to the seed sampler system 10. Instructions, operational commands and status of the seed sampler station 14 is provided to the operator at the operator station 20 via display panel 18 and control panel 32. The seed sampler station 14 is generally contained within cabinet 26. The interior of cabinet 26 may be accessed through door 30, lid 34 or other removable panels associated with cabinet 26. Through control panel 32 an operator may input control parameters or provide instructions to seed sampler station 14 and via display panel 18 the operator may be apprized of the current operating parameters or status of seed sampler station 14. A control box 28 attached to supporting framework 12 houses the necessary electrical components, wiring and networking devices for supporting operation of seed sampler station 14. Electrical or other energy potential sources, whether pneumatic or otherwise, may be connected to control box 28 for providing various forms of energy potential, such as electrical and pneumatic, to seed sampler station 14.

In addition to seed sampler station 14, seed sampler system 10 includes a seed collection system 22 and a seed storage system 24. Instructions from an operator provided at control panel 32 may also be used to control operation, whether dependent on or independent of seed sampler station 14, of the seed collection system 22 and seed storage system 24. Devices and components for controlling and operating seed collection system 22 and seed storage system 24 may be networked and configured through control box 28 and/or control panel 32 of seed sampler station 14. For example, a computer or other controller may be connected to system 10 using control box 28 for monitoring, operating, testing, troubleshooting and/or programming purposes.

Figure 2:
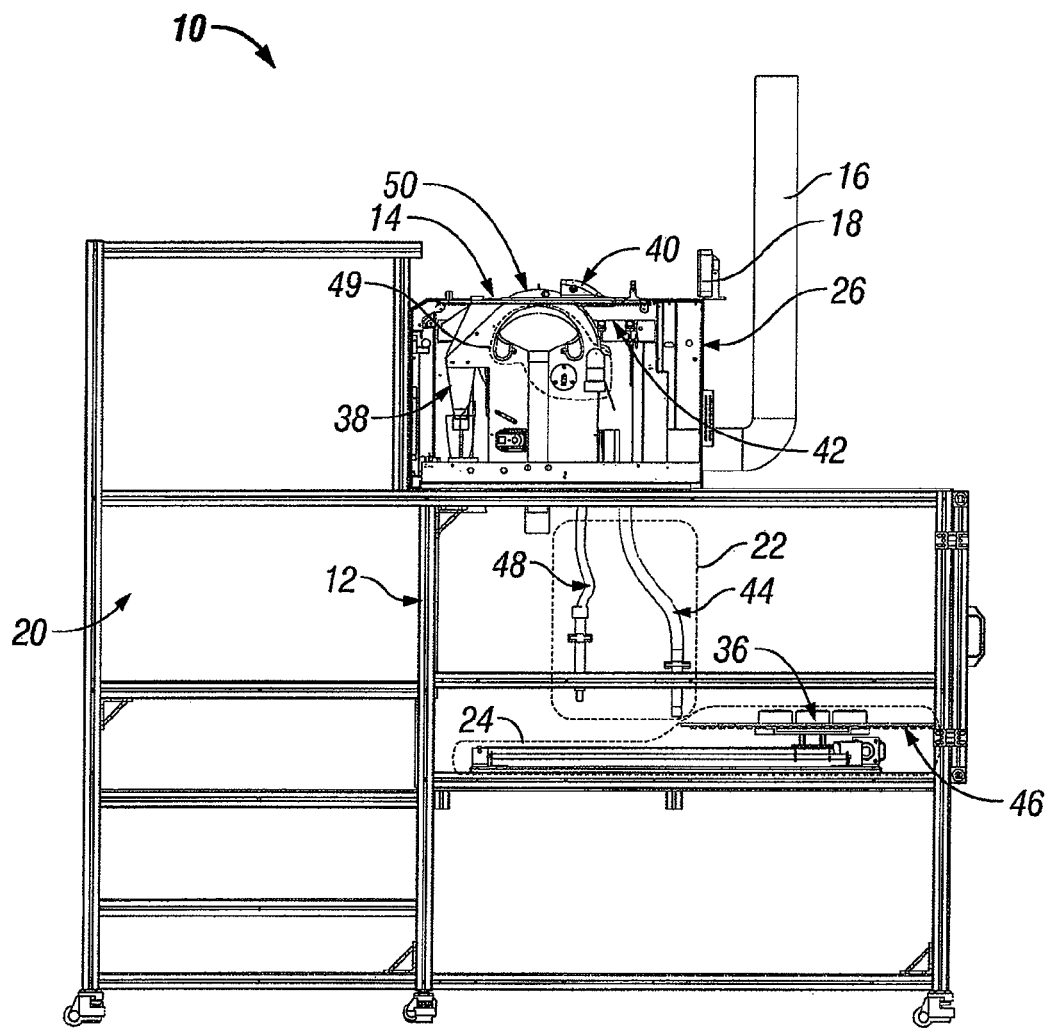
FIG. 2 is a side elevation view of the seed sampler system with exterior panels hidden from view to illustrate various components.

FIG. 2 is a side elevation view of the seed sampler system 10 whereby side panels ordinarily obstructing view to one or more systems or components are hidden from view to allow illustration of the seed sampler station 14, seed collection system 22, seed storage system 24 and other various components and systems of the seed sampler system 10. As is further illustrated in FIG. 2, the seed sampler system 10 includes a seed carrier 50 that is configured to rotate at least partially within cabinet 26 of seed sampler station 14. Seed sampler station 14 also includes a seed distribution system in communication with seed carrier 50 for providing a source of a batch or batches of seed for pickup by seed carrier 50. Also configured in operable communication with seed sampler station 14, and particularly seed carrier 50, is a pneumatic system 49 for communicating pneumatic potential to seed carrier 50 whether negative or positive potential. The seed sampler station 14 also includes an ablation enclosure system 40 in operable communication with seed carrier 50 to provide separation between the operator and the ablation system 42 when in operation. Within cabinet 26 and in operable position adjacent seed carrier 50 is an ablation system 42. The ablation system 42 is configured to separate a portion from each seed consistent with the principles and objectives of this invention. The ventilation system 16 evacuates fumes, debris and other materials resulting from the ablation system 42 that may affect operation of seed sampler station 14, be undesirable to have contained within a small work environment such as cabinet 26, or that may be undesirable to expose the operator to. The ventilation system 16 could be filtered and ported to an outside or ambient environment away from seed sampler system 10.

The seed sampler system 10 also includes a seed collection system 22 configured to be in operable communication with ablation system 42 whereby sampled seed and seed portions separated from each sampled seed are communicated and handled through a respective sampled seed distribution system 44 and seed portion distribution system 48. Sampled seed and seed portions are collected and stored using the seed storage system 24. Respective portions of the seed, including the sampled seed and the sampled seed portion are contained and stored respectively in a seed portion storage system 36 and sampled seed storage system 46. The aforementioned systems of seed sampler system 10 will be described in more detail below.

Figure 3A:
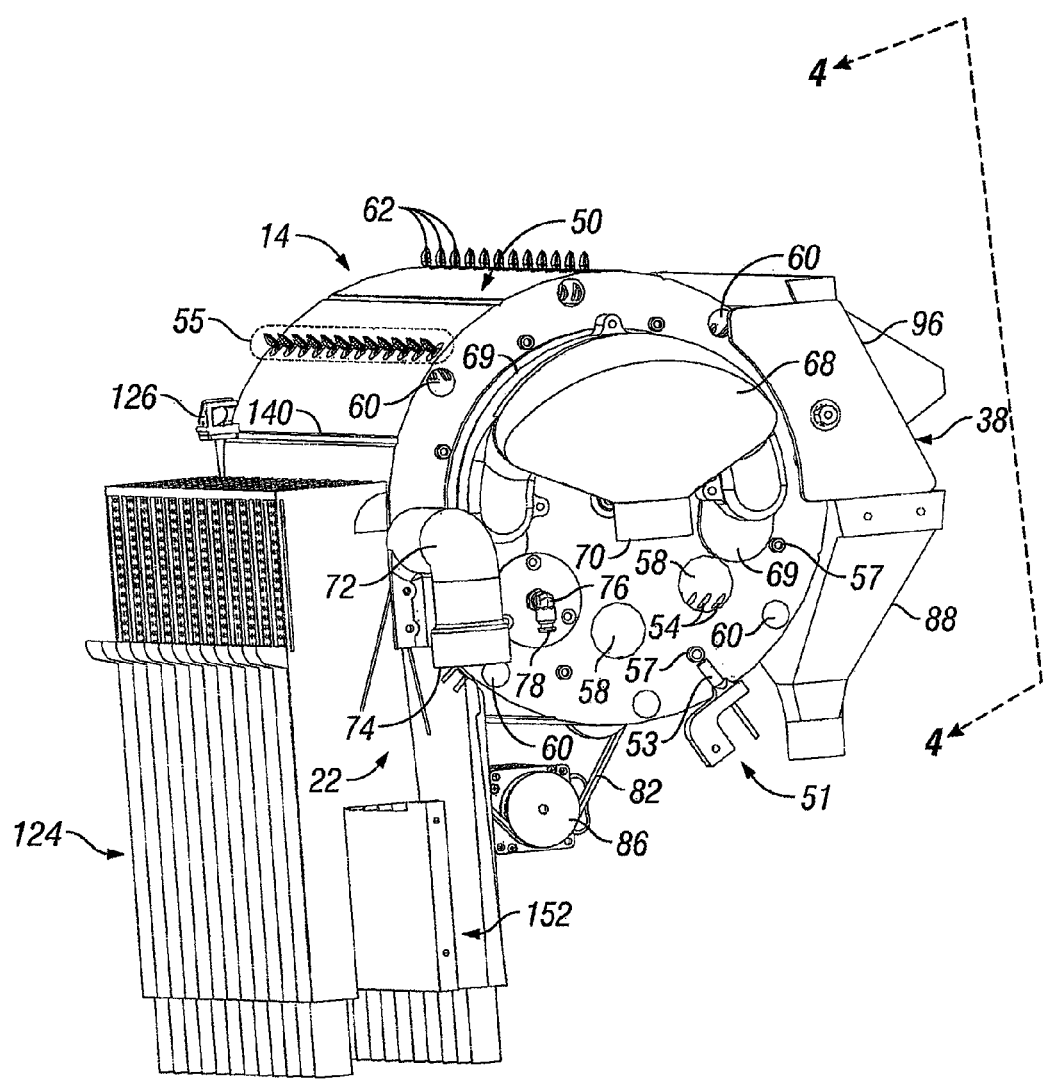
FIG. 3A is an enlarged perspective view of the seed sampler system with exterior panels hidden from view to illustrate various components.
Figure 3B:
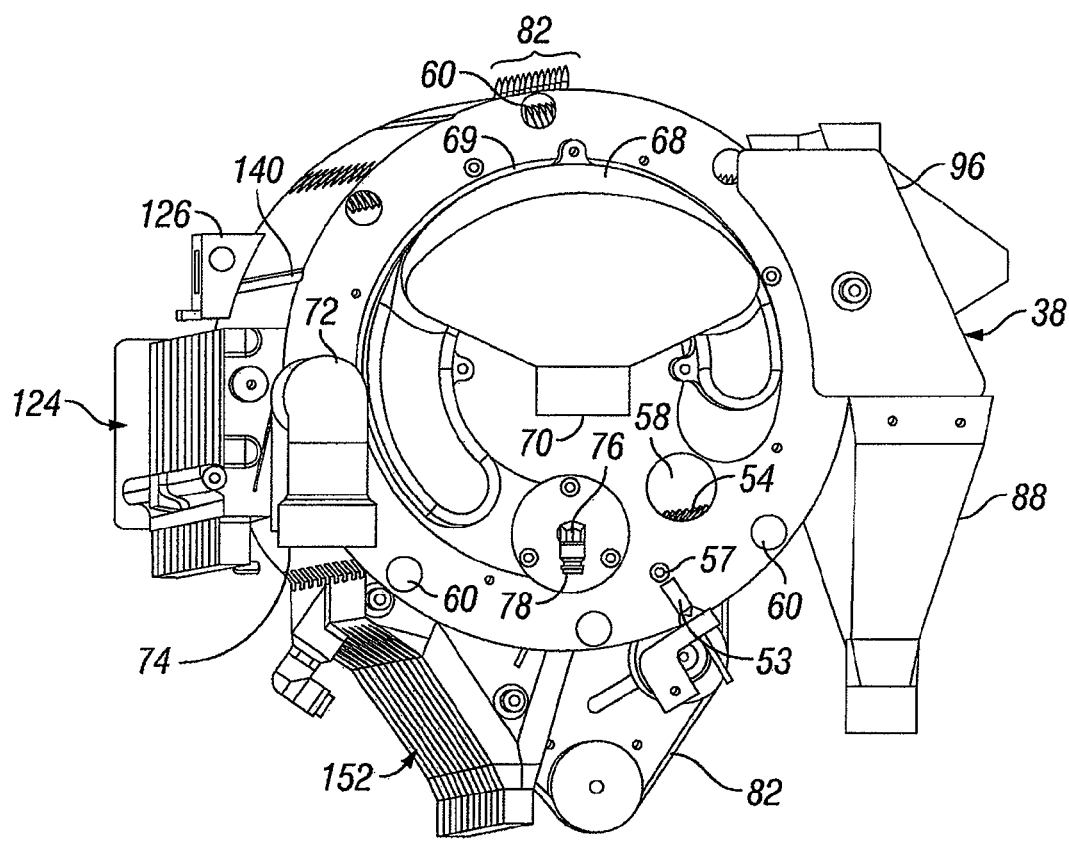
FIG. 3B is a perspective view of another embodiment of the seed sampler system with exterior panels hidden from view to illustrate various components.
Figure 4:
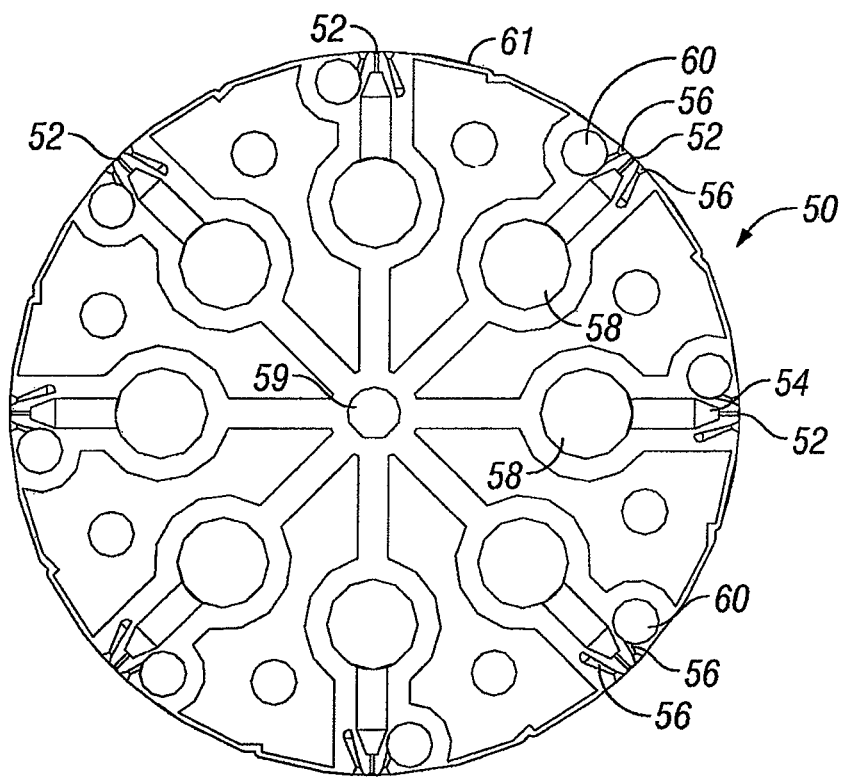
FIG. 4 is a sectional view of the seed carrier taken along line 4-4 in FIG. 3A.
Figure 5:
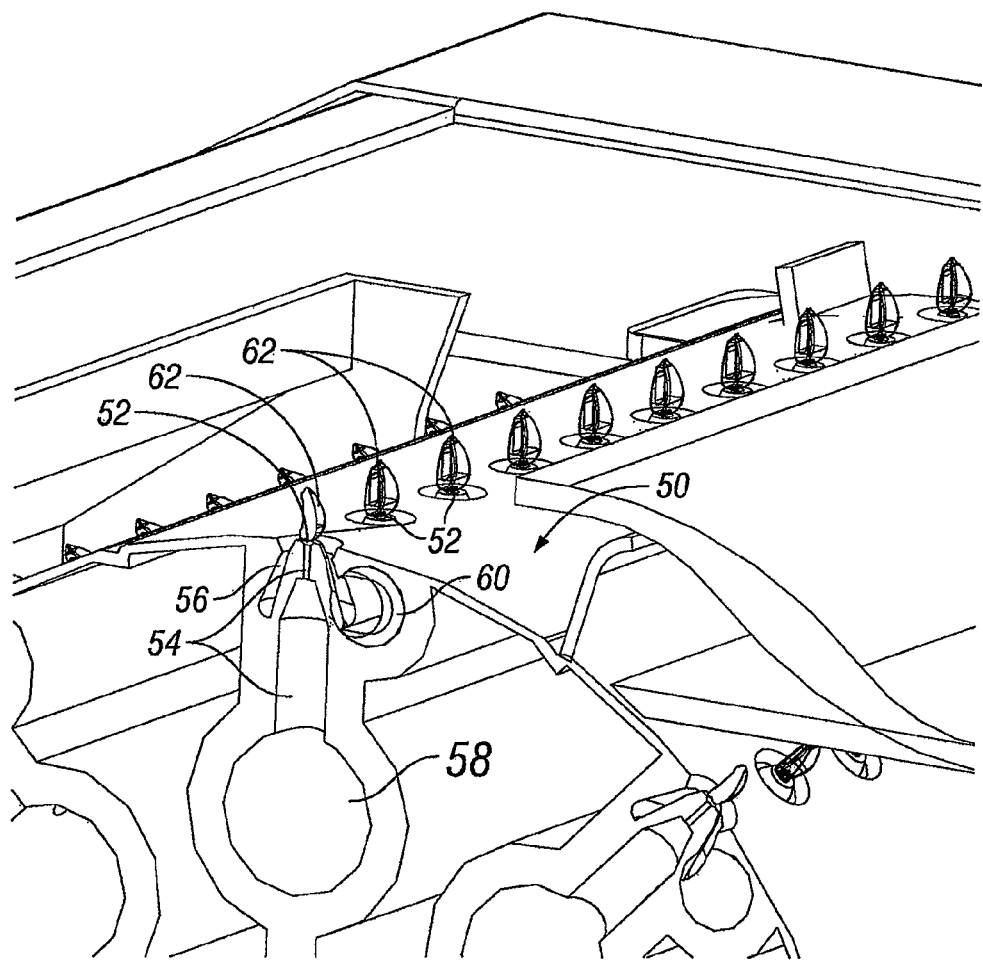
FIG. 5 is an enlarged perspective view of the seed carrier shown in FIG. 4.

FIG. 3A-B are enlarged perspective views of embodiments of seed sampler station 14. Panels and other structural supporting members that would otherwise impede illustration and observation are hidden for the purpose of illustrating various systems and components. Not all systems of the seed sampler station 14 are illustrated in FIG. 3A-B, but those shown will be described in detail below. In one aspect of this invention, the seed sampler station 14 shown in FIG. 3A-B include a seed carrier 50 rotatably supported within cabinet 26. Movement may be imparted to seed carrier 50 by one or more motors. For example, in one aspect of this invention the outer peripheral surface 61 of seed carrier 50 is configured to rotate. In one aspect of this invention, a portion of the outer peripheral surface 61 of seed carrier 50 rotates outside of cabinet 26, as illustrated in FIG. 4, to allow the operator to view and manipulate seed positioned at a row of seed staging positions 55. Rotation of seed carrier 50 is provided in at least one aspect of this invention by a motor/pulley system 86 driving belt 82 operably configured around a portion of seed carrier 50 for imparting rotation to seed carrier 50. Other configurations, such as a direct drive or pneumatic drive, are contemplated.

The radial position of seed carrier 50 may be monitored by a seed carrier position sensing system 51. The seed carrier position sensing system 51 preferably includes an electronic sensor, but may include a mechanical sensor, for determining the radial position of seed carrier 50 relative to one or more systems, devices or components of the seed sampler system 10. For example, in a preferred aspect of this invention, seed carrier position sensing system 51 is utilized to determine and monitor the position of a row of seed staging positions 55 (See FIG. 3A-B), lateral seat 140 in the outer peripheral surface 61, or a lateral ports 58 or 60. Sensor 53 could be a photoelectric sensor, an ultrasonic or radar type sensor, or any other type of sensor capable of detecting a sensor element 57 positioned on and rotating with seed carrier 50. Other means for determining and monitoring the position of seed carrier 50 are also contemplated, such as for example, a servo-motor 86 wherein the position of the seed carrier 50 is determined relative to a home or other known position of the motor. The seed carrier position sensing system 51 is configured whereby sensor elements 57 positioned on seed carrier 50 correlate with desired stopping or home positions of seed carrier 50 whereby features such as lateral seat 140 on seed carrier 50 are positioned with respect to other components or devices of the seed sampler station 14 to allow for coordinated rotation of seed carrier 50 relative to other components or subsystems used in conjunction or operated in conjunction with seed carrier 50. Seed carrier 50 may be rotated clockwise or counterclockwise from motor imparted rotation; the beginning and desired ending radial position of seed carrier 50 may be monitored and controlled from input received from seed carrier position sensing system 51. For example, a row of seed staging positions 55 may be moved into the ablation pathway associated with the ablation system 42 by coordinating the radial position of a row of seed staging positions 55 on seed carrier 50 with the radians or degrees of rotation imparted by motor 86. Sensor elements 57 may be aligned with one or more desirable stopping positions of seed carrier 50 whether to position a row of seed staging positions 55 at the seed distribution system 38, ablation system 42, sampled seed distribution system 44 or seed portion distribution system 48.

Also designed in operable communication with seed carrier 50 is a pneumatic system 49. The pneumatic system 49 includes one or more manifolds in communication with seed carrier 50, as best illustrated in both FIGS. 3A-B. Pneumatic system 49 comprises a negative pressure manifold 68 having an outlet in communication with a negative pressure source (not shown). The negative pressure manifold 68 is in operable communication with ports (lateral port 58 in communication with seed staging ports 54) within seed carrier 50 that will be discussed in more detail below. A gasket 69 seals negative pressure manifold 68 to a terminal end of seed carrier 50. Pneumatic system 49 also comprises a positive pressure manifold 72 in operable communication with ports (lateral positive pressure port 60) within seed carrier 50 that will be described in more detail below. Positive pressure manifold 72 includes an inlet 74 in communication with a positive pressure source (not shown). Pneumatic system 49 may also comprise a positive pressure manifold 76 in operable communication with a lateral supply line 58 within seed carrier 50 that will be discussed in more detail below. Positive pressure manifold 76 has an inlet 78 configured to be in communication with a positive pressure source (not shown).

FIG. 3A-B illustrate embodiments of a seed collection system 22 of this invention. The seed collection system 22 illustrated in FIG. 3A is one embodiment or configuration for a seed collection system and provides the utility for collecting singulated sampled seed 148 and sample portions 166 of seed resulting from the ablation process. Specifically, the seed collection system 22 shown in FIG. 3A includes a sampled seed collection manifold 124 for separately collecting sampled seed 148 and a sample portion collection manifold 152 for separately collecting sample portions 166 of seed. Sampled seed collection manifold 152 and/or sample portion collection manifold 152 may include a pneumatic system to assist in moving sampled seed 148 and sample portions 166 of seed through each manifold. The sampled seed collection manifold 124 and sample portion collection manifold 152 may be staged about the outer peripheral surface 61 adjacent one another as shown in FIG. 3A or at separated positions, such as illustrated in FIG. 3B.

The seed sampler station 14 also includes a seed distribution system 38 configured to store a batch or batches of seed adjacent the outer peripheral surface 61 of seed carrier 50. The seed distribution system 38 includes generally a seed distributor 96 and a funnel 88. The seed distributor 96 is configured to move a batch or batches of seed into a collection area 104 adjacent the outer peripheral surface 61 of seed carrier 50 for being picked up by seed staging positions 52 on seed carrier 50 as will be described in more detail below. Leftover seed in seed distributor 96 may be dumped from seed distributor 96 into funnel 88 for collecting.

FIG. 4A is a sectional view of seed carrier 50 taken along line 4A-4A in FIG. 3A. The features of seed carrier 50 shown in FIG. 4A will be discussed in relation to the various systems illustrated in FIG. 3A to better understand the relationship between the systems illustrated in FIG. 3A and the various features of the seed carrier 50 illustrated in FIG. 4A. In one exemplary aspect of this invention, seed carrier 50 comprises a generally round outer peripheral surface 61 and may be likened in geometrical shape to that of a barrel. Seed carrier 50 may be rotatably supported by interior hub 59 or outer peripheral surface 61 of seed carrier 50. In a preferred form, seed carrier 50 includes seed staging positions 52 staggered in a linear configuration, such as in rows 55, across the outer peripheral surface 61 of seed carrier 50. Seed staging positions 52 will be described in more detail below. Each seed staging position 52 comprises a seed staging port 54 that is in communication with the seed staging position 52 and a lateral port 58. Positive or negative pneumatic pressure fields may be communicated through lateral port 58 and seed staging port 54 to retain and release a seed or seed portion from seed staging position 52. A number of the lateral ports 58 are in communication with negative pressure manifold 68 at any one given time. When lateral ports 58 are in communication with negative pressure manifold 68 seed staging positions 52 are in a seed retention mode whereby negative pressure or vacuum is communicated to the seed staging port for retaining a seed at each seed staging position 52 in communication with negative pressure manifold 68. Lateral ports 58 when not in communication with negative pressure manifold 68 or positive pressure manifold 76 operate at ambient air pressure. In one embodiment of this invention, seed carrier 50 is configured whereby seed staging positions 52 residing within a 180 degrees of the outer peripheral surface 61 of seed carrier 50 are in communication with negative pressure manifold 68 whereby each seed staging position 52 is exposed to a negative pressure field for retaining a seed at each seed staging position 52 within the 180 degrees of the outer peripheral surface 61 of seed carrier 50. Those skilled in the art can appreciate that the number of lateral ports 58 in communication at one time with negative pressure manifold 68 can be altered depending on the desired design of seed carrier 50. For example, if it is desirable to have seed picked up and carried 270 degrees of rotation, the negative pressure manifold 68 may be configured whereby lateral ports associated with 270 degrees of rotation of the outer peripheral surface 61 of seed carrier 50 are in communication with the negative pressure manifold 68 to supply negative pressure or vacuum to each of the seed staging ports within the 270 degrees of outer peripheral surface of seed carrier 50. A preferred form of this invention comprises negative pressure manifold 68 designed so that lateral port 58 rotating into the negative pressure manifold 68 and lateral ports 58 rotating out of the negative pressure manifold 68 are coincident with the same plane. Thus, lateral port 58 rotating into vacuum communication with negative pressure manifold 68 retain a seed at each seed staging position 52 in a row 55 in communication with the lateral port 58; seed are picked up from seed distribution system 38 at collection area 104 (shown in FIG. 8C) contiguous with the aforementioned plane. Conversely, another lateral port 58 in communication with a row of seed staging positions 55 at the ablation system 42 are rotating out of the negative pressure manifold 68, after ablation occurs, whereby vacuum supplied to seed staging ports 54 in communication with each seed staging position 52 in the row 55 is cut so that the sample portion 166 may be released from each seed staging position 52. The row of seed staging positions 55 rotating out of the negative pressure manifold 68, in one exemplary embodiment of this invention, are coincident with the aforementioned plane. Therefore, seed picked up at the seed distribution system 38 by a row of seed staging positions 55 is carried by seed staging positions 52 and rotated 180 degrees from seed distribution system 38 to ablation system 42; this whole time, the lateral port 58 in communication with the aforementioned row of seed staging positions 55 are under vacuum or negative pressure from being in communication with negative pressure manifold 68. According to this embodiment, when lateral ports 58 are in communication with negative pressure manifold 68 they bring the corresponding seed staging positions 52 into communication with negative pressure manifold 68 for retaining seed at the row of seed staging positions 55 until the associated lateral port 58 rotates out of the negative pressure manifold 68.

One embodiment of this invention comprises seed carrier 50 configured so that as a lateral port 58 rotates out of negative pressure manifold 68 it immediately rotates into communication with a positive pressure manifold 76 whereby positive pneumatic pressure is communicated through lateral port 58 to provide positive pneumatic pressure to each of the seed staging positions 52 in a row 55. When a lateral port 58 is in communication with positive pressure manifold 76, the corresponding seed staging positions 52 in the row 55 are in a sample portion release mode whereby sample portions 166 of seed being retained at each of the seed staging positions 52 in row 55 are under positive pneumatic pressure from the positive pressure manifold 76. The switching of a row of seed staging positions 55 from negative pressure to positive pressure forces or kicks off the sample portions 166 of seed in a row 55 from the seed staging positions 52 to be collected in a sample portion collection manifold 152.

According to another aspect of this invention, seed carrier 50 comprises a lateral positive pressure port 60 in communication with a positive pressure port 56 that vents at the outer peripheral surface 61 of seed carrier 50 at each seed staging position 52 in a single row 55. Thus, as the seed carrier 50 rotates a row 55 of seed into the ablation system 42 for separating a portion from each seed, the lateral positive pressure port 60 is rotated into communication with positive pressure manifold 76. The air exiting through the positive pressure port 56 during ablation helps disperse any dust, debris, smoke or other material resulting from ablation that would otherwise disrupt ablation, impair efficiency of the laser ablation device 126, impede an operator's visual inspection of the process, or present a health concern to the operator or occupants within a closed environment. As the lateral positive pressure port 60 rotates out of communication with the positive pressure manifold 76, the lateral positive pressure port is open to ambient pressure. Those skilled in the art can appreciate that the timing for when the lateral port 58 and lateral positive pressure port 60 are in communication with positive and negative pressure manifolds can be configured to control the timing for whether a seed is retained or released at each seed staging position 52 in a row 55.

FIG. 5 is an enlarged perspective view of seed carrier 50 and specifically lateral port 58 in communication with seed staging port 54 and seed staging position 52. Each lateral port 58 is in communication with each seed staging position 52 in a row of seed staging positions 55. Thus, each row of seed staging positions 55 is associated with or in communication with a respective lateral port 58 in seed carrier 50. Negative pressure or vacuum introduced through negative pressure manifold 68 into lateral port 58 is communicated through seed staging port 54 to a seed staging position 52 within a row 55. When a row of seed staging positions 55 enters the seed distribution system 38, the lateral port 58 corresponding or associated with the aforementioned row 55 is rotated into communication with negative pressure manifold 68 whereby negative pressure is communicated through lateral port 58 to put each one of the seed staging positions 52 within that row 55 in a seed retention mode. Seed picked up by a row of seed staging positions 55 is carried under vacuum pressure by negative pressure manifold 68 to the ablation system 42 by rotating seed carrier 50. When a lateral port 58 associated with a row of seed staging positions 55 rotates into communication with positive pressure manifold 76, a burst of air travels through lateral port 58 and seed staging port 54 in communication with a seed staging position 52 within a row 55, thereby causing the sample portions 166 of seed in a row 55 to be kicked-off or released from the seed staging position 52; the sample portions 166 of seed kicked-off or released from the row of seed staging positions 55 are collected and communicated to a seed storage system 22 via a sample portion collection manifold 152.

In one aspect of this invention, each seed staging position 52 is positioned atop a conical geometry forming the seed staging position 52; each seed staging position 52 is surrounded in part or entirely by a positive pressure port 56. Positive pressure port 56 is in communication with lateral positive pressure port 60 whereby a positive pressure field is communicated through lateral positive pressure port 60 into a positive pressure port 56 associated with a seed staging position 52.

Figure 6A:
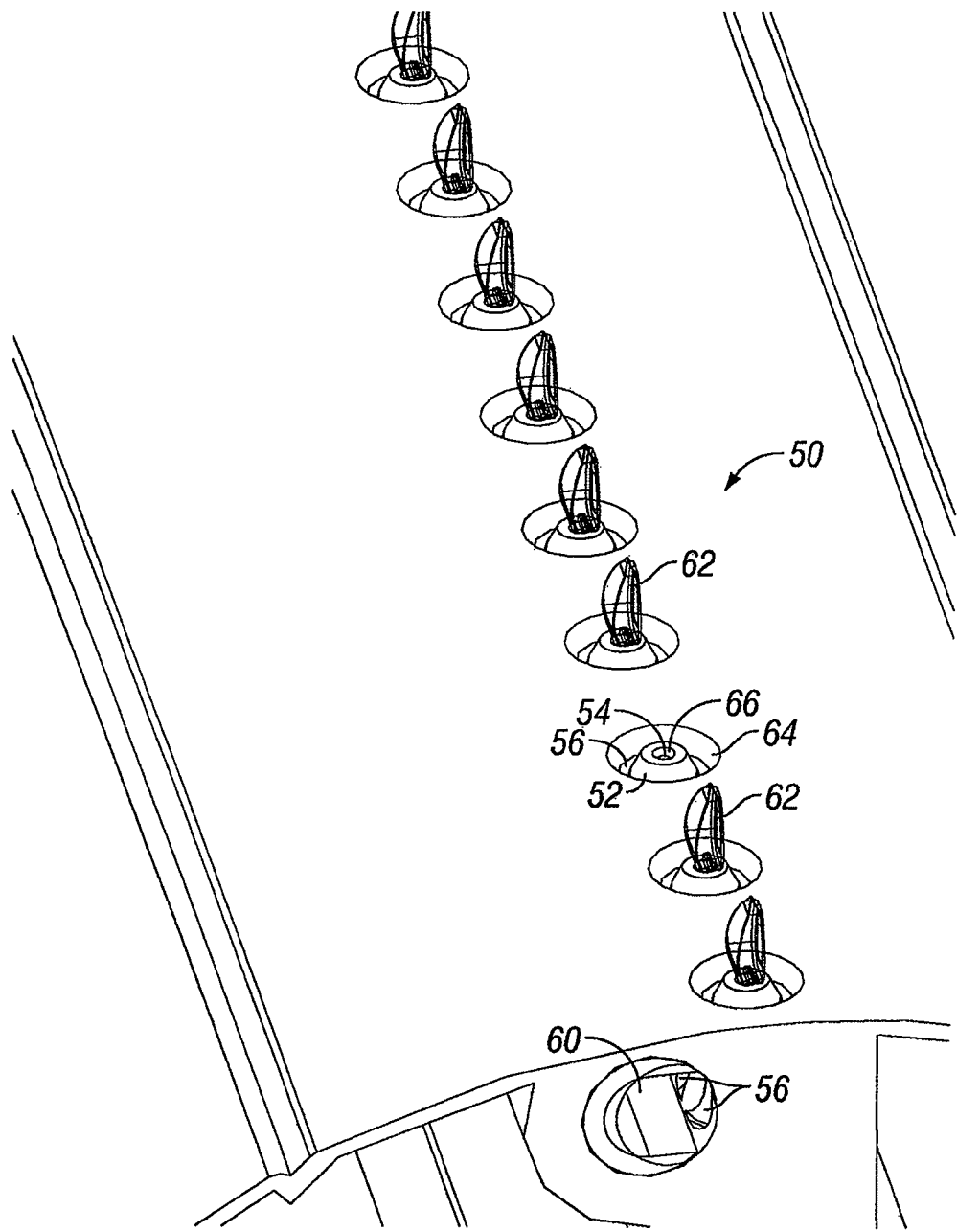
FIG. 6A is an enlarged perspective view of a seed staging position of the seed carrier according to one aspect of the invention.

FIG. 6A is an enlarged perspective view of a seed staging position 52. In a preferred aspect of this invention, seed staging ports 54 are positioned sequentially in a row 55 across the outer peripheral surface 61 of seed carrier 50. Other embodiments of this invention contemplate alternative configurations for seed staging positions 52 on the outer peripheral surface 61 of seed carrier 50. For example, seed staging positions 52 could be spaced along the outer peripheral surface 62 of seed carrier 50 so that each row forms a zigzag pattern or a spiral pattern across the outer peripheral surface 61 of seed carrier 50. Seed staging positions 52 comprise a recess at the terminal end of the conical geometry whereby at least a portion of a seed 62 is allowed to recess itself within recess 64 to better grip the seed, to maintain a desired orientation of each seed and to ensure that each seed remains at the seed staging position 54. Recess 66 within seed staging position 52 is in communication with seed staging port 54 whereby a positive or negative pressure field may be communicated from a negative or positive pressure source (not shown) to recess 66. Recess 64 is in communication with lateral positive pressure port 60 whereby a positive pressure field may be communicated from a positive pressure source (not shown) through lateral positive pressure port 60 to recess 64. As previously mentioned, when a negative pressure field is communicated to seed staging position 52, a seed 62 is retained at seed staging position 52. Conversely, when a positive pressure field is communicated to seed staging position 52 the remaining seed portion 166 (post ablation) is kicked-off or released from seed staging position 52. During ablation, lateral positive pressure port 60 is in communication with positive pressure manifold 72 whereby a positive pressure field is communicated from a positive pressure source (not shown) through positive pressure manifold 72 and lateral positive pressure port 60 thereby exhausting air through positive pressure port 56 and recess 64. The air passing through positive pressure port 56 and recess 64 helps to draw away and dispense smoke, debris and other material resulting from ablation of seed 62. Air exiting recess 64 through positive pressure port 56 also aids in moving smoke, debris and other material resulting from ablation to the ventilation system 16. Quickly removing smoke, debris or other material resulting from ablation from around each seed staging position 52 in a row 55 allows the operator to visually inspect the ablation process and for the ablation process to be efficient as possible. Furthermore, moving smoke, debris and other material resulting from the ablation process away from the seed staging port 54 helps keep these unwanted materials from entering into the seed staging port 54 and ultimately passing into the negative pressure or positive pressure sources (not shown). For example, in the case where ablation is performed by a laser having a controlled laser beam passing through a portion of seed 62, debris, smoke and other materials are released as a result of ablating the seed 62. Allowing the smoke, debris and other materials to remain around the seed 62 during the ablation process minimizes the efficiency of the laser beam 146.

Figure 6B:
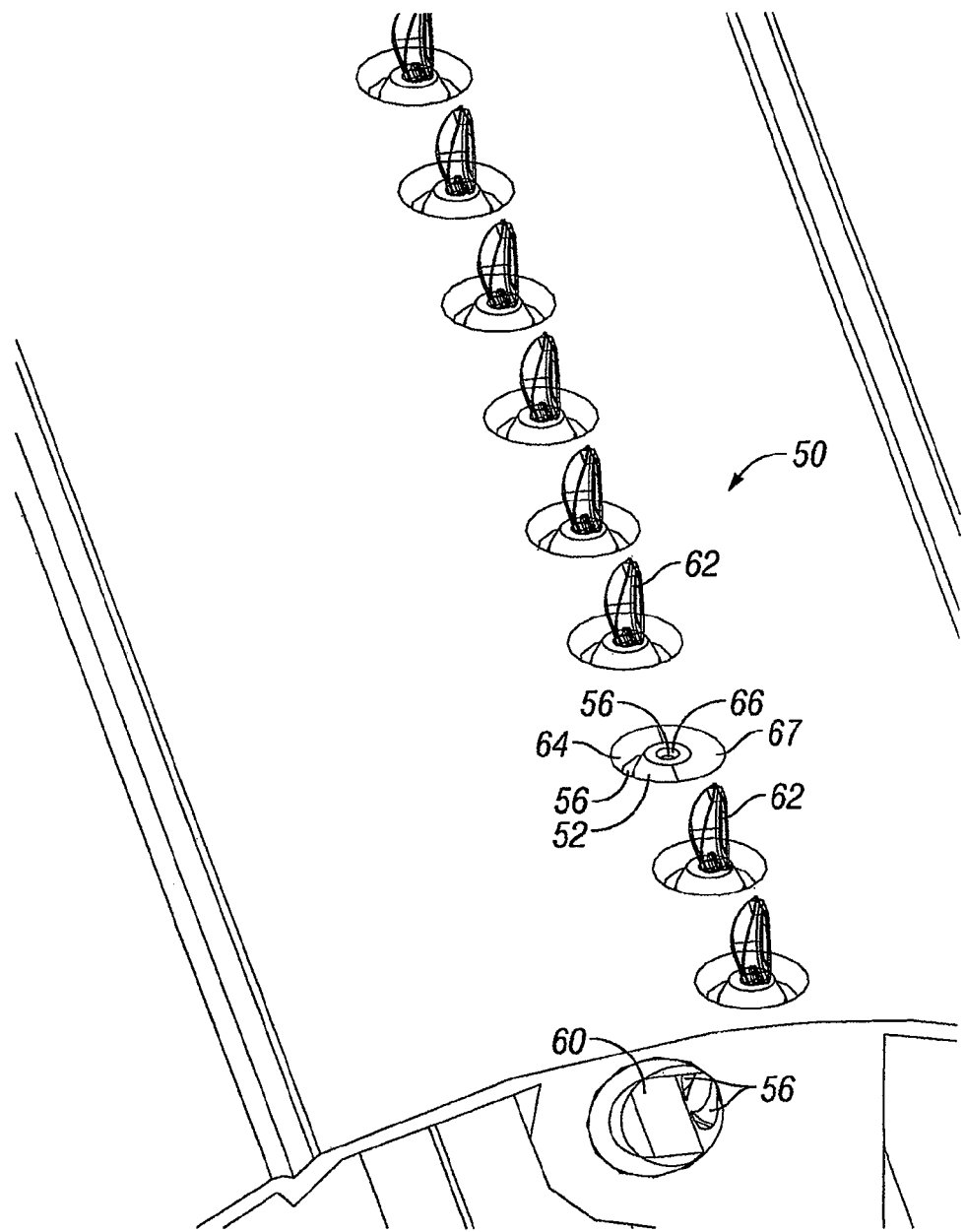
FIG. 6B is an enlarged perspective view of a seed staging position of the seed carrier according to another aspect of the invention.

FIG. 6B illustrates another embodiment of seed staging position 52. In the embodiment illustrated in FIG. 6B, recess 64 includes an insert 67 occupying a portion of recess 64. Insert 67 can be configured to occupy a 90 degree segment, 180 degree segment, a 270 degree segment, or other portion of recess 64. Insert 67, in a preferred embodiment of this invention, is configured to occupy 180 degrees of recess 64. Those skilled in the art can appreciate that insert 67 could occupy any portion of recess 64 of seed staging position 52. By changing the amount of the recess 64 occupied by insert 67, the air exiting through recess 64 from positive pressure port 56 is manipulated and controlled to prevent eddy currents from setting up at or near seed staging port 54. Eddy currents that set up at or near seed staging port 54 may prevent the sample portion 166 from being kicked-off or released from seed staging position 52 and therefore are undesirable. Thus, this invention contemplates an insert 67 occupying a portion of recess 64 to control air exiting through recess 64 to prevent eddy currents from stalling or preventing the release or kick-off of a sample portion 166 of seed 62 from seed staging position 52.

This invention contemplates that the negative pressure field acting to hold or retain a seed 62 at seed staging position 52 may be monitored for a row of seed staging positions or a single seed staging position 52 to determine if a seed 62 has been picked up and is being retained at seed staging port 54. Furthermore, visual inspection from the operator may be used to monitor whether or not each seed staging position in a row has a seed 62. In the case where a seed 62 fails to be picked up or retained at a seed staging position 52, a seed 62 may be manually positioned at the empty seed staging position 52. Seed carrier 50 may be configured so that at least a portion of the outer peripheral surface 61 of seed carrier 50 is exposed or rotates out of cabinet 26 of seed sampler station 14 whereby an operator standing or positioned at operator station 20 may monitor whether or not each seed staging position 52 has a seed 62. Thus, by summary, each seed staging position 52 has a negative pressure field communicated through a seed staging port 54 for retaining a seed 62 at each seed staging position 52 once the seed staging position enters the seed distribution system 38. The negative pressure field is maintained at each seed staging position 52 in a row 55 as the row 55 is rotated from the seed distribution system 38 to ablation system 42. The negative pressure field communicated to each seed staging position 52 in a row 55 is cut after ablation whereby a sample portion 166 resulting from the ablation process retained at each seed staging position 52 is released either by cutting the negative pressure field to each seed staging position 52 in the row or by introduction of a positive pressure field at each seed staging position 52 in the row for kicking-off or releasing the sample portion 166.

The present invention contemplates that seed carrier 50 may, at times, have one or more if its lateral ports rotated into communication with a positive or negative pressure field for evacuating or cleaning out one or more of the ports within seed carrier 50.

Figure 7:
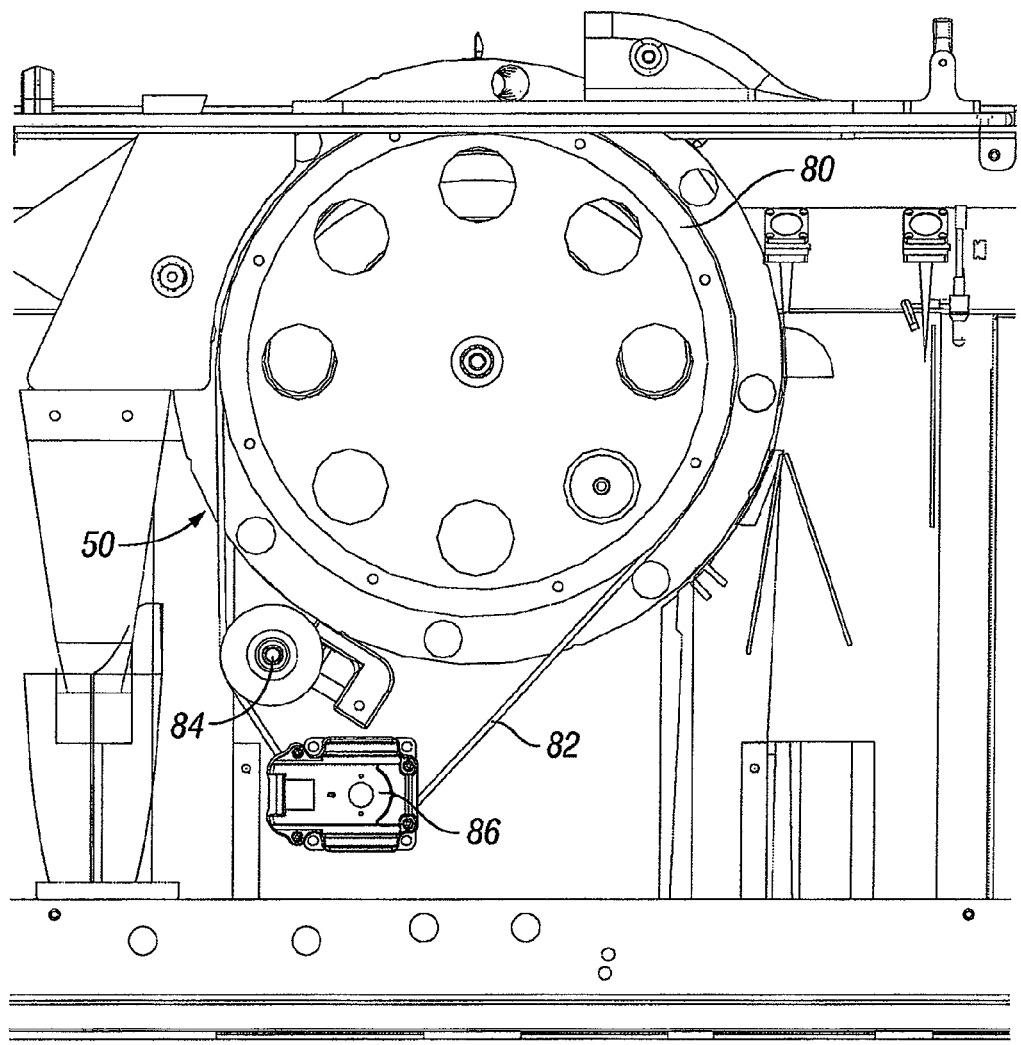
FIG. 7 is a side elevation view of a system for imparting movement to the seed carrier of this invention.
Figure 8A:
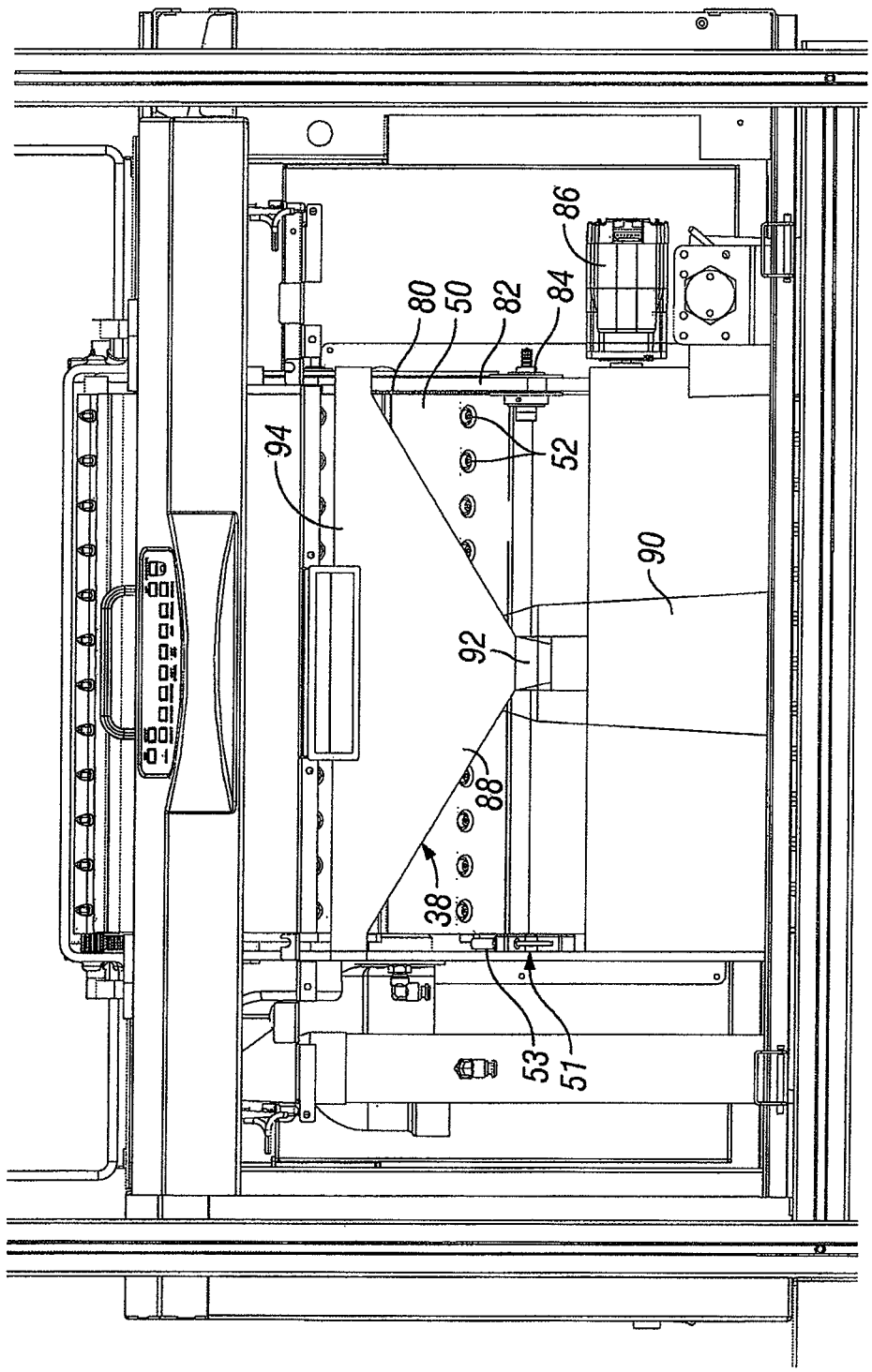
FIG. 8A is a front elevation view of a seed distribution system of the seed sampler according to one aspect of this invention.

FIG. 7 is a side elevation view of a configuration of one means for providing rotation of seed carrier 50. For example, in one aspect of this invention, rotation of seed carrier 50 may be accomplished using a motor 86 configured to drive a belt 82. Belt 82 is in operable contact with gear 80 attached to seed carrier 50. An idler or tension pulley 84 may be provided to ensure that belt 82 does not slip when being driven by motor 86 or when driving gear 80 for rotating seed carrier 50. Actuation of motor 86 may be controlled by instruction from a control system and/or seed carrier position sensing system 51 that monitors the position of seed carrier 50. For example, sensor elements 57 may be arranged to correspond with one or more features on the outer peripheral surface 61 of seed carrier 50. Sensor element 57 may be positioned on seed carrier 50 to correspond with a row of seed staging positions 55, lateral seat 140 or any one or more ports within seed carrier 50. When seed carrier position sensing system 51 senses a sensor element, an instruction for actuating or disengaging actuation of motor 86 may be communicated to motor 86 from control panel 32 or a control box 28 for controlling rotation of seed carrier 50 and the position of one or more features of seed carrier 50 relative to one or more systems of this invention. The control panel 32 may be configured whereby an operator may provide manual instructions to motor 86 for manually rotating seed carrier 50. Motor 86 may be a servomotor with a cogged drive gear driving a cogged belt 82 for interconnecting with cogs on gear 80 attached to seed carrier 50. The cogged belt 82 is kept in proper tension by an idler or tension pulley 84 having cogs for mating with the cog belt 82. Gear 80 and cogged idler or tension pulley 84 are best illustrated in FIG. 8A. The drive system for seed carrier 50 helps ensure that the position of the seed carrier 50 is accurately controlled based on input commands to motor 86.

Figure 8B:
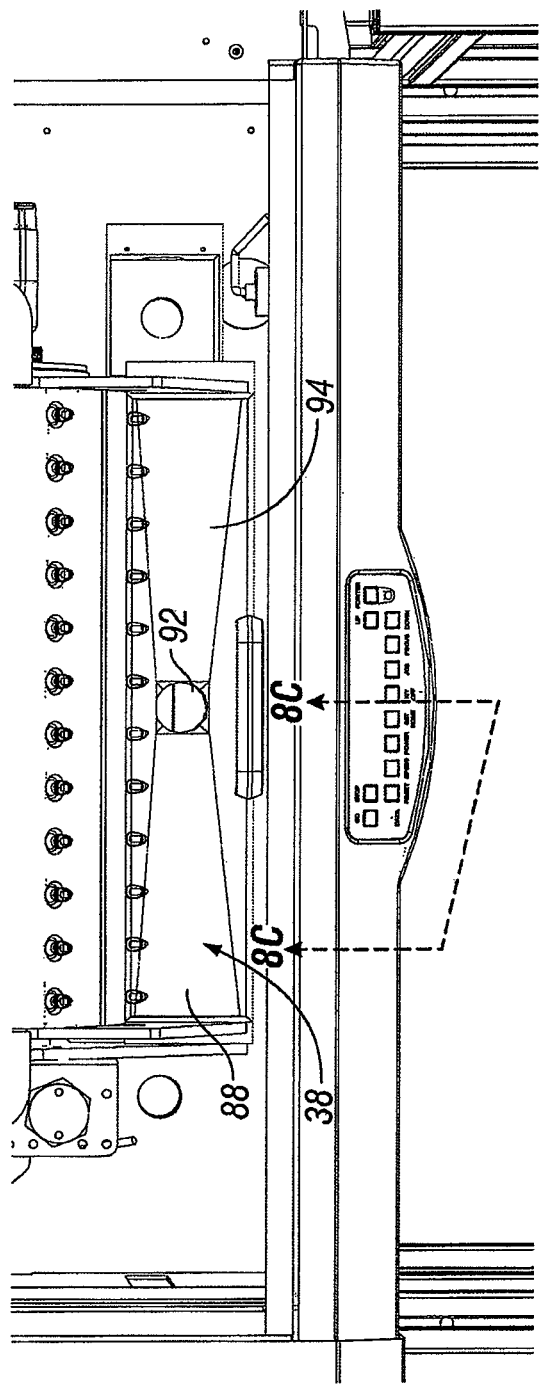
FIG. 8B is a top plan view of the seed distribution system of the seed sampler.
Figure 8C:
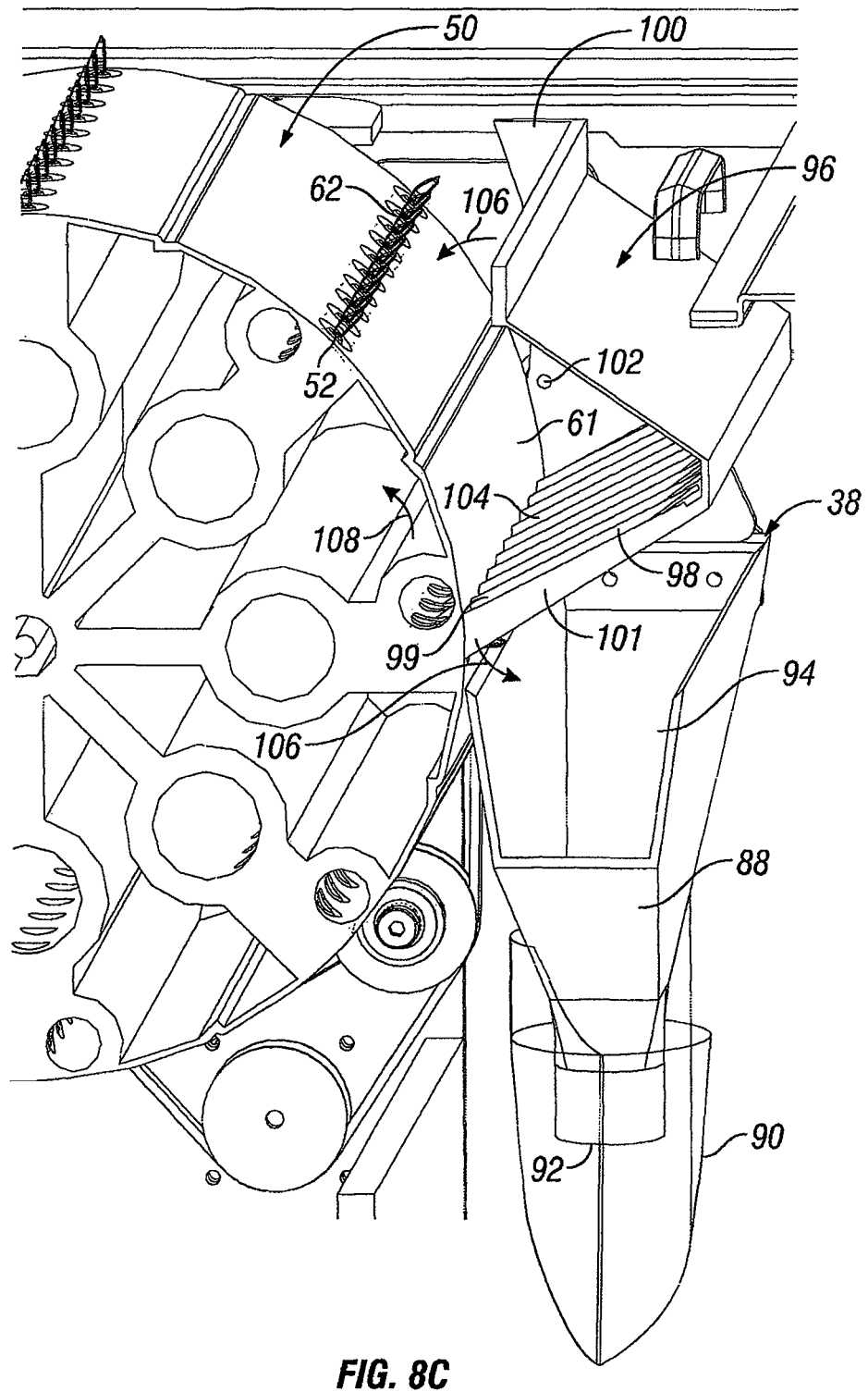
FIG. 8C is a sectional view of the seed distribution system of the seed sampler taken along line 8C-8C in FIG. 8A.

FIGS. 8A-C illustrate several views of the seed distribution system 38. It is through the seed distribution system 38 that a batch or batches of seed are introduced into the seed sampler system 10. Generally speaking, seed distribution system 38 acts as a seed hopper that is specifically configured to position one or more seed, preferably at a desired orientation, in line and at each seed staging position 52 when a row of seed staging positions 55 enter into the seed distribution system 38.

Seed distribution system 38 includes a seed distributor 96. Seed distributor 96 is pivotably attached to cabinet 26 via hinge pins 102. This allows seed distributor 96 to rotate along the direction indicated by arrow 106 in FIG. 8C. Seed distributor 96 includes an inlet 100 whereby seed may be introduced. In FIG. 8C, seed distributor 96 is shown in a seed loading position wherein the collection area 104 at the bottom of vanes 98 is closely adjacent the outer peripheral surface 51 of seed carrier 50. In the seed loading position, the collection wall 101 having vanes 98 is angled at an incline to encourage seed held within the seed distributor 96 to move toward the outer peripheral surface 61 of seed carrier 50. Thus, as seed 62 are picked up at each of the seed staging positions 52 in a row 55, a subsequent batch of seed moves toward the outer peripheral surface 61 of seed carrier 50 to be picked up by the next row of seed staging positions 55 rotated into the seed distribution system 38. Given the downward angle of the collection wall 101 of seed distributor 96, seed within the distributor 96 move toward the outer peripheral surface 61 of seed carrier 50 by gravity. A series of vanes 98 are configured into the collection wall 101 of distributor 96. Vanes 98 are aligned in parallel across the collection wall 101 in sequential order to provide columns for seed to align themselves within and be fed onto a seed staging position 52 on seed carrier 50. Vanes 98 form an alley 99 through which seed loaded into the distributor follow on their descent toward the outer peripheral surface 61 of seed carrier 50. The vanes 98 and alleys 99 may be configured to encourage seed in their movement or descent toward the outer peripheral surface 61 of the seed carrier 50 to be oriented in a desired orientation so that when picked up by a seed staging position 52 the seed is oriented relative to the seed staging position for ablation. For example, with a soybean seed, the vanes 98 and alleys 99 of seed distributor 96 may be configured so that as a soybean seed travels across collection wall 108 toward the collection area 104 the seed is self oriented so that it is picked up by a seed staging position 52 in a desired orientation. This could include an orientation where the hilum is positioned closest the seed staging port 54 to prevent the ablation process from cutting near the hilum. In the case where the seed is corn, the vanes 98 and alleys 99 of seed distributor 96 may be configured so as to orient the tip cap of each kernel outward from the seed staging position 52 so that the kernel is oriented in a desired position as it enters into the ablation process. This invention contemplates that the surface texture of the collection wall 101 may be configured to self orient seed. Further, the geometry of the collection wall 101 may be adapted to self orient the seed as a seed descends along the collection wall 101 toward the collection area 104 adjacent the outer peripheral surface 61 of the seed carrier 50. This invention further contemplates that the seed distributor may include manual orientation of seed along the alleys 99 within collection wall 101. Other systems contemplated include a seed feeding system whereby the seed is previously or pre-oriented within the seed feeding system whereby release of the seed from the seed feeding system at the collection areas provides a seed that is already oriented in the desired orientation and ready for pick up at each seed staging position 52. Other systems for self orienting seed so that the seed is picked up by each seed staging position 52 in a desired orientation include the use of magnetic attenuation positioned at or near the collection wall 101, including near the collection area 104, to assist in orienting or encouraging orientation of seed before being picked up by a seed staging position 52. For example, in the case where the seed has been previously coated with a magnetically active coating, magnetic attenuation within or at the collection wall 101, including the collection area 104, may be used to help facilitate orientation of a seed prior to being picked up by a seed staging position 52. Other embodiments contemplated for assisting in orientation of a seed at each seed staging position 52 include one or more vanes configured to mate at the outer peripheral surface 61 of the seed carrier and having angles or contours, or surface geometry that gently encourage seed held at each seed staging position 52 to be re-oriented to a desired orientation as seed carrier 50 travels or rotates in the direction of arrow 108 shown in FIG. 8C.

In the case where it is desired to dump a batch of seed from seed distributor 96, seed distributor 96 is rotated along the direction of arrows 106 shown in FIG. 8C whereby seed within distributor 96 is dumped into funnel 88 through inlet 94. Seed is carried through the inlet 94 of funnel 88 and exits through outlet 92 into a seed container such as a seed envelope 90 or other container. The seed container or seed envelope 90 is removable and replaceable at the outlet 92 of funnel 88 for capturing a batch of seed whenever released from seed distributor 96. The outlet 92 of funnel 88 may be accessed through a door in cabinet 26 of seed sampler station 14. Thus, at any time seed within distributor 96 may be discarded by rotating distributor 96 in the direction of arrows 106 in FIG. 8C for dumping or releasing the seed into funnel 88 whereby the seed travels through funnel 88 and is collected within a container such as a seed envelope 90.

Figure 9A:
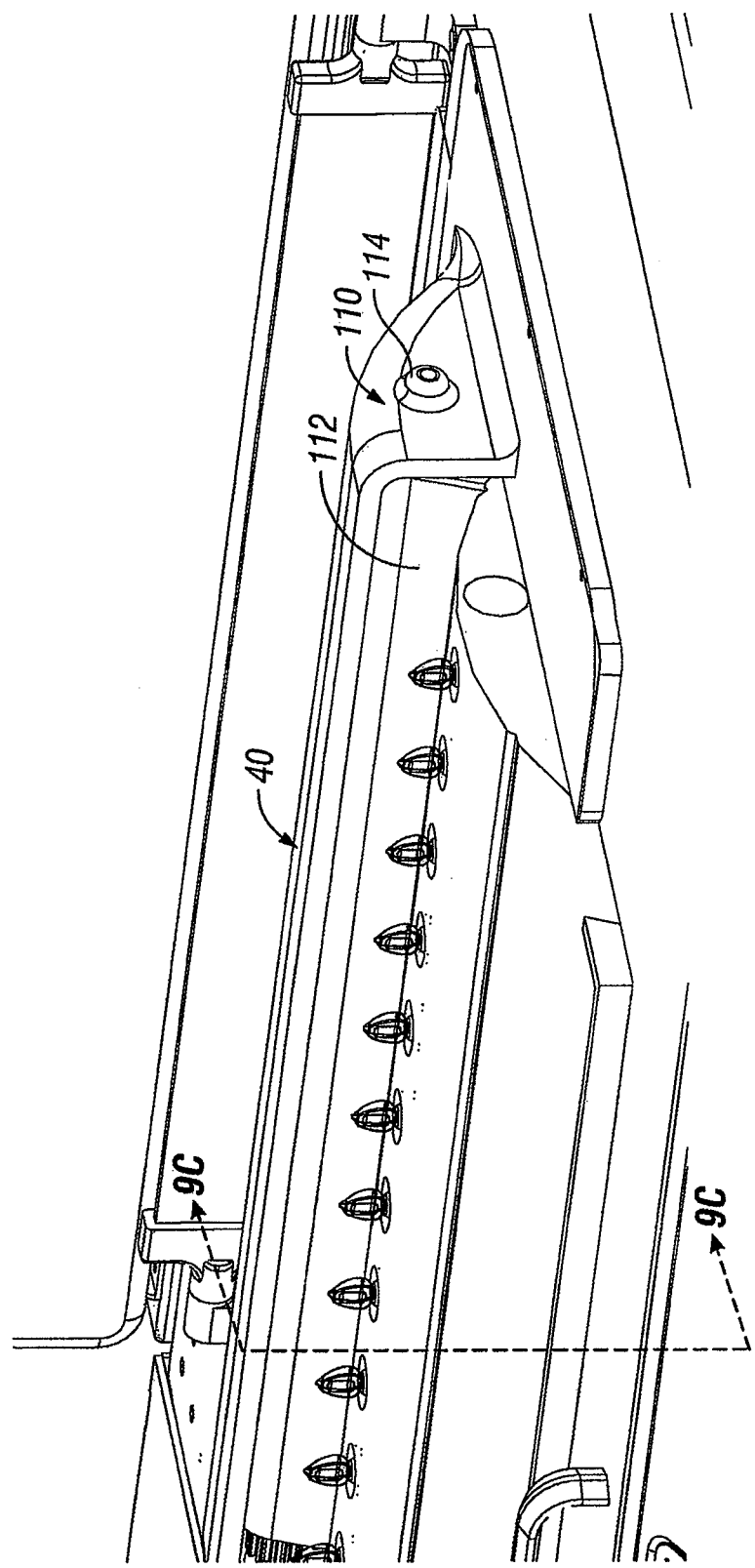
FIG. 9A is a perspective view of an ablation enclosure system according to one aspect of this invention.
Figure 9B:
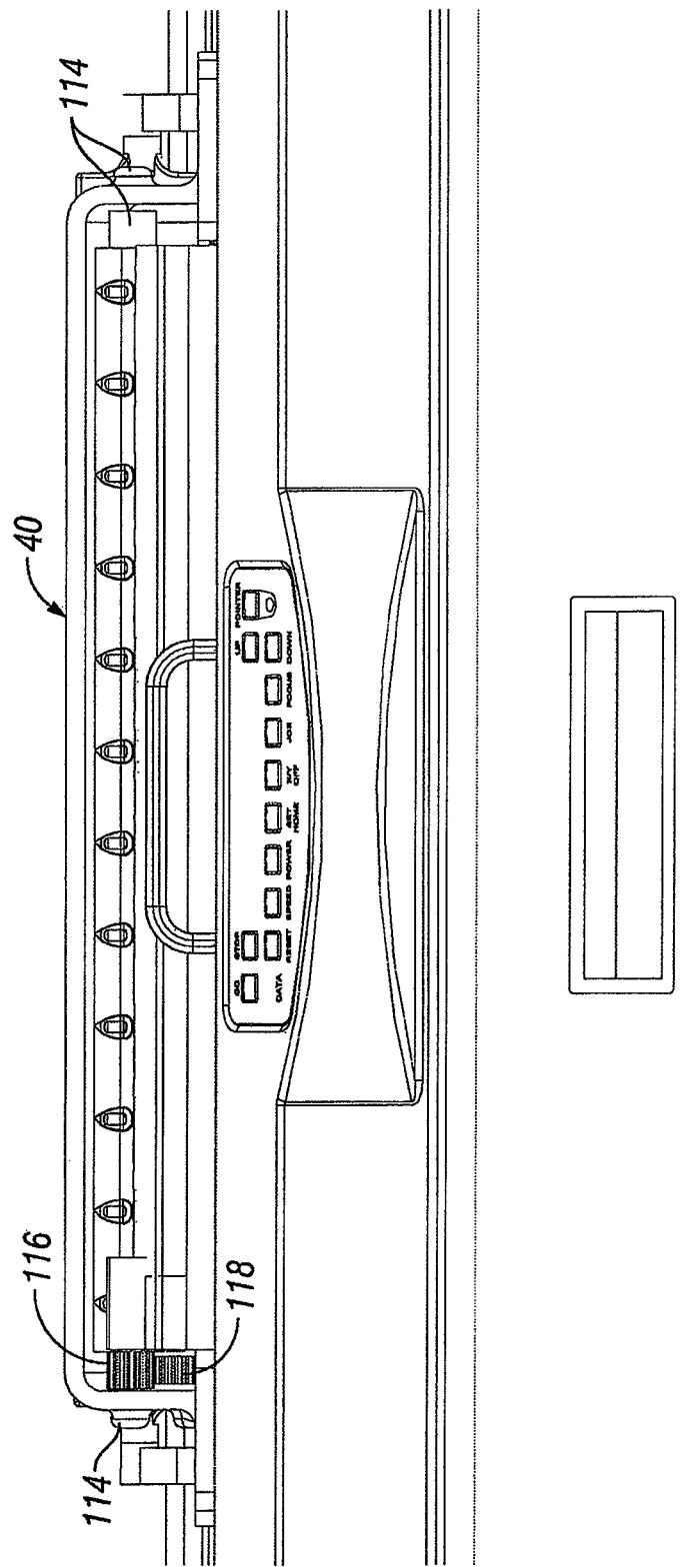
FIG. 9B is a front elevation view of the ablation enclosure system.
Figure 9C:
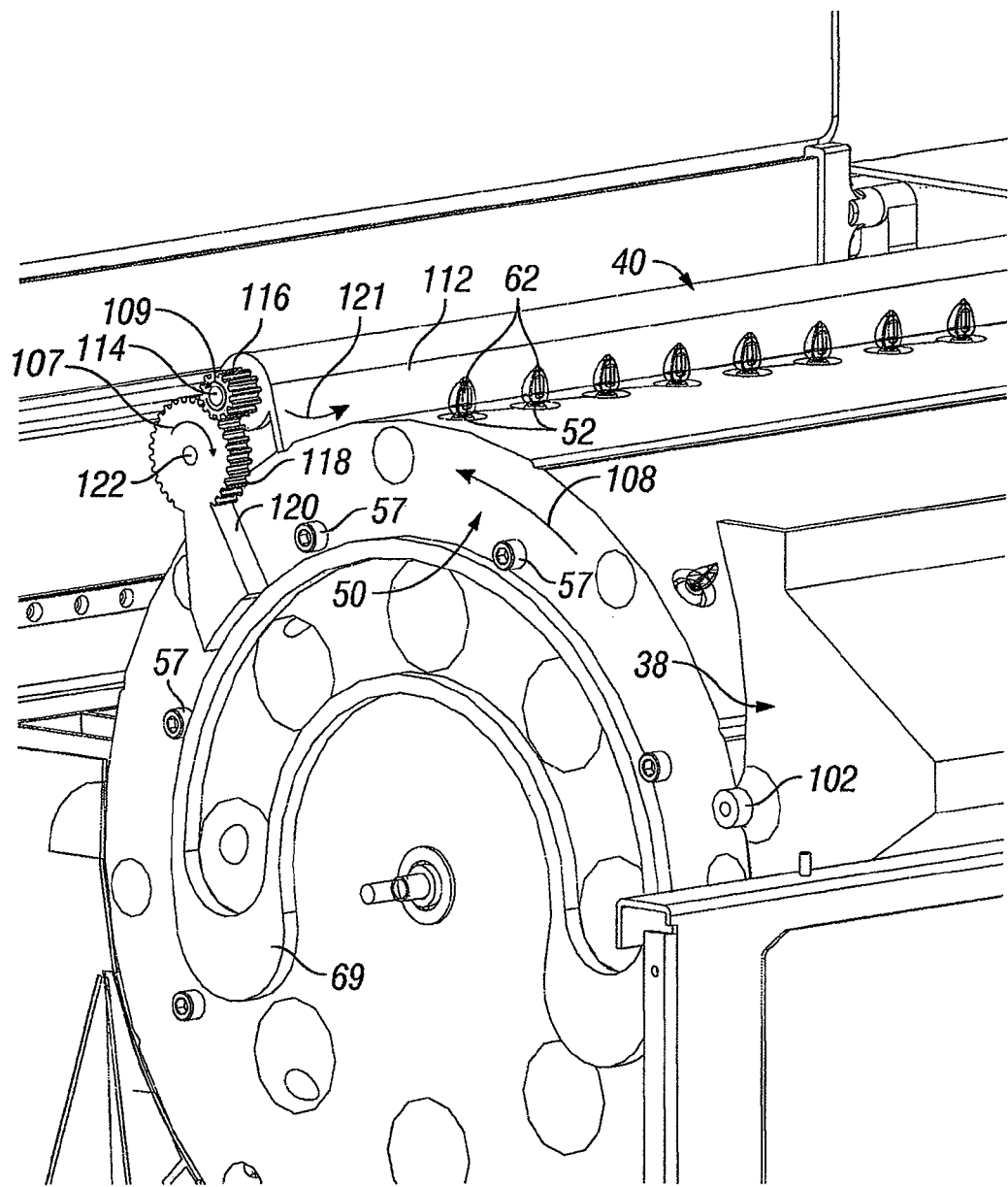
FIG. 9C is a sectional view of the ablation enclosure system taken along the line 9C-9C in FIG. 9A.

FIGS. 9A-C illustrate various views of an ablation enclosure system of this invention. Generally speaking, the ablation enclosure system 40 provides a door or a gate for a row of seed 55 to enter into the ablation system 42, and yet still provide an enclosed environment while ablation is occurring. The ablation enclosure system 40 of this invention includes a cover 110 positioned generally atop cabinet 26 above ablation system 42 and a portion of seed carrier 50. The cover 110 aids in keeping smoke, debris and other materials resulting from ablation from escaping from the seed sampler system 10 into the surrounding environment. Operably attached to cover 110 is a flap 112. Flap 112 is pivotally attached to cover 110 via hinges 114. The ablation enclosure system 40 also includes a flap gear 116 operably attached at hinge 114 of flap 112. Flap gear 116 includes a plurality of cogs. The ablation enclosure system 40 also includes an armature 120 having an armature gear 118 with a plurality of cogs that intermesh with the cogs on flap gear 116 when the ablation enclosure system 40 is assembled. The armature 120 has a hinge pin 122 whereby the armature 120 is rotatable relative to cover 110. Flap 112 also has a hinge pin 114 whereby the flap is rotatable relative to cover 110. As seed carrier 50 rotates along the direction of arrow 108 shown in FIG. 9C, a sensor element 57 engages armature 20 causing armature 120 to rotate in the direction of arrow 107 illustrated in FIG. 9C. Rotation of armature 120 imparts a counter rotation (in the direction of arrow 109) to flap gear 116 which in-turn imparts rotation to flap 112 (in the direction of arrow 121). As seed carrier 50 rotates along the direction of arrow 108, flap 112 lifts and opens whereby seed 62 staged in a row of seed staging positions 55 passes by the open flap 112. When seed 62 in a row of seed staging positions 55 have passed by flap 112, armature 20 is no longer actuated by the sensor element 57 and thereby allows the flap 112 to drop back into a closed position illustrated in FIG. 9C. Thus, the actuation of armature 120 by sensor element 57 causes flap 112 to open at the appropriate time as a row 55 of seed 62 are rotated into the ablation system 42.

Figure 11A:
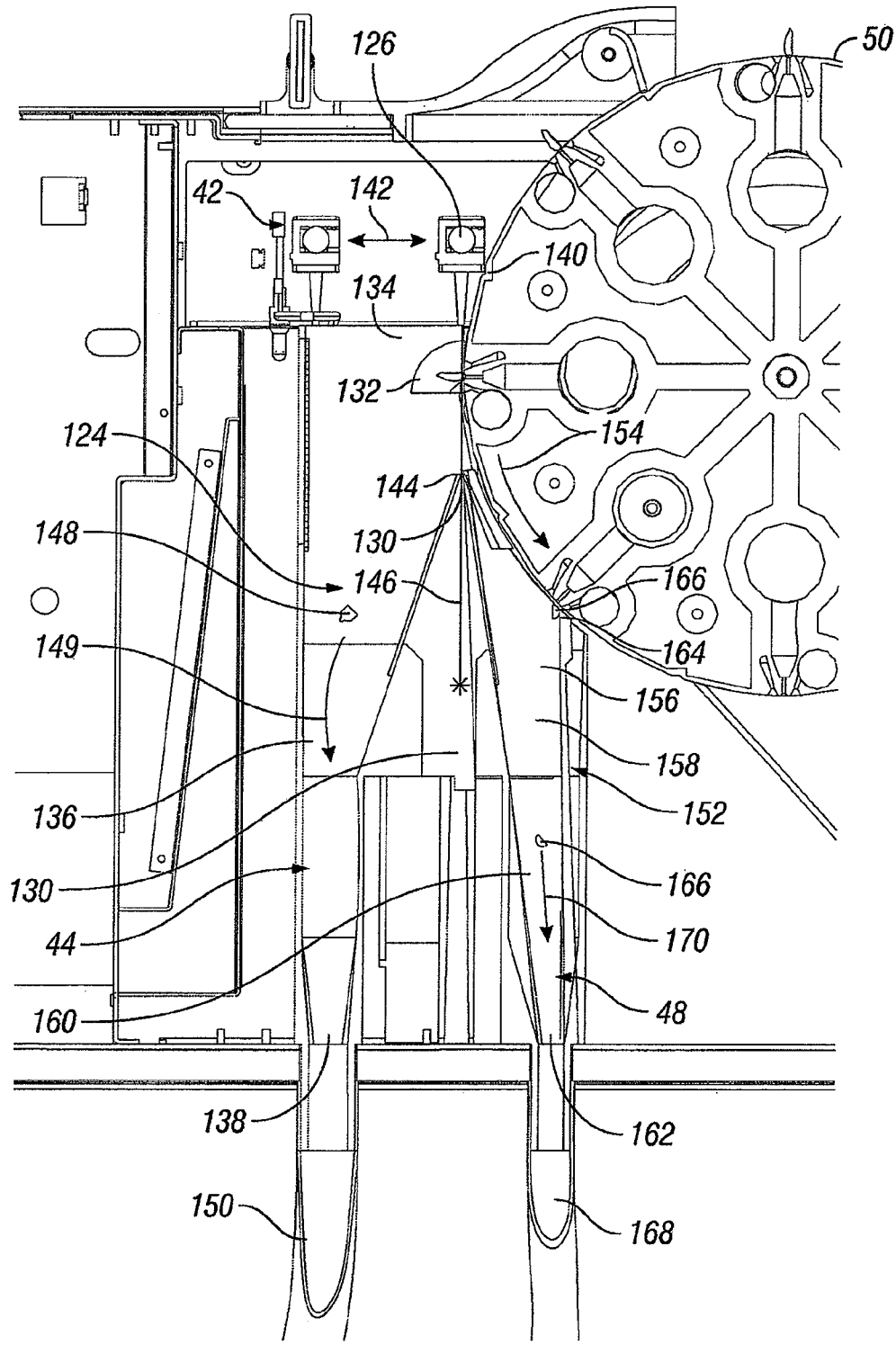
FIG. 11A is a sectional view of an ablation system and seed collection system of this invention.

FIGS. 10 and 11A-B illustrate various views of the ablation system 42 and seed collection system 22. The ablation system platform 42 comprises a commercial laser platform. One example of a suitable commercial laser platform comprises a 75 watt Epilog 36 Helix laser CO2 engraving, cutting, and marking system available at Epilog Laser, 16371 Table Mountain Pkwy, Golden, Colo. 80403. The laser ablation system 42 includes a laser ablation device 126. The laser ablation device 126 is configured to translate in various directions including those illustrated by directional arrows 128 and 142.

FIG. 11 illustrates the laser ablation device 126 moving between a home position and a cutting position adjacent the outer peripheral surface 61 of seed carrier 50. When seed carrier 50 is rotating, laser ablation device 126 may be moved back to or toward the home position away from the outer peripheral surface 61 so as to not impede or interfere with the rotation of seed carrier 50. Movement and the timing of movement of laser ablation device 126 may be controlled manually or by a control system of this invention, such as control panel 32. In the cutting position, a portion of the laser ablation device 126 docks within lateral seat 140 in the outer peripheral surface 61 of seed carrier 50. This allows the laser ablation device 126 to get close enough to the outer peripheral surface 61 of the seed carrier 50 so that the laser 146 can cut away or remove the sampled seed 148 from a small sample portion 166 left at each seed staging position 52. After each seed 62 is ablated, the sampled seed 148 falls into the sampled seed collection manifold 124 and travels by gravity along the direction illustrated by arrow 149. The sample portion 166 of the seed remains at the seed staging position 52 until it is released by cutting communication of the negative pressure field or vacuum to the row of seed staging positions 55. As the laser ablation device 126 moves in the direction identified by arrow 128 in FIG. 10, the laser 146 cuts through or ablates each seed 62 at each seed staging position 52 in a row 55. The sampled seed 148 drops into separated channels of the sampled seed collection manifold 124 as each of the seed in the row 55 are sequentially ablated.

FIG. 10 best illustrates how each sampled seed collection area 132 of the sampled seed collection manifold 124 are separated by a wall 134. Thus, each sampled seed 148 is communicated through separate channels within the sampled seed collection manifold 124. The sampled seed 148 travels through the funnel portion 136 of the sampled seed collection manifold 124 along the direction of arrow 149 and into conduit 150 by passing through outlet 138 of sampled seed collection manifold 124. In FIG. 11A the seed collection system 22 includes a pass-through 130 between the sampled seed collection manifold 124 and sample portion collection manifold 152, whereas in FIG. 11B, the pass-through 130 is located between sampled seed collection manifold 124 and the outer peripheral surface 61 of seed carrier 50. In both cases, the laser 146 travels through the pass-through 130 and defuses before impinging upon one or more surfaces, edges, or features of the seed collection system 22. After the laser ablation device 126 has passed across a row of seed 62 staged at the seed staging positions 52 and the laser ablation device 126 has been moved away from the outer peripheral surface 61 of seed carrier 50, motor 86 is engaged to rotate seed carrier 50 so that the sample portion 166 of the seed is moved into the sample portion collection manifold 152.

The present invention includes redundancy in the sampled seed and sample portion removal/releasing systems to ensure that sampled seed 148 does not get hung up at a seed staging position 52 after being ablated by laser 146. For example, the seed collection system 22 may include a sampled seed kick-off device 144 within sampled seed collection manifold 124 for separating a sampled seed 148 from a sample portion 166 without prematurely separating the sample portion 166 of the seed 62 from the seed staging position 52. The sample release assist systems work in conjunction and cooperation with the pneumatic system 49 for providing the necessary redundancy in system 10 to ensure that both sampled seed 148 and sample portions 166 of seed 62 are released, collected and communicated into respective storage locations.

As seed carrier 50 rotates along the direction of arrow 154, sample portion 166 of seed 62 is moved into sample portion collection manifold 152. The sample portion 166 of seed 62 at each seed staging position 52 (post ablation) is sufficiently thin so as to able to pass by the sample seed kick-off device 144. As seed carrier 50 continues to rotate along the direction identified by arrow 154 in FIG. 11, sample portions 166 of seed 62 enter sample portion collection manifold 152, and specifically the sample collection area 156 of sample portion collection manifold 152.

In the sample collection area 156 several things may occur to kick-off, release or remove sample portion 166 of each seed 62 in a row 55 from each seed staging position 52. For example, when a row of seed staging positions 55 is in the sample collection area 156 of sampled portion collection manifold 152, positive pressure manifold 76 is in communication with lateral ports 58 whereby a positive pressure field is communicated through lateral ports 58 causing air to be forced out of each seed staging port 54 in a row of seed staging positions 55. The burst of air exiting the seed staging ports 54 causes the sample portions 166 of seed 62 to be released or kicked-off the staging positions 52 in that particular row 55. The sample portion 166 of the seed travels by gravity through separated channels of funnel 160 (wherein the funnel 160 is separated into separate channels by walls 158) into conduit 168 through outlet 162. When a row of sample portions 166 of seed are moved into the sample collection area 166 another row of seed staging positions 55 are moved into the ablation system for ablating as illustrated in FIG. 11A-B. The laser ablation device 126 moves into the cutting position and ablates the row of seed 55 after which the seed carrier is rotated along the direction of arrow 154. Any remaining sample portions 166 of seed 62 still attached or clinging to a seed staging position 52 in the sample collection area 156 are removed or kicked-off by sample kick-off device 164. The sample kick-off device 164 prevents sample portions 166 of seed from remaining at the seed staging positions 52 after a row of seed staging positions 55 carrying the sample portions 166 of seed are rotated out of the sampled portion collection manifold 152. Sampled seed kick-off device 144 and sample portion kick-off device 164 comprise any strip, edge, bristles, membrane, or flap, etc. whether rigid, semi-rigid or bendable, positioned to contact respective sampled seed or sample portions of a seed when a row of seed carrying positions 55 is rotated out of the sampled seed collection manifold 124 and the sample portion collection manifold 152. Thus, this invention contemplates a sampled seed collection manifold 124 and sampled portion collection manifold 152 that prevent sampled seed 148 or sample portions 166 of the seed 62 from being communicated through the seed collection system 22 in error.

FIG. 11B illustrates another configuration for seed collection system 22. As mentioned previously, the sampled seed collection manifold 124 may be staged together with the sample portion collection manifold 152 about the outer peripheral surface 61 of seed carrier 50. In FIG. 11B, sample seed collection manifold 124 is staged apart from sample portion collection manifold 152. One embodiment for the seed collection system 22 comprises positioning the sample portion collection manifold 152 along the outer peripheral surface 61 of the seed carrier 50 at the lowest possible point to facilitate movement of the sample portion 166 of each seed 62 through the sample portion collection manifold 152 into the seed storage system 24. Regardless of the position of the sample portion collection manifold 152, pneumatic assistance may be used to facilitate travel of the sampled seed 148 and/or sample portion 166 of seed 62 through their respective manifolds into the seed storage system 24.

Figure 12A:
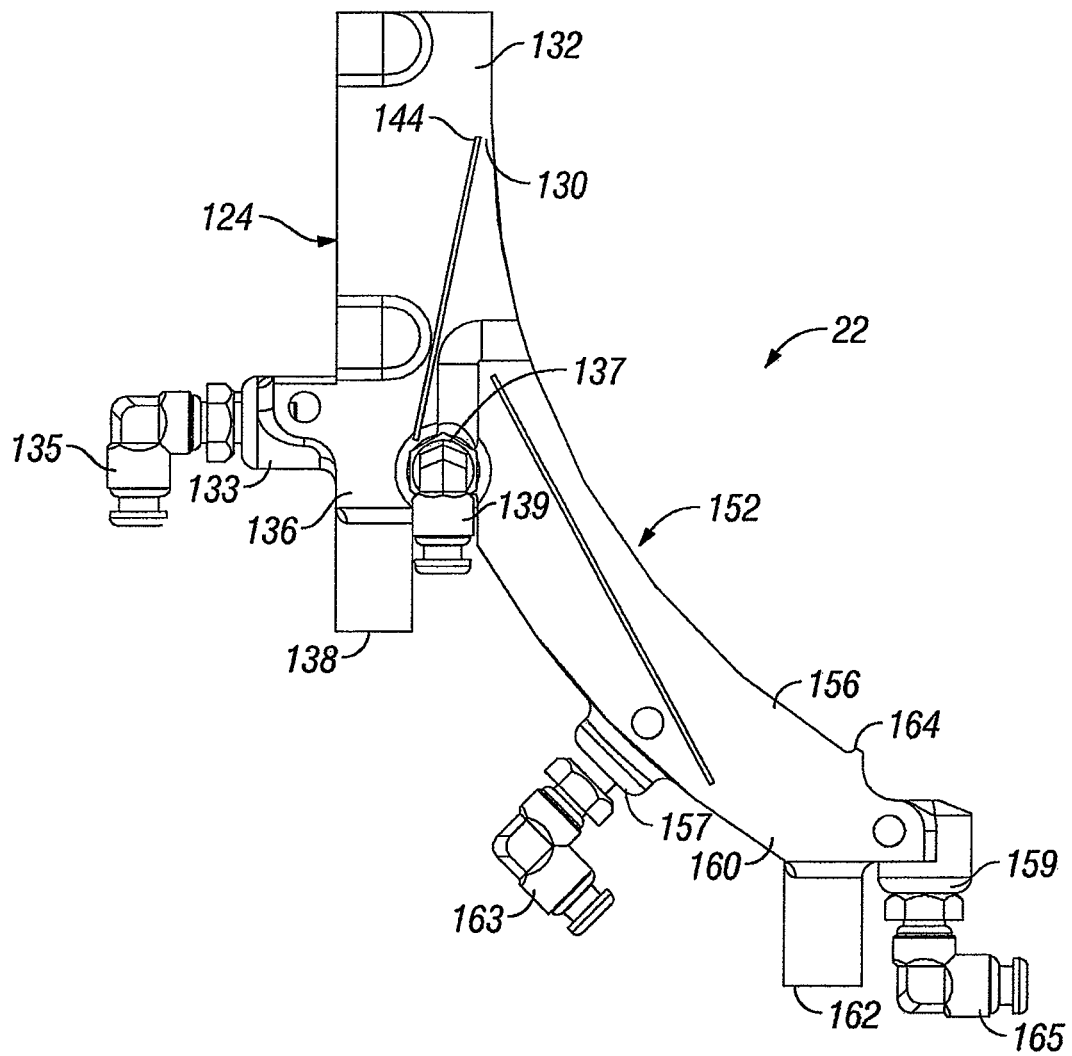
FIG. 12A is an enlarged side elevation view of a seed collection system of the invention.

This invention contemplates other embodiments for seed collection system 22. One embodiment is illustrated in FIG. 12A. The seed collection system 22 comprises a sampled seed collection manifold 124 and a sample portion collection manifold 152. The sampled seed collection manifold 124 includes features illustrated in previous embodiments, including a pneumatic assist system for encouraging both the release and travel of the sampled seed 148 and sample portion 166 into the seed collection system 22. Thus, as each sampled seed 148 is ablated from the sampled portion 166 of the seed 62, the sampled seed 148 drops or is assisted in movement away from staging position 52 and through outlet 138 at least in part by air passing through ports 133 and 137 into each funnel 136 associated with each seed staging position 52 in a row 55. Air from a pneumatic source may be provided to ports 133 and 137 through inlets 135 and 139. Similarly, on the sample portion collection side, air passing into sample portion collection manifold 152 enters through inlets 163 and 165 and is distributed proportionally into each funnel 160 via ports 157 and 159. The air passing through manifold 152 assists in moving the sample portion 166 of a seed 62 away from the staging position 52 so that gravity, either alone or in combination with pneumatic assistance, facilitates the travel of sample portion 166 through manifold 152 and through outlet 162 into seed storage system 24. Thus, gravity coupled with pneumatic assistance may be used in embodiments of this invention to move both sampled seed 148 and sample portions 166 through manifolds 124 and 152 into seed storage system 24.

Figure 12B:
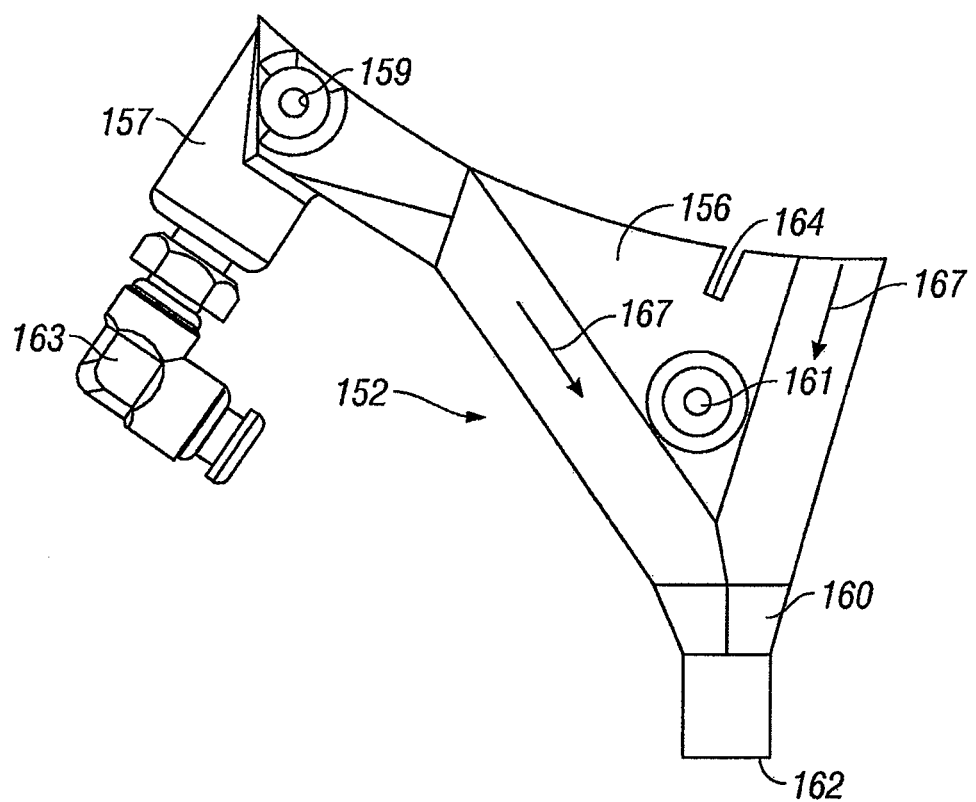
FIG. 12B is an enlarged side elevation view of a sample portion collection manifold according to one aspect of this invention.
Figure 13:
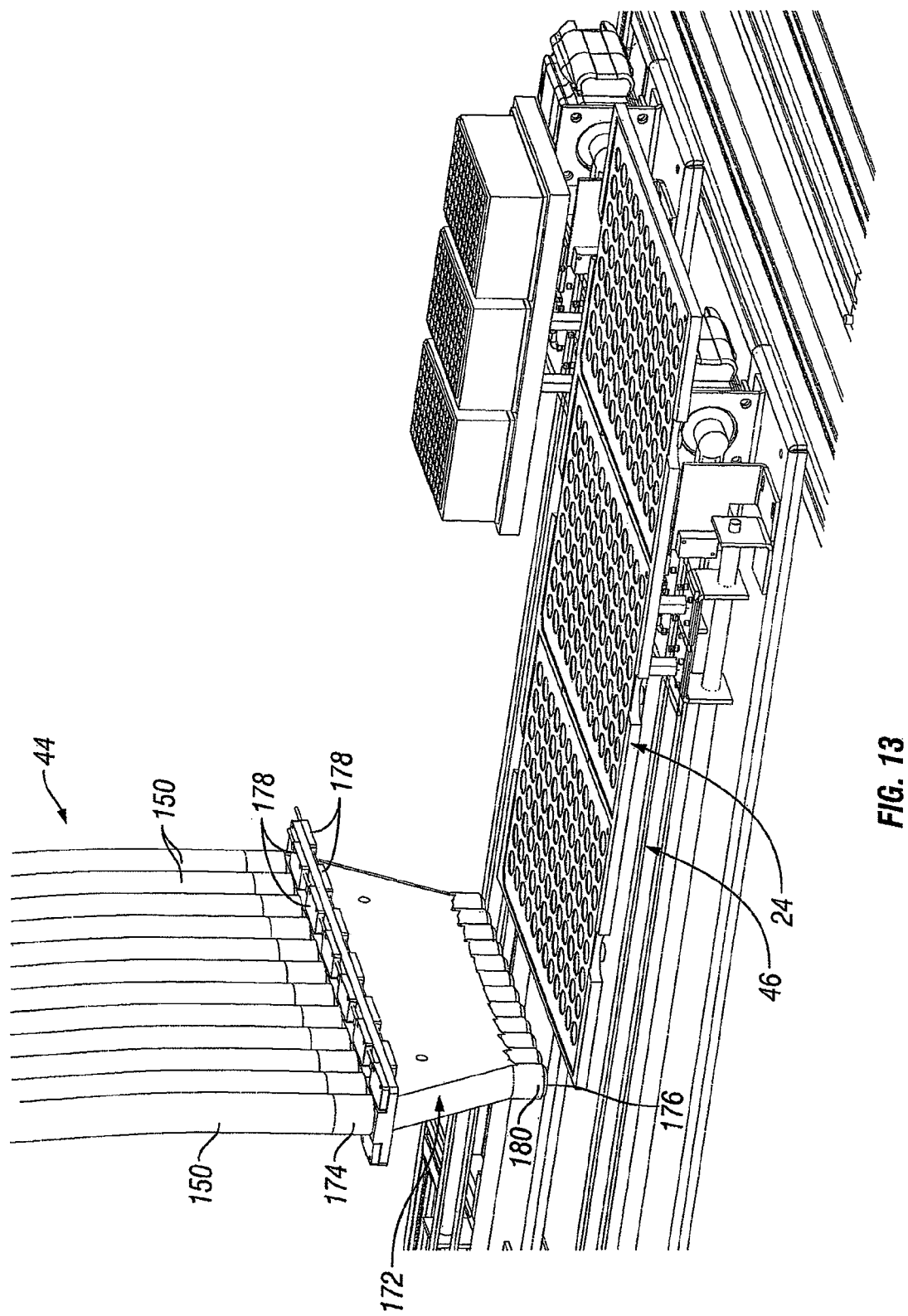
FIG. 13 is a perspective view of a seed distribution system for the sampled seed portion according to one aspect of the invention.

In a preferred aspect of the invention, manifold 124 and 152 include separated channels for handling each sampled seed and seed portion in a singulated manner. For example, each channel in the sample seed collection manifold 124 is in communication with a respective conduit 150 whereby each sampled seed 148 is maintained in singulation (separation) from the others as they travel from the seed staging positions 52 through the sampled seed collection manifold 124 and into respective conduits 150. Like the seed collection manifold illustrated in FIG. 12A, the sampled portion collection manifold 152 illustrated in FIG. 12B may include one or more pneumatic assist systems for helping to move the sample portion 166 of each seed through the manifold into the seed storage system 24 via conduits 168. In one aspect, sample portion collection manifold 152 includes an inlet 163 in communication with a positive pressure source (not shown) and manifold 152 via inlet 157. Air is distributed proportionally through ports 159 and 161 into manifold 152 for providing a stream of air whether intermittently or varying along the direction of arrows 167 to assist in moving sample portions 166 of each seed through the sample portion collection manifold 152 and into the seed collection system 24. The pneumatic systems illustrated in FIGS. 12A-B may be used in combination with the sampled seed kick-off device 144 and sample portion kick-off device 164 shown in FIG. 11A-B. This invention contemplates that either or both of the sampled seed collection manifold 124 and sample portion collection manifold 152 may include a pneumatic assist system in combination with or independent of the sampled seed kick-off device 144 and sample portion kick-off device 164. Positive pressure introduced into ports 159 and 161 may be used to urge sample portions 166 of each seed from off of seed staging positions 52 within a row 55. Once the sample portions 166 of each seed are released from the seed staging positions 52, the sample portion 166 falls through the sample portion collection manifold 152 by gravity with the assistance at least in part by the pneumatic system in communication with ports 159 and 161 for providing a stream of intermittent, constant or variable air into the sample portion collection manifold 152. The sample portions 166 travel through separate channels in the sample portion collection manifold 152 and into a funnel 160 having an outlet 162 in communication with a conduit 168. Thus each sample portion 166 is communicated in singulation or separation from other sample portions 166 and through respective conduits 168. The sampled seed 148 and sample portion 166 traveling through conduits 150 and 168 are communicated to the seed storage system 24 discussed in more detail below.

FIGS. 13-20 illustrate various aspects of the seed storage system 24. The sampled seed storage system 46 is illustrated by various views in FIGS. 13-14. The sampled seed distribution system 44 comprises a plurality of conduit 150, each conduit being in communication with a channel in the sampled seed collection manifold 124 whereby a sampled seed 148 is moved by gravity after being ablated away from the sample portion 166 of each seed through the sampled seed collection manifold 124 and into respective conduits 150. The plurality of conduits 150 are in operable communication with a sampled seed distribution manifold 172. Each conduit 150 is attached at the inlet 174 of sampled seed distribution manifold 172 and is in separated communication with a channel solely dedicated to each conduit 150 within sampled seed distribution manifold 172.

The sampled seed distribution manifold 172 comprises a seed drop sensor 178 positioned at the inlet (the outlet of each conduit 150) of the sampled seed distribution manifold 172 to monitor and verify that a sampled seed 148 travels from the sampled seed collection manifold 124 through the sampled seed distribution manifold 172. This is to verify that a sampled seed 148 does not get caught up or stalled in its progression from the ablation process through the sampled seed collection manifold 124 and into the sampled seed distribution manifold 172. Thus, seed drop sensors 178 verify that sampled seeds 148 originating from a row of seed staged at a row of seed staging positions 55 successfully passed through each of the individual conduits 150. Detected sampled seed 148 travels through the sampled seed distribution manifold 172 through outlet 176 via nozzle 180. Each conduit 150 is in communication with a nozzle 176 of the sampled seed distribution manifold 172.

The seed sampler system 10 is adapted to coordinate the collection and storage of each sampled seed 148 communicated through sampled seed distribution manifold 172 into a storage location within the sampled seed storage system 46. The sampled seed storage system is best illustrated in FIGS. 14A-B, 17, and 18A-B and comprises a tray system 186. The tray system 186 is adapted to hold one or more sampled seed containers 182. In a preferred embodiment of this invention, the sampled seed container 182 is a 96-well blister back container. Other containers of varying shape, size, well configuration and functionality are contemplated. Tray system 186 comprises one or more container positions having a plurality of apertures 187 corresponding in arrangement and configuration with the plurality of wells 184 in sampled seed container 182. In another aspect of this invention, tray system 186 includes a recessed floor 185 whereby a sampled seed container 182 may be seated within tray 186 so as to be flush with the upper surface of tray 186 and to prevent movement of sampled seed container 182. Tray system 186 may further comprise grooves or notches to allow an operator to remove and replace sampled seed containers 182.

Figure 14A:
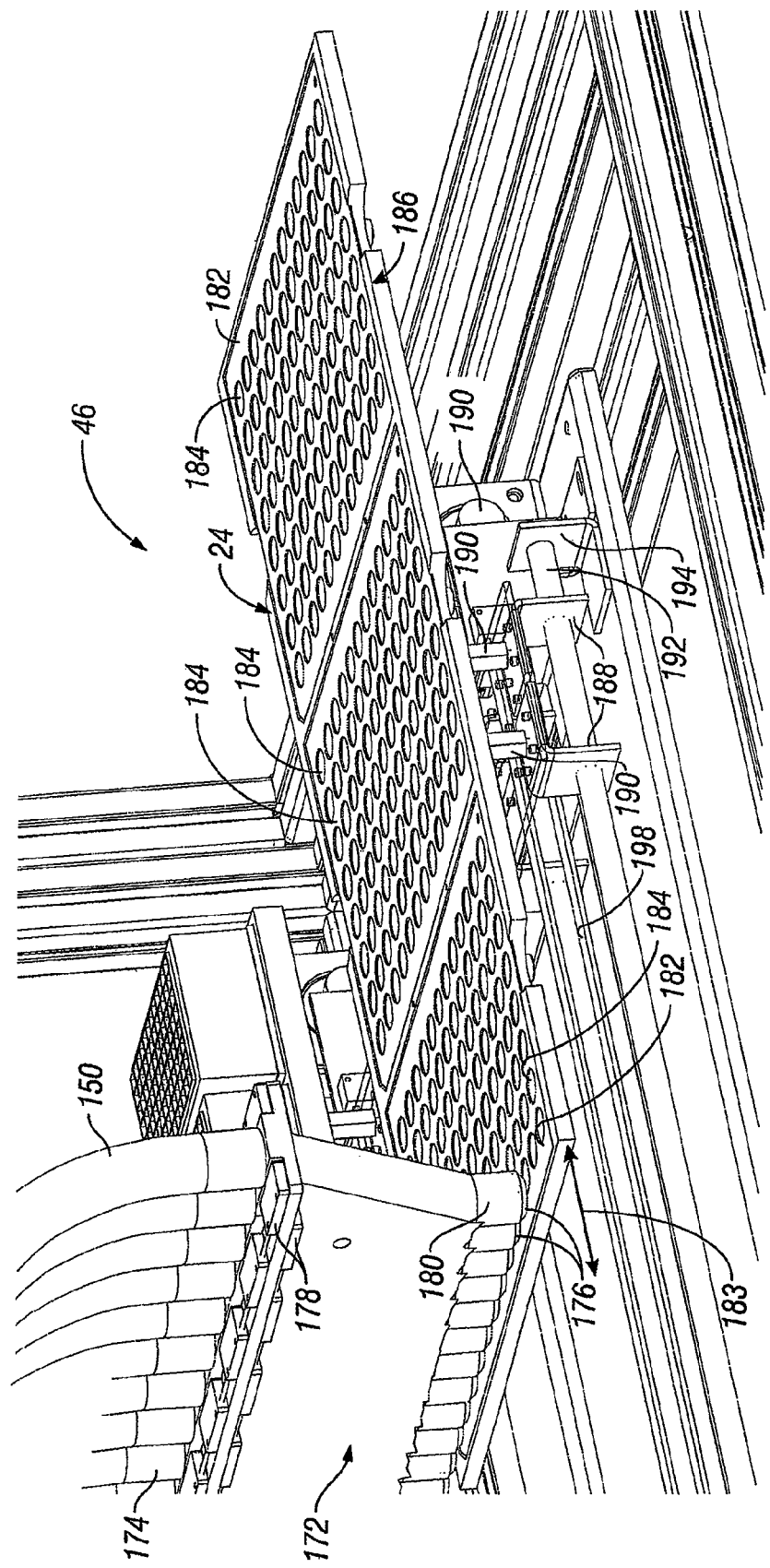
FIG. 14A is a perspective view of a seed storage system for the sampled seed portion according to one aspect of the invention.
Figure 14B:
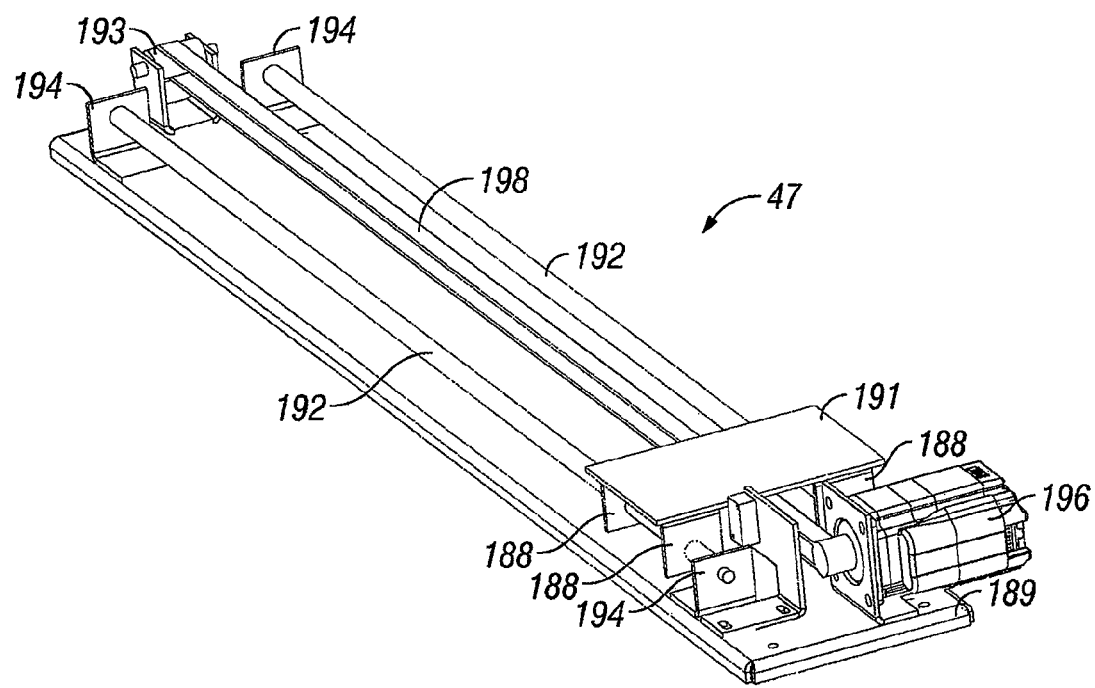
FIG. 14B is a perspective view of a shuttle system for the sampled seed storage system and the seed portion storage system according to one aspect of this invention.
Figure 15:
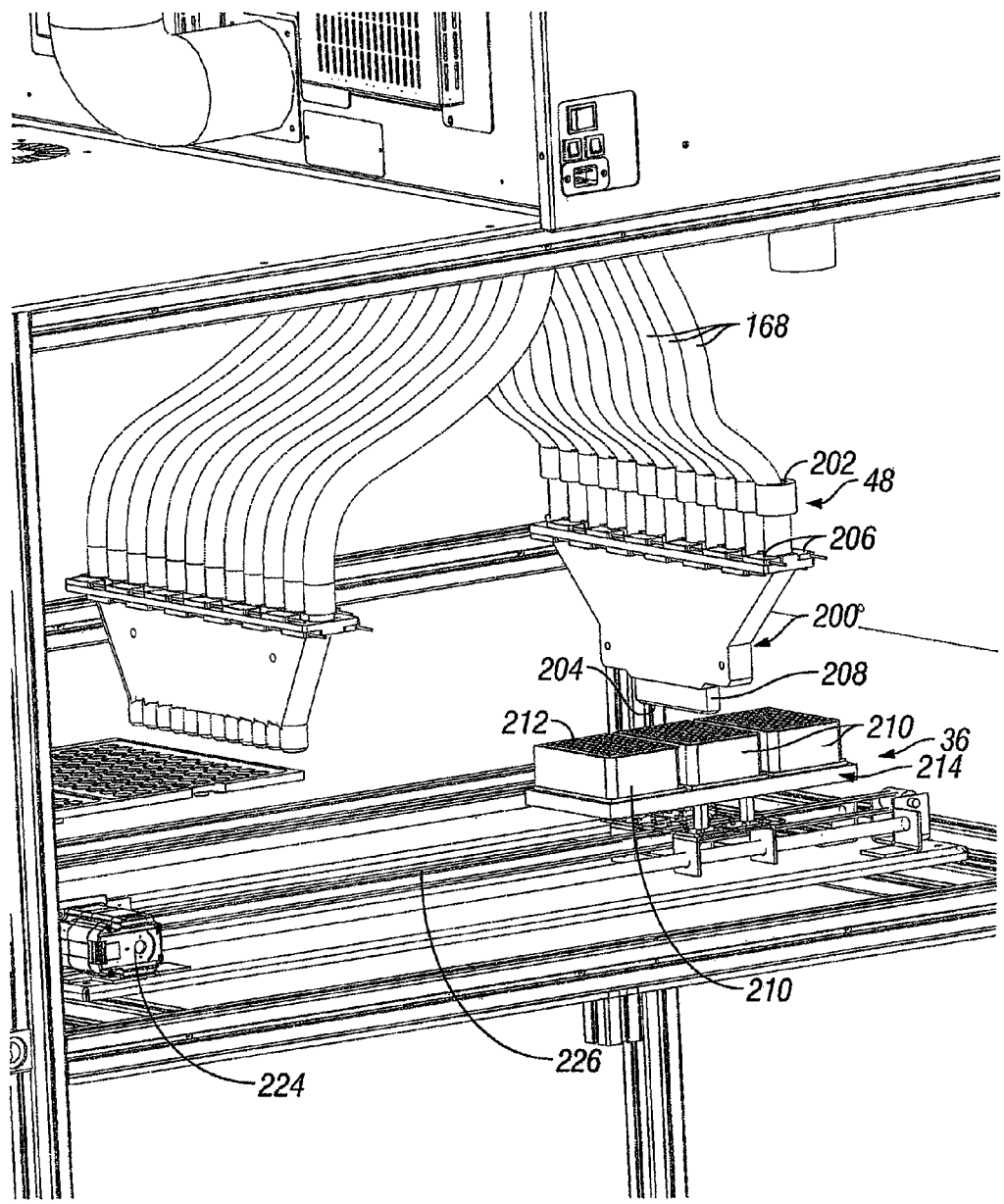
FIG. 15 is a perspective view of a seed portion distribution system according to one aspect of the invention.
Figure 16:
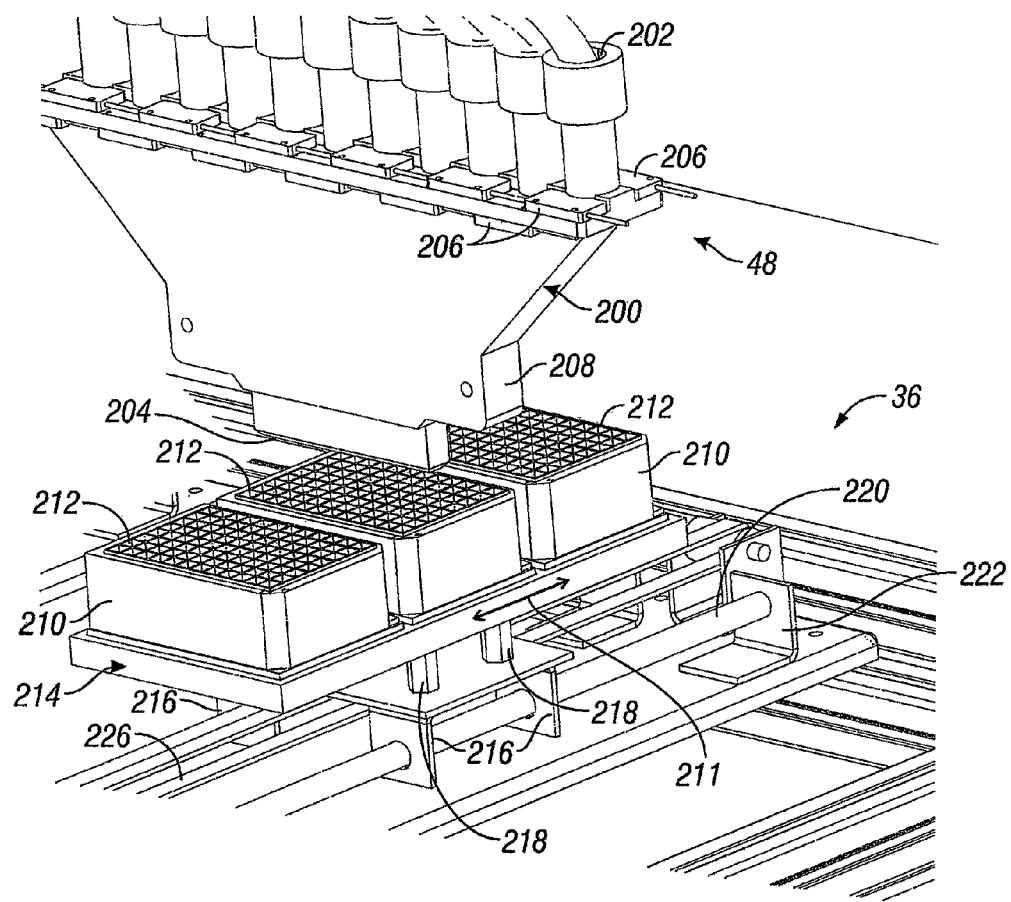
FIG. 16 is a perspective view of a seed portion storage system according to one aspect of the invention.
Figure 17:
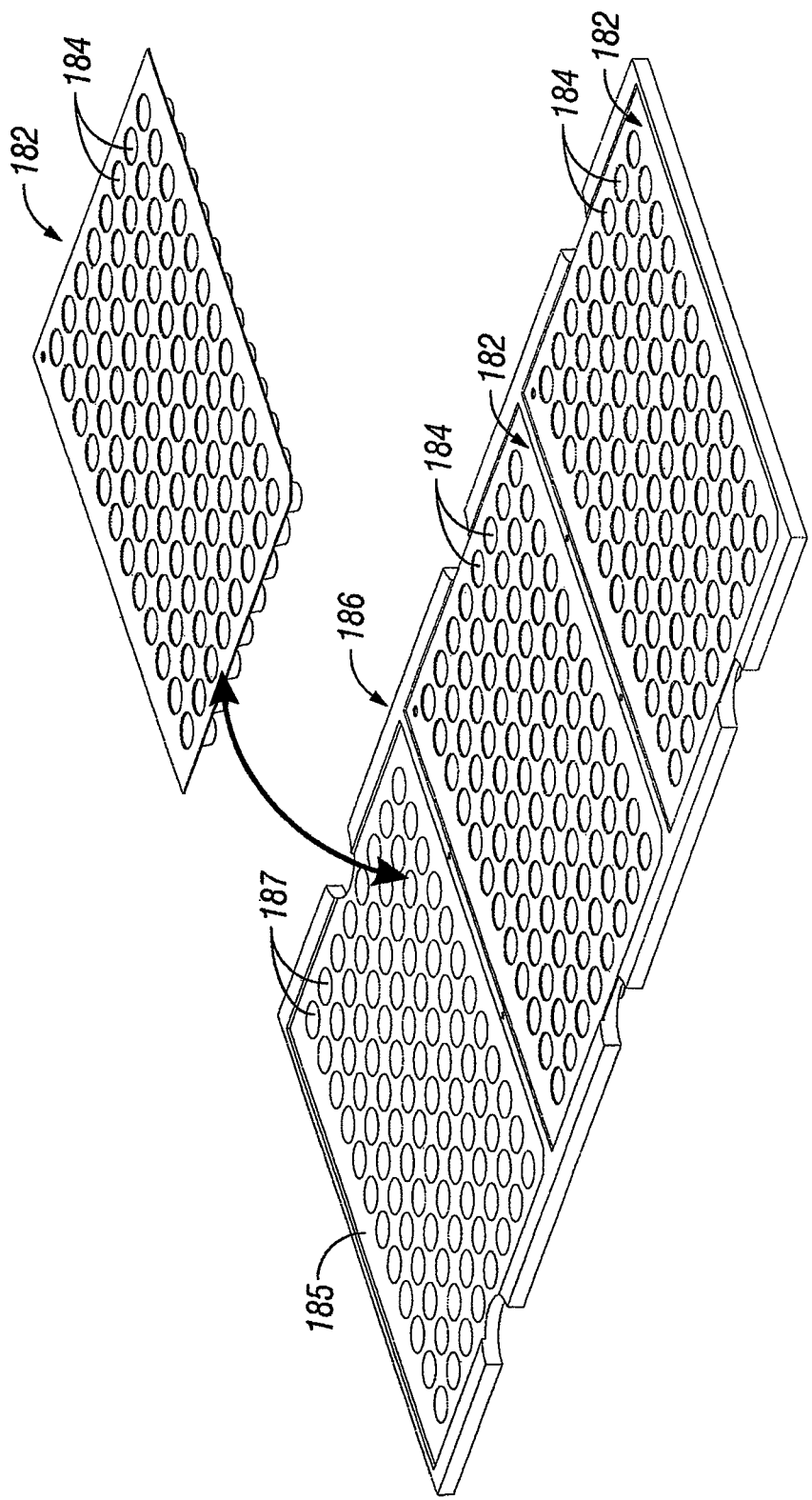
FIG. 17 is a perspective view of a sampled seed tray system of the sampled seed storage system of this invention.
Figure 18A:
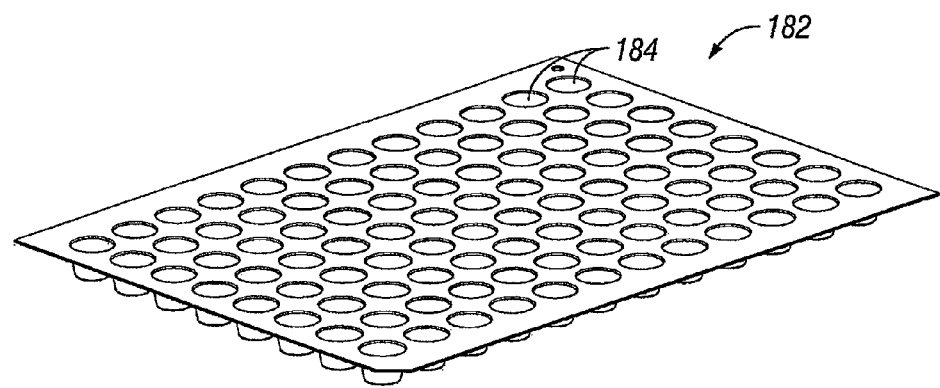
FIG. 18A is a perspective view of a sampled seed container according to one exemplary aspect of this invention.
Figure 18B:
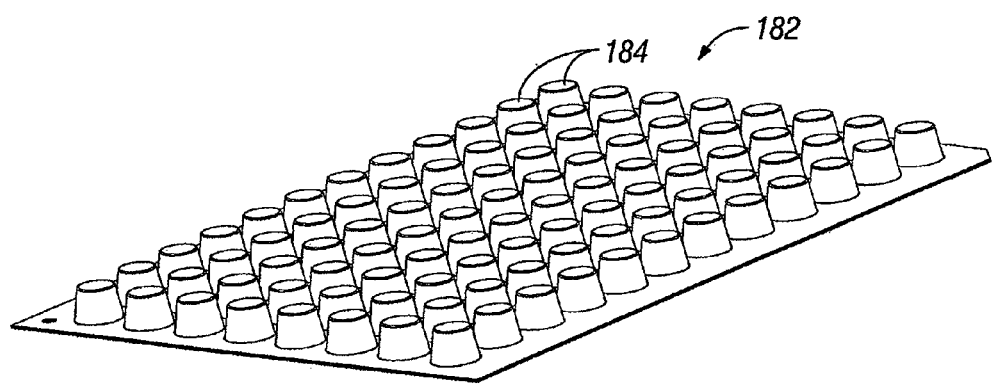
FIG. 18B is another perspective view of the sampled seed container.
Figure 19:
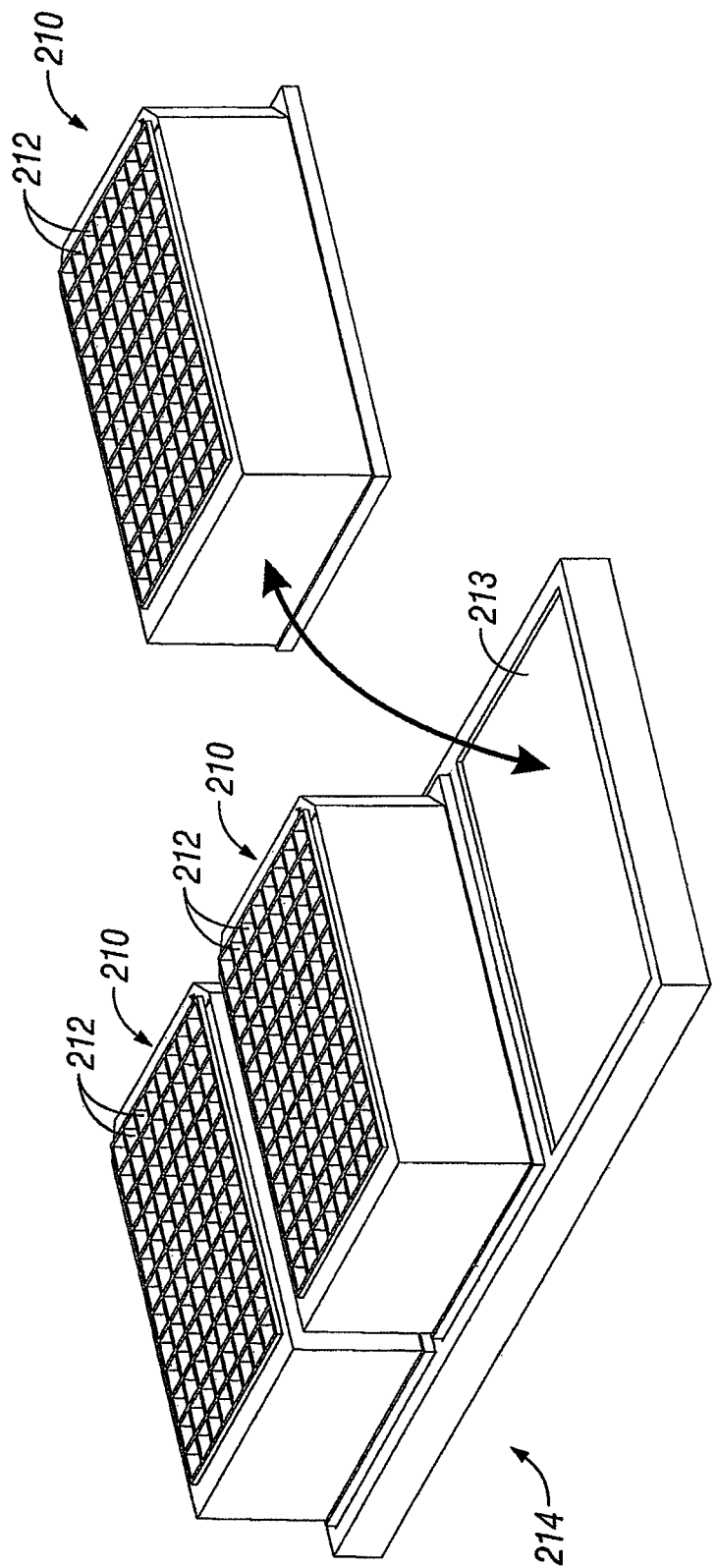
FIG. 19 is a perspective view of a seed portion tray system of the seed portion storage system according to one aspect of the present invention.
Figure 20:
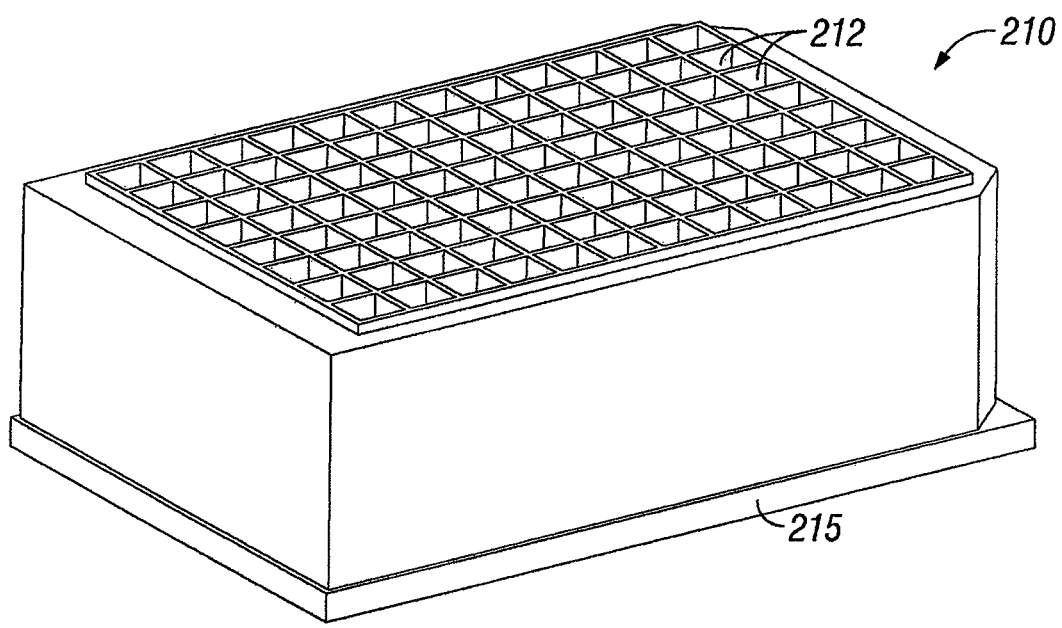
FIG. 20 is a perspective view of a seed portion container according to an exemplary aspect of this invention.

FIG. 14B is a perspective view of a shuttle system 47 for use in shuttling tray system 186 back and forth in the direction identified by arrow 183 shown in FIG. 14A relative to nozzles 180 of sampled seed distribution manifold 172. The shuttle system 47 comprises a driven plate 191 attached to slide brackets 188. Slide brackets 188 include apertures through which slide rails 192 pass through. Tray system 186 is attached to driven plate 191 via support posts 190 illustrated in FIG. 14A. Driven plate 191 is attached to a belt 198 driven by motor 196. Belt 198 is rotatably supported by a pulley 193 and motor 196. Each slide rail 192 is supported by a support bracket 194 attached to mounting plate 189. Motor 196 is attached to mounting plate 189 as well. Actuation of motor 196 causes belt 198 to rotate and impart movement to driven plate 191 which in turn moves tray system 186 in the direction of arrow 183 illustrated in FIG. 14A. Thus, as a row of seed are ablated and the sampled seed 148 travels through the sampled seed collection manifold 124 through conduits 150 and into sampled seed distribution manifold 172, sampled seed 148 drop through nozzles 176 and into respective wells in a row of the sampled seed container 182. The motor 196 is actuated and tray 186 is moved to the next position wherein the next empty row of wells 184 in sampled seed container 182 are moved into position underneath nozzles 180 of the sampled seed distribution manifold 172 whereby the next batch of sampled seed 148 are moved from ablation system 42 through sampled seed collection manifold 124 and sampled seed distribution manifold 172 into a row of wells within the sampled seed container 182. The position of each sampled seed 148 within each well 184 of sampled seed container 182 may be indexed and recorded so that sampled seed 148 maybe correlated with respective sample portions 166 of the seed for post ablation tracking, indexing and cataloging of each sampled seed 148 with its respective sampled portion 166. Thus, as each row of seed are ablated, the sampled seed 148 from a row 55 are communicated in singulation to wells within a row of sampled seed container 182. As rows of seed 55 are iterated through the ablation system, the sampled seed 148 are communicated to the next empty row in sampled seed container 182 by actuation of motor 196 causing tray 186 to shuttle along the direction of arrow 183 indicated in FIG. 14A. Movement and the timing of movement of tray system 186 may be controlled manually or by a control system of this invention, such as control panel 32.

FIGS. 14B, 15-16, 19 and 20 depict by various illustrations the seed portion distribution system and the shuttle system 47 used in combination with the same. Each conduit of the plurality of conduits 168 are in communication with the sample portion collection manifold 124 whereby the sample portion 166 of each seed is communicated in a singulated manner through sample portion collection manifold 152 and each respective conduit 168 into the inlet 202 of sample distribution manifold 200. Like the sampled seed distribution manifold 172, the sample portion distribution manifold 200 includes individual channels in communication with the inlet 202 and the outlet 204. Each conduit 168 communicates a single sample portion 166 of a seed through the inlet 202 and into the seed portion distribution manifold 200 through the outlet 204 via nozzles 208. The outlet 204 of each nozzle 208 of the seed portion distribution manifold 200 provides a means for moving each sampled portion 166 of a seed into an empty well in a sample portion container 210. In a preferred form of this invention, the sample portion container 210 comprises a microtiter plate. Other containers of varying size, shape, well configuration and functionality are contemplated. The seed portion storage system 36 further comprises a tray system 214 for supporting any number of sample portion containers 210. Tray system 214 may include a recessed floor 213 whereby a sample portion container 210 may be seated within the recessed floor 213 of the tray to prevent the sampled portion container 210 from shifting when shuttle system 47 moves tray system 214 in the direction indicated by arrow 211 in FIG. 16. The sample portion container 210 includes a plurality of wells 212 for housing a sample portion 166 of a seed. Each well in the sample portion container 210 may be indexed. In a preferred embodiment of this invention, the number of wells in the sample portion seed container 210 equal the number of wells 184 in the sampled seed container 182 shown in FIGS. 18A-B. Thus, the sampled seed 148 from a row of seed is communicated into the sampled seed container 182 occupying a single row and the sample portion 166 of each of those seeds is communicated into the wells 212 of a single row in the sample portion seed container 210, and these rows in the sampled seed container 182 and the sample portion seed container 210 are indexed or correlated with each other so as to track the position of the sampled seed 148 and its sampled portion 166 in the two containers.

Like the sampled seed storage system 46, the seed portion storage system 36 also includes an identical shuttle system 47 best illustrated in FIG. 14B. The shuttle system 47 illustrated in FIG. 14B is discussed in detail above. Tray system 214 is attached to driven plate 191 of the shuttle system 147 via posts 218. As the motor 196 is actuated, the driven plate 191 moves tray system 214 to the desired position underneath the nozzles 208 of seed portion distribution manifold 200. Thus, as each row of seed is ablated and the sample portion 166 from the row 55 is communicated through the sampled seed collection manifold 124 and seed portion distribution manifold 200, the sample portions 166 of each seed are collected in a single empty row of the sample portion container 210. Each time the ablation process is iterated, meaning another row of seed is introduced into the ablation process and seed portions are created from a row of seed, the sample portions 166 from the seed are communicated into the next empty row within sample portion container 210. This similar process occurs with the sampled seed container 182, thus the sampled seed 148 and the sample portion 166 of the seed are indexed with each other relative to their positions within the separate containers 182 and 210. Once a sample portion seed container 210 is full of sample portions 166 of seed, the sample portion seed container 210 may be removed from tray 214 and used for testing purposes, such as for culling the population of seed in the container. Similarly, when the sampled seed container 182 is full, the container may be removed from tray system 186 and sealed or covered. In the case where non-lethal separation of tissue from seed occurs in the ablation process, the sampled seed 148 collected in individual wells 184 in sampled seed container 182 may be planted if it is determined that the sampled seed 148 contains desired characteristics and traits. The correlation between the sampled seed and the seed portion may be tracked, indexed and catalogued throughout this process.

Methods

Figure 21A:
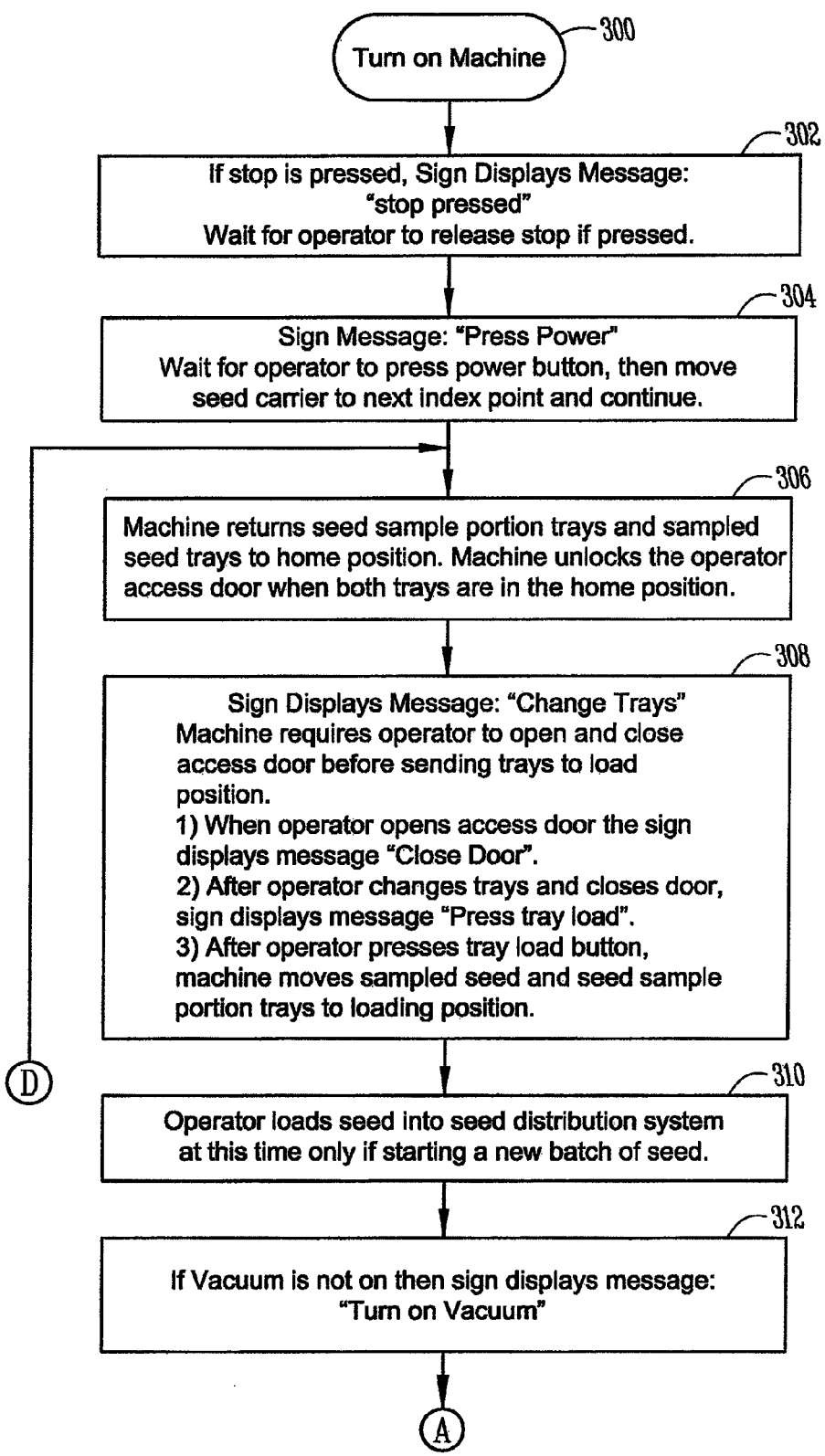
FIGS. 21A-C show a flowchart for a method or process of this invention.
Figure 21B:
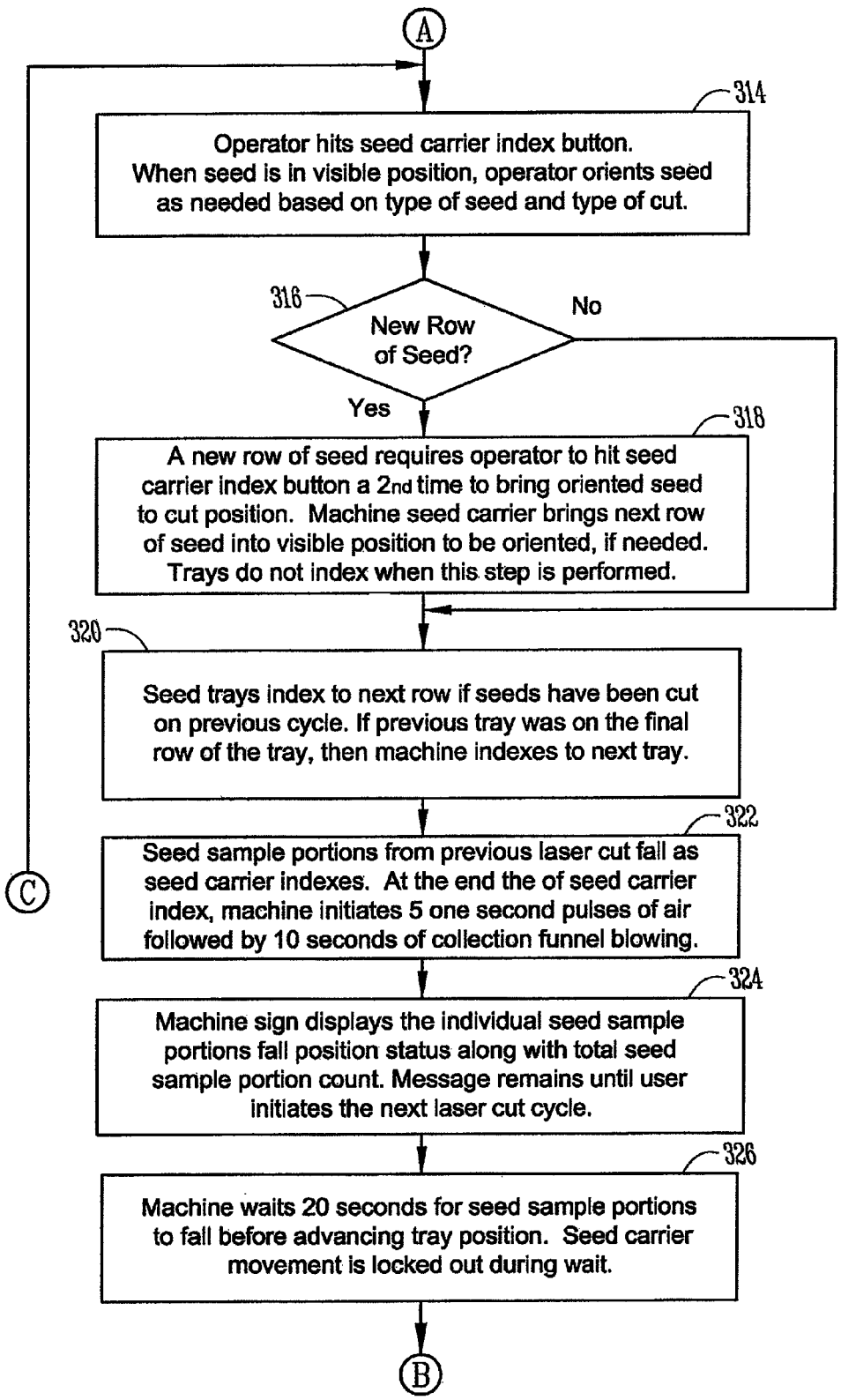
Figure 21C:
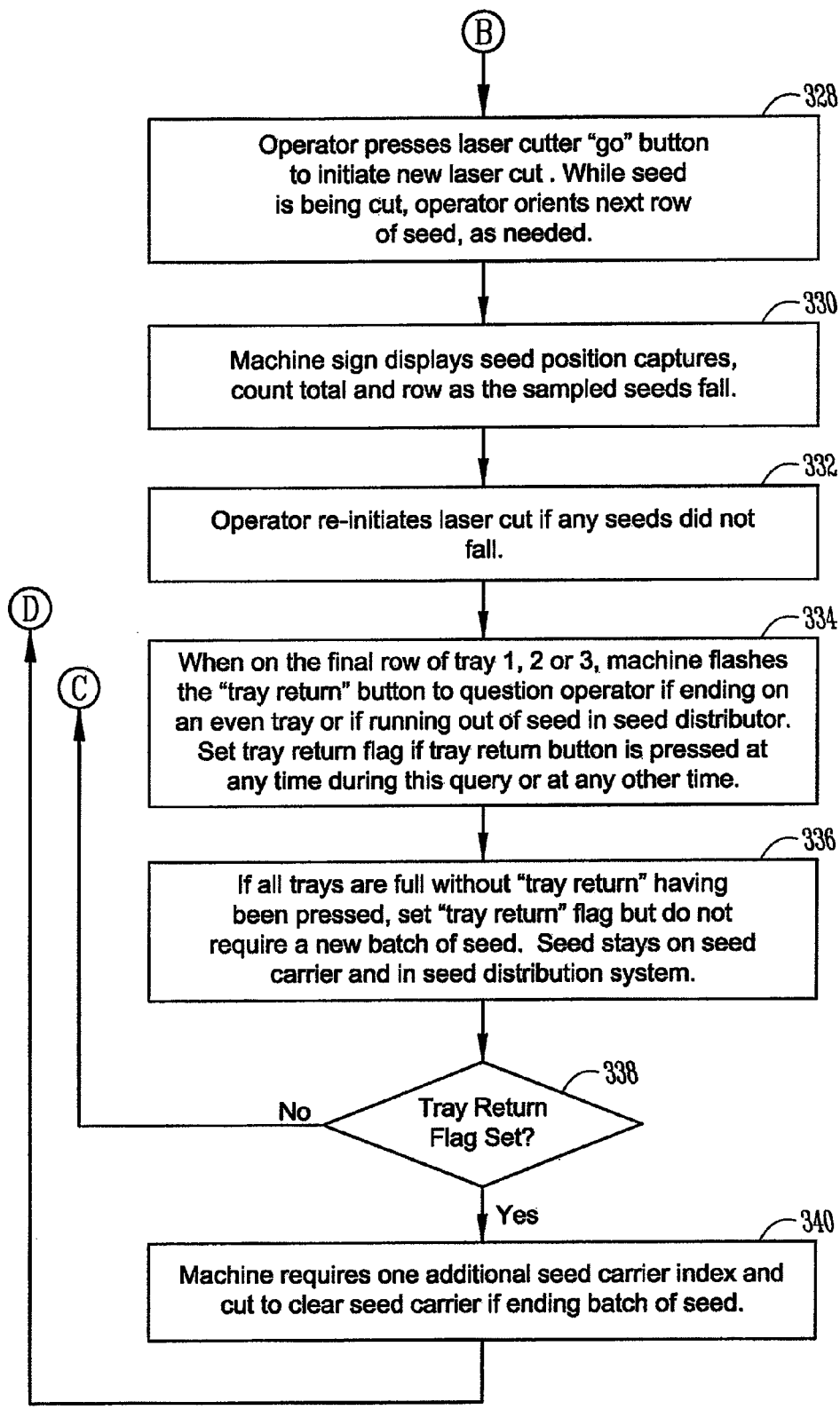

FIGS. 21A-C illustrate a method of this invention described by one or more steps. The steps of one method of this invention include, but are not limited by or to, those illustrated in FIGS. 21A-C. To begin processing seed, the seed sampler system 10 is first activated or turned on (step 300). At any time during processing, the seed sampler system 10 may be stopped, and maintained in the "stop pressed" mode until the operator releases the system 10 from the "stop pressed" mode (step 302). The display panel 18 may include a display of text or other illustrations indicative of such an operation. For example, at step 302 the display panel 18 may display a message such as "stop pressed". If system 10 has been turned on, display panel 18 displays a "Press Power" message (step 304). System 10 may remain in a hibernation or sleep mode until an operator presses the power button. Pressing the power button moves seed carrier 50 to next index point, and the system 10 is now ready to continue with the process. If the seed sample portion tray 214 and/or sampled seed tray 186 are not in the home position, the system 10 moves the tray(s) to the home position. When both trays are in the home position, system 10 unlocks the operator access door to allow operator access to the trays (step 306). Display panel 18 displays a message to "Change Trays". The system 10 requires that the door providing access to the trays be opened and closed before moving trays to the load position (step 308). When the access door is in the open position, the display panel 18 displays a message to "Close Door". After trays are changed, if needed, and the access door is moved to the closed position the display panel 18 displays the message "Press Tray Load" (step 308). After the operator presses the tray load button, the system 10 moves sampled seed and seed sample portion trays to a loading position (step 308). A batch or batches of seed, e.g., soybean or other seed, are poured or inserted into the seed distribution system 38, if a new batch of seed is to be processed (step 310). If an existing batch of seed is still in the seed distribution system 38, the seed batch loading step may be skipped. The seed sampler system 10 is activated at the control panel 32 by an operator. The operator may at any time enter operating parameters into the control panel 32 for controlling the functionality of seed sampler system 10. For example, the operator may enter control parameters relating to the power and speed and operation of the laser, the particular location of the cut depending upon the type of seed, the number of seed to process, or other operating parameters.

With a batch or batches of seed having been introduced into the seed distribution system 38 and operating parameters input into the control panel 32, the operator may begin processing seed. If at this point the vacuum system for system 10 has not been activated the operator is instructed with a message via display panel to "Turn on Vacuum" (step 312). When the vacuum system is activated, a negative pressure system (e.g., a vacuum system) is activated so that negative pressure manifold 68 is under vacuum. To move a row of seed to a position visible by the operator, the operator presses the seed carrier index button (step 314). The operator may orient each of the seed in a visible row, as needed, based on the type of seed being processed and the type of cut being performed (step 314). As motor 86 moves a first row of seed staging positions 55 into the seed distribution system 38, lateral port 58 also moves into communication with negative pressure manifold 68 whereby negative pressure is communicated through lateral port 58 in communication with seed staging port 54 for retaining a seed at each seed staging position 52 within the row 55. The seed carrier 50 continues to rotate in the direction identified by arrows 108 in FIG. 8C. As a row of seed staging positions 55 move through the seed distribution system 38, a seed 62 is picked up and retained at each staging position 52 as a result of the negative pressure or vacuum being communicated through each seed staging port 54 of each seed staging position 52. The system 10 continues by ascertaining from the operator if a new row of seed is desired (step 316). If the input from the operator is no, the system 10 jumps to step 320, whereas if the input is yes, the system continues with step 318. Answering yes to the query at step 316 requires that the operator press the seed carrier index button a $2^{nd}$ time for picking up a new row of seed, which rotates the row of oriented seed to the cutting position as described in greater detail below. Rotation of the seed carrier causes rotation of the next row on the seed carrier into a position visible to the operator where each of the seed in the row may be oriented, if needed (step 318). The trays do not index when this step is performed. As the seed carrier rotates, another row of seed staging positions 55 is rotated into the seed distribution system 38. As the next row of seed staging positions 52 is rotated into the seed distribution system 38, lateral port 58 associated with the row of seed staging positions 52 are brought into communication with negative pressure manifold 68 whereby negative pressure or vacuum is communicated through the seed staging ports 54 to each of the seed staging positions 52 in the row 55. Thus, each seed staging position 52 in the row picks up or retains a seed at a staging position 52 when the seed carrier 50 is rotated through the seed distribution system 38. The subsequent rotation of seed carrier 50 and each row 55 of seed staging positions 52 through the seed distribution system 38 continues until the first row of seed arrives at the ablation system 42. When a row of seed staging positions 55 having seed retained at each position enters into ablation system 42, the rotation of seed carrier 50 is stopped for a time to permit the ablation process to occur. The ablation process preferably requires that the operator press the laser cutter "go" button to initiate laser cutting. While the row of seed at the ablation system is being cut, the operator may be orienting the next row to enter the ablation system, if needed (step 328). The laser ablation device 126 is moved into the cutting position wherein a portion of the device is docked or seated in the lateral seat 140 in the outer peripheral surface 61 of seed carrier 50. The position of laser ablation device 126 relative to the outer peripheral surface 61 of the seed carrier 50 determines the location of the cut on the seed made by the laser 146. The laser ablation device moves in a direction along arrow 128 indicated in FIG. 10 relative to the row of seed at each seed staging position 52. Thus, as the laser ablation device 126 passes through the first seed, the sampled seed 148 separates from the sample portion 166 still retained at the seed staging position 52 and falls by gravity, or impart by pneumatic assistance, through the sampled seed collection manifold 124 and the sampled seed distribution manifold 172 into the first well 184 in the sampled seed container 182. The laser ablation device 126 continues to move laterally across the row of seed as indicated by arrow 128 in FIG. 10. As each seed is ablated, the sampled seed 148 releases and drops by gravity or impart by pneumatic assistance through the sampled seed distribution manifold 172 and seed portion distribution manifold 200 into respective wells 184 in the sampled seed container 182. The panel display 18 displays seed position captures, count totals and row numbers as the sampled seeds fall (step 330). The operator may re-initiate laser cutting if any of the seeds did not fall or separate from the sample portion of the seed (step 332). After the laser ablation device 126 has completed its pass across the row of seed, the ablation device 126 moves away from the outer peripheral surface 61 of the seed carrier 50 to allow the seed carrier 50 to be rotated so that the next row of seed move into the ablation system 42 and the row of seed that was previously ablated moves the sampled portions 166 of the seed into the sampled portion collection manifold 152. When on the final row of any one of the trays, the system flashes the "tray return" button to question the operator if ending on an even tray or if the seed distributor is nearly empty. The system sets a tray return flag for marking it previous position if tray return button is pressed at any time during this query or at any other time (step 334). However, if all trays are full without "tray return" having been pressed, the system sets the "tray return" flag but does not require a new batch of seed. The present seed in the system stays on the seed carrier and in the seed distribution system (step 336). If input to the system regarding the "Tray Return Flag Set" query is a yes, the system requires one additional seed carrier index and cut to clear seed carrier if ending with a batch of seed (step 340), and thus the process starts over again at step 306. On the other hand, if the operator responds no to the query, the system returns to step 314.

The sample portions 166 of each seed moved into the sample collection area 156 of the sample portion collection manifold 152 are released from the seed carrying positions 52 as the negative pressure or vacuum that was used to retain the sample portion 166 of each seed at the seed staging positions 52 is cut because lateral port 58 is no longer in communication with negative pressure manifold 68. As seed carrier 50 continues to rotate the row of ablated seed toward the sample collection area 156, lateral port 58 rotates into communication with positive pressure manifold 76. A positive pressure source such as a compressor or the output side of a negative pressure source such as a vacuum (not shown) is attached to the inlet 78 of positive pressure manifold 76 for providing a stream of air that travels through lateral port 58, seed staging ports 54 and out the seed staging position 52 to kick-off or release each one of the sample portions 166 of seed from the seed staging positions 52 whereby the sample portions 166 fall by gravity, or impart by pneumatic assistance, through the sample portion collection manifold 152 and seed portion distribution manifold 200 into a respective well 212 in sample portion seed container 210. Actuation and the timing of actuation of sources providing either or both negative or positive pressure to system 10 may be controlled manually or by a control system of this invention, such as control panel 32.

The trays do index to the next row of the container if seeds were cut on the previous cycle. If the previous tray was on the final row of the tray, the system 10 indexes to the next tray (step 320). Seed sample portions 166 from previous laser cut fall into the seed collection system as the seed carrier 50 indexes (step 322). Tray indexing or iteration is accomplished as shuttle systems 47 iterate tray system 186 one row to bring a new empty row of wells 184 into communication with nozzles 180 of sampled seed distribution manifold 172. With the sampled seed collection manifold 124 and sampled seed distribution manifold 172 now in communication with a new row of wells 184 in sampled seed container 182, the laser ablation device 126 is activated to ablate the row of seed 55. The system 10 waits ~20 seconds for seed sample portions to fall before advancing tray the tray system. Seed carrier movement is preferably locked out during this waiting period (step 326). As seed 62 in the row 55 are ablated by the ablation system 42, the sampled seed 148 ablated from the sample portion 166 of the seed falls by gravity, or in part by pneumatic assistance, through the sampled seed collection manifold 124 and into respective wells 184 in the sampled seed container 182. For example, at the end of the seed carrier index, system 10 initiates 5 one second pulses of air followed by 10 seconds of collection funnel blowing (step 322). Panel display 18 may provide the operator with one or more displays indicating the individual seed sample portions fall position status along with total seed sample portion counts. The message may remain on the display until the operator initiates the next laser cutting cycle (step 324). When the laser ablation device 126 has completed the row, the laser ablation device moves away from the outer peripheral surface 61 of seed carrier 50 so that seed carrier 50 may be rotated. As seed carrier 50 is rotated, any remaining sample portions 166 of seed still hung up or attached at seed staging positions 52 are kicked-off, separated or removed by the sample kick-off device 164 in the sample portion collection manifold 152. Similarly, as seed carrier 50 rotates, any sampled seed 148 that has not already released from the sample portion 166 after ablation is removed or kicked-off as seed carrier 50 rotates the row of ablated seed past the sample kick-off device 164 in the sample portion collection manifold 152.

When a row of seed 55 are positioned at the ablation system 42 for ablating, lateral positive pressure port 60 is in communication with positive pressure manifold 72. A positive pressure system, such as a compressor or the outlet of a vacuum or negative pressure system, may be used to feed air to the inlet 74 of positive pressure manifold 72. Air traveling through positive pressure manifold 72 flows through lateral positive pressure port 60 and out positive pressure port 56 surrounding each seed staging position 52. The exiting air from recess 64 surrounding seed staging position 52 helps remove any smoke, dust, debris, or other material resulting from the ablation process away from the cutting area to maximize the efficiency of the laser ablation device 126. Each time a new row of seed 55 are iterated through the ablation system 42, the shuttle system 47 iterates both the sampled seed container 182 and the sample portion seed container 210 so that an empty row of wells in both containers are brought into communication with nozzles 180 and 208 of the sampled seed distribution manifold 172 and the seed portion distribution manifold 200.

As a row of seed staging positions 52 rotate out of the sample collection area 156 in the sample portion collection manifold 152, lateral port 58 moves out of communication with positive pressure manifold 76 so that the lateral port is now open to ambient pressure until the seed carrier continues rotation to the point where the lateral port 58 is brought back into communication with the negative pressure manifold 68 at which point the row of seed staging positions 55 in communication or associated with this specific lateral port 58 are now under negative pressure or vacuum when rotated back into the seed distribution system 38 for picking up another batch of seed at each seed staging position 52.

The aforementioned steps continue until the desired amount of seed have been processed. Thus, it is evident from the above description that this invention provides a high throughput seed sampling method that meets or exceeds all of the aforementioned objectives.

System

The seed sampler system 10 provides high throughput, automated bulk sampling and indexing of a batch of seed. The seed sampler system 10 includes an ablation system 42. In a preferred form, the ablation system 42 comprises a laser ablation device emitting a laser 146 providing a controlled cutting path moveable relative to seed carrier 50. The seed sampler system 10 also comprises a seed distribution system 38. Seed distribution system 38 comprises a local storage point for a batch or batches of seed. The seed distribution system 38 is in communication with seed carrier 50 whereby seed within seed distributor 96 is channeled and oriented via vanes 98 and alleys 99 in seed distributor 96 in its descent toward collection area 104 adjacent the outer peripheral surface 61 of seed carrier 50.

Seed sampler system 10 also includes a control system comprising a control panel 32, control box 28 and display panel 18. The programming or other inputs from an operator, including network instructions from a computer or controller, are used to control operation of seed sampler system 10. Seed carrier 50 includes one or more ports that by rotation of seed carrier 50, are brought into communication with positive or negative pressure fields. For example, seed carrier 50 includes a plurality of seed staging positions 52. In one aspect of this invention, seed staging positions 52 are aligned in sequential order in rows 55 on the outer peripheral surface 61 of seed carrier 50. Each seed staging position 52 includes a seed staging port 54. The seed staging port 54 is communication alternatively with a negative pressure manifold 68 or a positive pressure manifold 76. Each seed staging position 52 also includes a positive pressure port surrounding at least partially each seed staging position 52 and the corresponding seed staging port 54 whereby air is exhausted through recess 64 around each seed staging position 52 when lateral positive pressure port 60 is brought into communication with positive pressure manifold 72 by rotating seed carrier 50. Instructions from the control system of this invention provide input to motor 86 for rotating belt 82 for imparting rotation to seed carrier 50. The control system of this invention monitors the position of seed carrier 50, including each respective row of seed staging ports 55 on the outer peripheral surface 61 of seed carrier 50, by receiving feedback from seed carrier position sensing system 51.

While lateral ports 58 are in communication with negative pressure manifold 68, a negative pressure field is communicated through lateral port 58, seed staging port 54 and to each seed staging position in a row of seed staging positions 55 in communication with the lateral port 58. In a preferred aspect of this invention, a row of seed staging ports 54 are brought into communication with negative pressure manifold 68 when the row is rotated into seed distribution system 38. The negative pressure or vacuum at each seed staging position 52 picks up and retains a seed for moving from the seed distribution system 38 to the ablation system 42. Seed staging positions 52 are in the retention mode whenever lateral port 58 is in communication with negative pressure manifold 68. Negative pressure manifold 68 may be configured so that any number of lateral ports 58 at one given time are in communication with negative pressure manifold 68. For example, negative pressure manifold 68 may be configured to be in communication with more lateral ports 58 (see FIG. 3B) or less lateral ports 58 (see FIG. 3A) at any given time depending on the radial distance between where seed 62 is picked up and seed portion 166 is dropped into manifold 152. In the embodiment shown in FIG. 3B, a lateral port 58 is in communication with negative pressure manifold 68 from the time it is rotated into the seed distribution system 38 until each reaches the sample portion collection manifold 152 (roughly 270 degrees of rotation later). Conversely, in the embodiment shown in FIG. 3A, a lateral port 58 is in communication with negative pressure manifold 68 roughly 190-200 degrees of seed carrier 50 rotation because of the variation in position of sample collection manifold 152. In either case, after a lateral port 58 rotates out of communication with negative pressure manifold 68, a row of seed staging positions 55 experience a positive pressure field when the lateral port 58 associated with the row of seed staging ports is brought into communication or is rotated into communication with positive pressure manifold 76. During ablation, lateral positive pressure port 60 associated with a row of seed staging positions 55 is in communication with positive pressure manifold 72 whereby air from a positive pressure source is communicated through positive pressure ports 56 associated with seed staging positions 52.

The ablation system 42 comprises a laser that is positionable relative to the outer peripheral surface 61 of seed carrier 50 by one or more motors or controllers. During the ablation process, a ventilation system 16 aids in removing any unwanted smoke, dust or other debris resulting from the ablation process. The ablation process occurs at least partially in the seed collection system 22. The seed collection system 22 comprises a sampled seed distribution system 44 and a seed portion distribution system 48. During ablation of a row of seed, the row of seed is in communication with sampled seed distribution system 44. As each seed in a row is ablated by laser 146, the sampled seed 148 separates from the sample portion 166 of the seed and falls into sampled seed distribution system 44. A pneumatic system ported into sampled seed distribution system 44 may be used to assist in the descent of each sampled seed 148.

The seed collection system 22 includes a pass-through 130 whereby laser 146 passes through without touching the walls of seed collection system 22. The laser 146 passes through the pass-through 130 and eventually diffuses before impacting a wall or surface of the seed sampler system 10. Other diffusive means are contemplated, for example a diffusive membrane or surface may be positioned within the cutting pathway of laser 146 to diffuse the laser.

The sampled seed distribution system 44 may include a sampled seed kick-off device 144 to assist in removing the sampled seed 148 from the seed staging position 52. For example, if after a seed is ablated, the sampled seed 148 becomes hung up or remains attached at the seed staging position 52, sampled seed kick-off device 144 aids in separating the sampled seed 148 from a seed staging position 52 by kicking-off the sampled seed 148 when rotated past sampled seed kick-off device 144. Sampled seed kick-off device 144 may include an edge of a plate or other fixed, flappable or semi-rigid membrane to aid in kicking-off or releasing sampled seed 148 from each seed staging position 52.

Rotation of seed carrier 50 in the direction of arrow 154 illustrated in FIGS. 11A-B moves a row of ablated seed from being in communication with sampled seed distribution system 44 to be in communication with seed portion distribution system 48. Rotation of a row of ablated seed (having the remaining seed portion 166) from communication with the sampled seed distribution system 44 to communication with the sample portion distribution system 48 changes the pressure field at the seed staging positions 52 from a negative pressure field to a positive pressure field wherein the seed portions 166 retained at the row of seed staging positions 55 are blown off or kicked-off the seed staging position 52. The falling sampled portions 166 of seed descend through the seed portion distribution system 48. In a case where a sampled portion 166 of seed does not separate from the seed staging position 52, the sample portion 166 of the seed is kicked-off or brushed off of the seed staging position 52 by a sample portion kick-off device 164. The sample portion kick-off device 164 may include a flappable, rigid or semi-rigid plate or edge in close proximity to the outer peripheral surface 61 of seed carrier 50 that scrapes, rubs or dislodges the seed sample portion 166 off of the seed staging position 52 to release it into the seed portion distribution system 48 for collection in the seed storage system 24. Dislodging of a sample portion 166 of seed from a seed staging position 52 occur as seed carrier 50 is rotated in the direction of arrow 154 illustrated in FIGS. 11A-B.

The individual portions of the seed, the sampled seed 148 and the sample portion 166 of each seed are communicated in separation from each other to the seed storage system 24. The sampled seed distribution system 44 is in communication with seed storage system 24 via a sampled seed distribution manifold 172. Similarly, the seed portion distribution system 48 is in communication with seed storage system 24 via a sample portion distribution manifold 200. The sampled seed distribution manifold 172 and sample portion distribution manifold 200 both include separated channels or conduits in communication with conduits 150 and 168. Sampled seed 148 are communicated through conduits 152 and sampled seed distribution manifold 172. Confirmation of a sampled seed passing through sampled seed distribution manifold 172 is provided via seed drop sensors 178 positioned relative to conduits 150 and sampled seed distribution manifold 172. Nozzles 180 at the outlet 176 of sampled seed distribution manifold 172 are positioned relative to a row of wells 184 in sampled seed container 182. A shuttle system 47 receiving instructions from an operator control panel 32, or control system of the seed sampler system 10 moves tray system 186 into position beneath nozzles 180 of sampled seed distribution manifold 172. Similarly, another identical shuttle system 47 positions tray system 246 so that a row of empty wells 212 in sample portion seed container 210 are positioned directly beneath nozzles 208 at the outlet 204 of sample portion distribution manifold 200.

Sample portions 166 of seed are released from seed staging positions and travel in their descent through seed portion distribution system 48, through conduits 168 and into sample portion distribution manifold 200. Individual conduits 168 carry each sample portion 166 into an individual empty well 212 in sample portion seed container 210. Seed drop sensors 206 monitor and detect the drop of sampled portions 166 as they pass through conduit 168 and sample portion distribution manifold 200 into an empty well 212 within sampled portion seed container 210.

The sampled seed tray system 186 iterates by positioning another new unoccupied row of wells of sampled seed container 182 directly beneath nozzles 180 at the outlet 176 of sampled seed distribution manifold 172. Similarly, the seed portion tray system 214 iterates positioning an unoccupied row of wells 212 of sample portion seed container 210 directly beneath nozzles 208 of outlet 204 of sample portion distribution manifold 200. This process continues until the entire batch of seed has been processed or until the desired amount of wells within each sampled seed container 182 and sampled portion container 210 have been filled.

Seed sampler system 10 also includes a pneumatic system. The pneumatic system comprises one or more means for providing a positive or negative pressure field to one or more of the pressure enable functions of system 10. For example, the negative pressure field may be provided by the inlet of a vacuum and the positive pressure field by the outlet of the same or another vacuum source. Similarly, a positive pressure field may be provided by communication of positive pressure air from a compressor or other positive pressure source. In a preferred embodiment of this invention, negative pressure manifold 68 has an outlet 70 in communication with a negative pressure source, positive pressure manifold 76 has an inlet 78 in communication with a positive pressure source, and positive pressure manifold 72 has an inlet 74 in communication with a positive pressure source of the pneumatic system 49. Further, in the case where pneumatic assistance is used in aiding the descent of either one or both of the sampled seed 148 or sample portion 166 of each seed through the seed collection system 22, pneumatic system 49 may be in communication with the seed collection system whereby a positive pressure field, or a negative pressure field, if needed, is provided at each channel or a series of channels in the sampled seed distribution system 44 and seed portion distribution system 48. For example, pneumatic system 49 may include one or more positive pressure conduits in communication with ports 157, 159 and 161 in seed collection system 22 illustrated in FIG. 12A-B. Ports 157, 159 and 161 may be oriented so as to assist in the descent of each sampled seed 148 and sample portion 166 into the seed storage system 24.

The exemplary embodiments of the present invention have been set forth within the drawings and in the foregoing description and although specific terms are employed, these are used in the generically descriptive sense only and are not used for the purposes of limitation. Changes in the formed proportion of parts as well as in the substitution of equivalents are contemplated as circumstances may suggest or are rendered expedient without departing from the spirit and scope of the invention as further defined in the following claims.

What is claimed is:

1. A high throughput system for automated bulk sampling and indexing of a batch of seed, comprising:
    an ablation subsystem having a controlled cutting path;
    a seed handling subsystem comprising:
        a) a staging system comprising a plurality of seed staging positions for staging a batch of seed in a sequential manner;
        b) a carrier system for simultaneously presenting said seed staging positions at the cutting path for removing a sample portion from each seed in the batch; and
        c) an automated seed retention and release system for switching a plurality of seed staging positions to:
            i) a seed retention mode; or
            ii) a seed release mode,
    wherein the carrier system cycles a plurality of seed staging positions through at least one or more sequence of events comprising:
        a) a seed staging event;
        b) a seed sample cutting event; or
        c) a sampled seed release event; and
    wherein the plurality of seed staging positions comprise one or more subset of seed staging positions, wherein one subset is operating in the seed retention mode while another subset is operating in the seed release mode.

2. The system of claim 1 wherein at least one subset of staging positions is at the seed staging event while another subset is at the seed sample cutting event.

* * * * *